(12) United States Patent
Roy et al.

(10) Patent No.: US 10,736,968 B2
(45) Date of Patent: Aug. 11, 2020

(54) CELLULAR SIGNALLING INHIBITORS, THEIR FORMULATIONS AND METHODS THEREOF

(71) Applicants: INVICTUS ONCOLOGY PVT. LTD., Delhi (IN); THE BRIGHAM AND WOMEN'S HOSPITAL, INC., Boston, MA (US)

(72) Inventors: Monideepa Roy, Andover, MA (US); Goutam Biswas, Delhi (IN); Hemant Suryavanshi, Delhi (IN); Anubhab Mukherjee, Delhi (IN); Ashish Kulkarni, Arlington, MA (US); Shiladitya Sengupta, Philadelphia, PA (US)

(73) Assignees: INVICTUS ONCOLOGY PVT. LTD., Delhi (IN); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 16 days.

(21) Appl. No.: 16/076,955

(22) PCT Filed: Feb. 11, 2017

(86) PCT No.: PCT/IB2017/050770
§ 371 (c)(1),
(2) Date: Aug. 9, 2018

(87) PCT Pub. No.: WO2017/137958
PCT Pub. Date: Aug. 17, 2017

(65) Prior Publication Data
US 2019/0046650 A1    Feb. 14, 2019

Related U.S. Application Data

(60) Provisional application No. 62/293,928, filed on Feb. 11, 2016.

(51) Int. Cl.
| | | |
|---|---|---|
| A61K 47/54 | (2017.01) |
| C07J 41/00 | (2006.01) |
| C07D 417/12 | (2006.01) |
| C07J 43/00 | (2006.01) |
| C07J 9/00 | (2006.01) |
| A61K 47/69 | (2017.01) |
| A61K 47/55 | (2017.01) |
| A61P 35/00 | (2006.01) |
| A61K 31/4439 | (2006.01) |
| A61K 31/575 | (2006.01) |
| A61K 45/06 | (2006.01) |

(52) U.S. Cl.
CPC ........ *A61K 47/554* (2017.08); *A61K 31/4439* (2013.01); *A61K 31/575* (2013.01); *A61K 45/06* (2013.01); *A61K 47/545* (2017.08); *A61K 47/55* (2017.08); *A61K 47/6929* (2017.08); *A61P 35/00* (2018.01); *C07D 417/12* (2013.01); *C07J 9/00* (2013.01); *C07J 41/0005* (2013.01); *C07J 41/0055* (2013.01); *C07J 41/0088* (2013.01); *C07J 43/003* (2013.01)

(58) Field of Classification Search
None
See application file for complete search history.

(56) References Cited

FOREIGN PATENT DOCUMENTS

| WO | 2007121484 A2 | 10/2007 |
| WO | 2013188763 A1 | 12/2013 |

OTHER PUBLICATIONS

Krauser et al., Xenobiotica (2015), 45(2), pp. 107-123.*
Radwan et al., "Targeting cancer using cholesterol conjugates." Saudi Pharm J 22(1): 3-16 (2014).

* cited by examiner

*Primary Examiner* — Brian J Davis
(74) *Attorney, Agent, or Firm* — Nixon Peabody LLP

(57) ABSTRACT

The present disclosure relates generally to Cellular Signalling inhibitors of compound of Formula I, compositions and formulations comprising the same, methods, processes, and uses thereof. In particular, the present disclosure provides CSF-1R inhibitors demonstrating sustained inhibition of CSF/CSF1R signalling pathway with decreased toxicity. The present disclosure also provides supramolecular combinatorial therapeutics, wherein a CSF-1R inhibitor is combined with one or more of a chemotherapeutic agent, a kinase inhibitor, and an immunoregulator, each of which is optionally conjugated with a lipid. The present disclosure also provides a method for treating cancer, allergy, Systemic lupus erythematosus, nephritis, Chronic Obstructive Pulmonary Disease, and abnormal macrophage functions or any combinations thereof.

Compound of Formula I

22 Claims, 13 Drawing Sheets

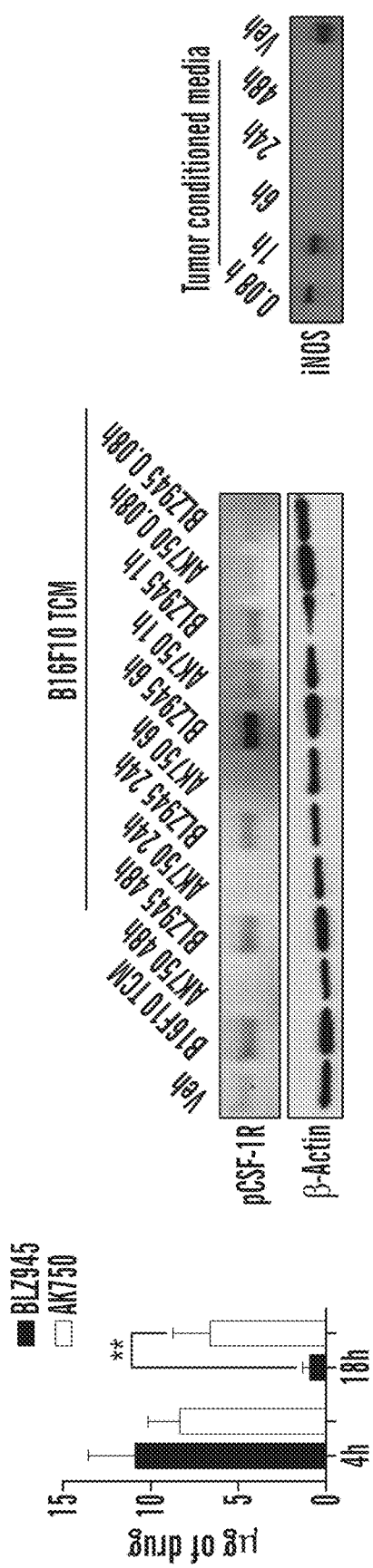

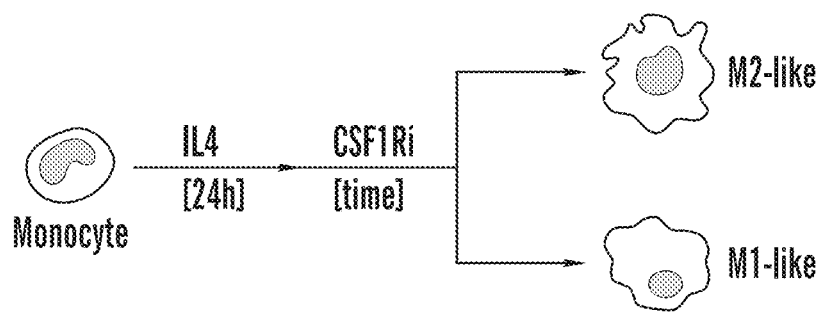
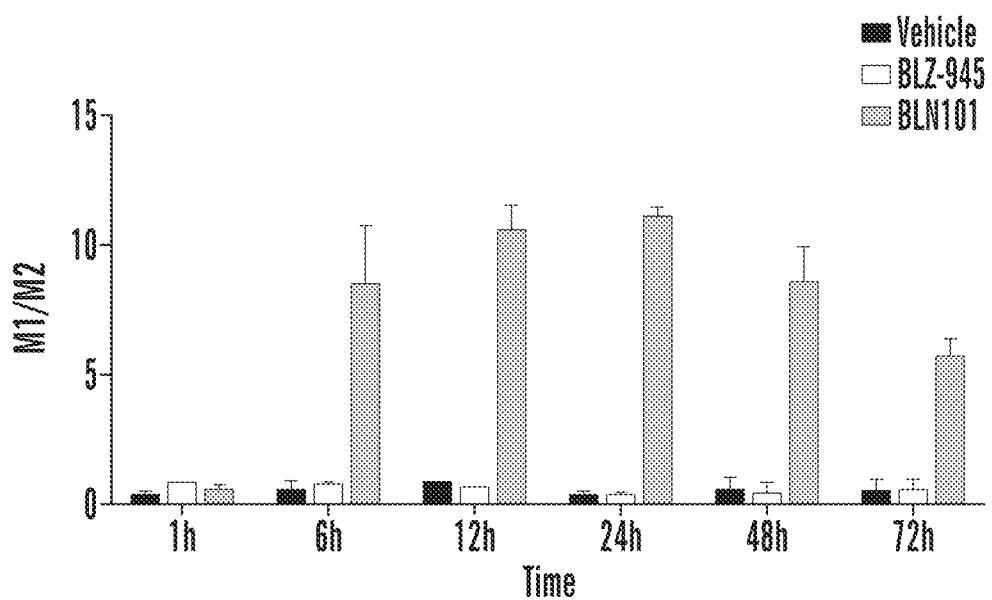
FIG. 4

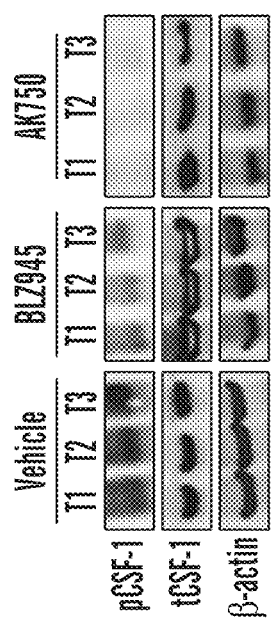
FIG. 6E
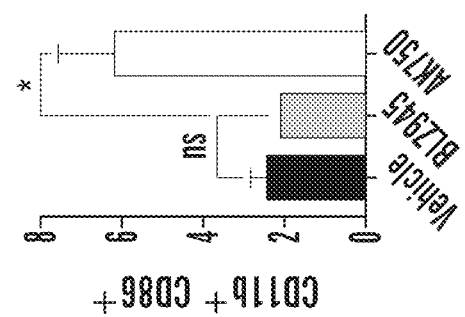
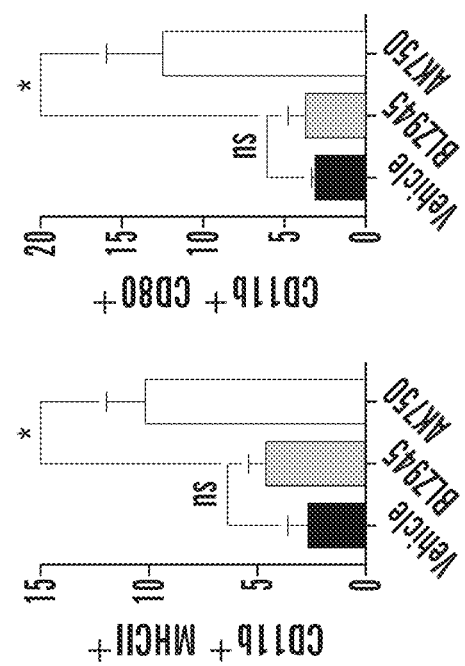
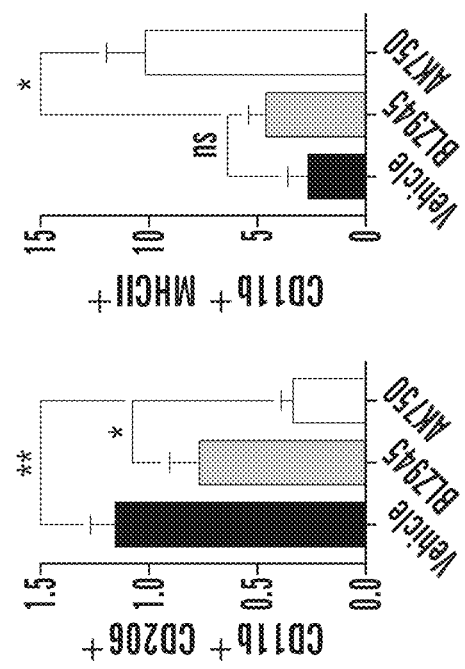
FIG. 6F

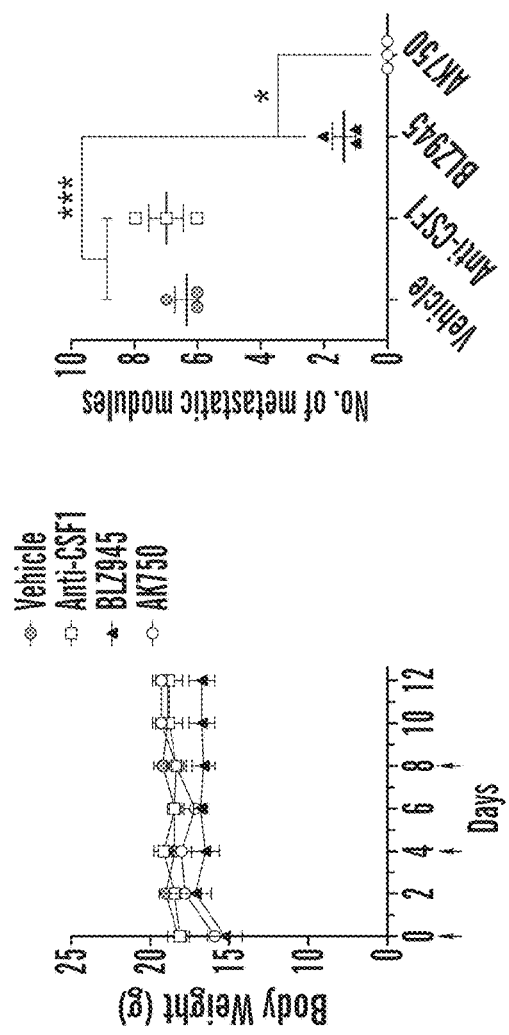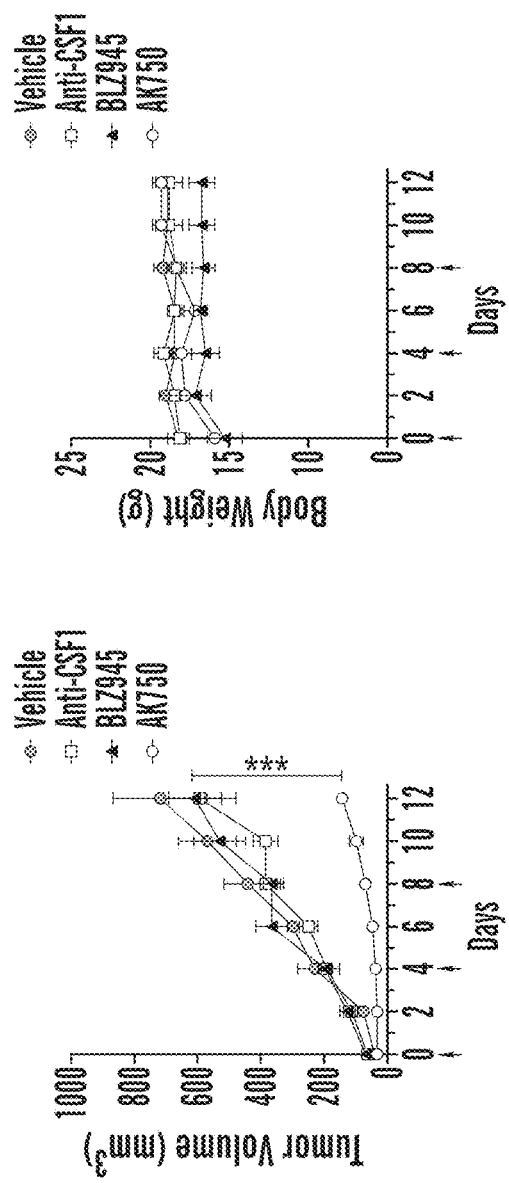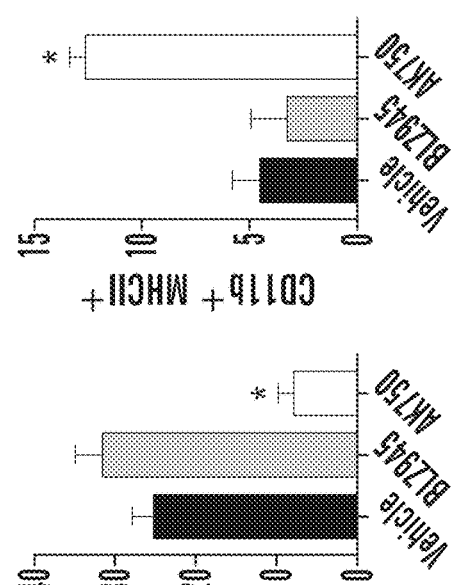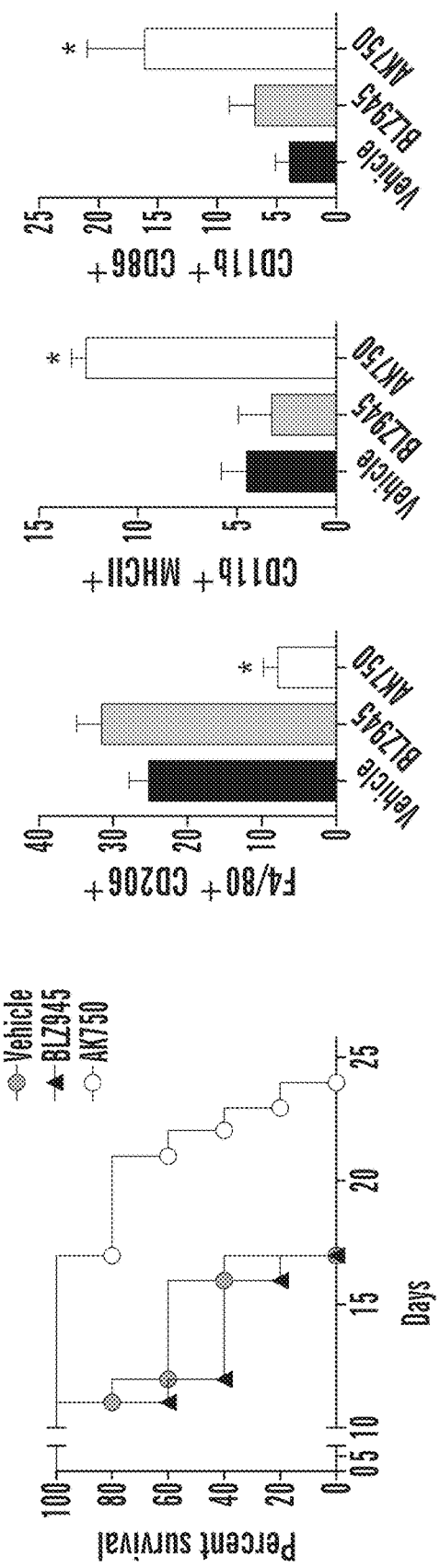
FIG. 7A  FIG. 7B  FIG. 7C  FIG. 7D  FIG. 7E

CELLULAR SIGNALLING INHIBITORS, THEIR FORMULATIONS AND METHODS THEREOF

CROSS REFERENCE TO RELATED APPLICATIONS

This application is a 371 National Phase Entry of International Patent Application No. PCT/IB2017/050770 filed Feb. 11, 2017, which claims benefit under one or more of 35 U.S.C. § 119(a)-119(d) of U.S. Patent Application No. 62/293,928, filed Feb. 11, 2016, the contents of both of which are incorporated herein by reference in their entirety.

TECHNICAL FIELD

The present disclosure relates generally to Cellular Signalling inhibitors, compositions and formulations comprising the same, and uses thereof. In particular, the present disclosure provides CSF-1R inhibitors demonstrating sustained inhibition of CSF/CSF-1R signalling pathway with decreased toxicity. The present disclosure also provides supramolecular combinatorial therapeutics, wherein the CSF-1R inhibitor is combined with one or more of a chemotherapeutic agent, a kinase inhibitor, and an immunoregulator, each of which is optionally conjugated with a lipid.

BACKGROUND

Targeted therapies have been in the limelight as cancer therapeutics for the last few years. They have resulted in high response rates and improved overall survival in patients with cancer. However, consistent with other oncogene-targeted therapies, initial patient response is of limited durability and tumors eventually relapse.[i]

The tumor microenvironment is increasingly recognized to play an important role in tumor proliferation, invasion, metastasis, and chemoresistance. It provides a conducive niche to the tumor through immunosuppression. Overcoming this immunosuppressive nature of the tumor microenvironment has been of particular interest in cancer therapy. Tumor cells manipulate the surrounding environment by producing cytokines that suppress cytolytic T-cells and recruit immunosuppressive cells.[ii]

Colony stimulating factor 1 (CSF-1) is one such cytokine secreted by several cancer cell types. It induces the proliferation and differentiation of immunosuppressive myeloid cells such as M2 polarized macrophages and myeloid derived suppressor cells (MDSC) by binding to the CSF-1 receptor (CSF-1R) on cell surface.[iii] Cellular signalling mediated by colony-stimulating factor 1 (CSF1) and its receptor CSF-1R plays a critical role in monocyte differentiation and generation and activity of tissue-resident macrophages. The overexpression of CSF1 is associated with poor prognosis in breast, ovarian, and prostate cancer. Coincidentally, increased TAMs (tumor-associated macrophages) density also designates poor prognostic value, suggesting that CSF1-CSF1R axis may have an important role towards activity of TAMs.[iv, v, vi]

The CSF1/CSF1R signalling pathway is targeted in the treatment against numerous malignancies, including breast, leukaemia, and glioblastoma. Studies have demonstrated that TAMs undergo turnover in a CSF-1R dependent manner, with continuous inhibition of the CSF-1R pathway being essential for depletion of TAMs and serving as an anticancer therapy. Therefore, the immunosuppressive tumor environment mediated by CSF-1 helps tumor cells escape killing by immune cells and assists them to metastasize. Since CSF-1R regulates the functioning of macrophages impacting tumor progression, inhibiting the CSF-1R pathway has emerged as a major therapeutic goal in cancer. Recently, some of the CSF-1R inhibitors had shown promising results in terms of potency, selectivity and bioavailability of cFMS kinase activity.[vii]

Among them, one of the well-known inhibitor which is in the clinical phase trials is BLZ-945. Although high in potency, this inhibitor fail to achieve a sustained inhibition of CSF-1R and are associated with toxicity to normal cells. Accordingly, there remains an urgent need for CSF-1R inhibitors with an improved activity profile while exhibiting decreased toxicity.

SUMMARY

The present invention describes prodrugs of BLZ-945 which can assemble into supramolecular structure with improved pharmacokinetic profile such as long circulation time, enhance uptake and slow release of drug inside tumor. The BLZ-945 uptake to tumor can be achieved in higher amount by making supramolecular assemblies along with addition of some co-lipid to form nanoparticles with average particle size below 400 nm. Degradation of the supramolecular assembly as well as the prodrug releases effective drug inside the cell. Pharmaceutical compositions of prodrug of a BLZ-945 comprise a linker wherein BLZ-945 is coupled through ester, ether, amide, or other covalent conjugation with the linker. The lipid molecule can be cholesterol, oleic acid, alpha tocopherol, fatty acid or other naturally occurring lipid molecule which is conjugated to drug molecule through a suitable linker/spacer. The spacer can be composed of aliphatic dicarboxylic acid, unsaturated dicarboxylic acid, aldaric acid, fumaric acid, propargylic acid, acetylene dicarboxylic acid, aromatic/hetero aromatic dicarboxylic acid, ethylene glycol, diethylene glycol, natural or unnatural amino acids individually or in any combination.

The present disclosure thus provides a compound of BLZ-945—Lipid conjugate of Formula I

Formula I wherein, 'Xa' is

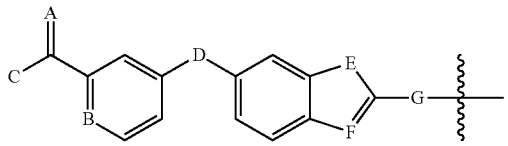

C=hydroxy, alkyl group, aryl group, cycloalkyl group
A=H, O, NH, S
B=CH, N
D=C, O, NH, S
E=C, O, NH, S
F=CH, N
G=C, O, NH, S 'Xb' is

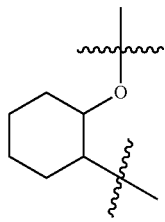 [SMILES: *OC1CCCCC1*]

'Z' is a linker joining 'Xb' with 'L'; and
'L' is a lipid, a lipid derivative or a lipid conjugate or any combination thereof; or
any derivative, tautomeric form, isomer, polymorph, solvate, or intermediates of compound of formula I thereof.

The disclosure provides a supramolecular combinatorial therapeutic (SCT). The disclosure also provides compositions, e.g., pharmaceutical compositions comprising the supramolecular combinatorial therapeutic. As used herein, the term "supramolecular combinatorial therapeutic" or "SCT" refers to nano- or micro-sized structures in which, or on which, the active agents to be delivered are not covalently (or otherwise chemically) bound, but are instead physically or mechanically contained within or retained by the structure. These structures can be stabilized by van der Waals forces or other forms of noncovalent bonding. The supramolecular combinatorial therapeutic can be, but are not limited to, in the form of particles, liposomes, micelles, emulsions. In some embodiments, the supramolecular combinatorial therapeutic is in the form of a nano- or microparticle. In some embodiments, the supramolecular combinatorial therapeutic is in the form of a particle, wherein particle has a lipid layer forming a lumen, wherein a BLZ-945 conjugate is present in or is on the outer surface of the lipid layer.

Certain exemplary embodiments provide supramolecular combinatorial therapeutics, wherein a BLZ-945-lipid conjugate is combined with one or more of a kinase inhibitor, a chemotherapeutic agent and an immunoregulator, each of which is optionally conjugated with a lipid.

The present disclosure also provides a composition comprising the BLZ-945-lipid conjugate and pharmaceutically acceptable excipients.

In an aspect, described herein is a method for inhibition of CSF or CSF-1R signalling pathway in a cell, by contacting the cell with the BLZ-945-lipid conjugate or composition or formulation of the present disclosure.

In another aspect, described herein is a method of treating cancer, comprising, administering a supramolecular combinatorial therapeutic as described herein to a patient in need of treatment for cancer. In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer. In some embodiments, the method further comprises co-administering one or more additional anti-cancer therapy to the patient. In some embodiments, the additional therapy is selected from the group consisting of: surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient.

The present disclosure also provides processes to arrive at BLZ-945-lipid conjugates described herein.

The present disclosure also provides formulations of the BLZ-945-lipid conjugate along with phospholipid or PEGylated phospholipid or a combination thereof.

BRIEF DESCRIPTION OF THE DRAWINGS

In order that the invention may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure.

FIG. 2. (a) Expression of phospho-CSF1R in RAW264.7 cells at different time points post-treatment with mCSF. (b-c) Treatment with either BLZ-945 (a current gold standard small molecule inhibitor of CSF1R) or AK750 (the formulated form of BLN101) across different time points followed by CSF-1 (10 ng/mL) stimulation for 20 minutes. After stimulation the cells were washed with cold PBS and the cell lysates were collected. The inhibitory effect on CSF1R was detected using Western blot (d) Graph shows the quantification of the CSF-1R phosphorylation.

FIG. 3. BLN101 (in formulation AK750) exerts a sustained and enhanced increase in iNOS expression, indicative of M1 lineage. (a) treatment with AK750 results in elevated intracellular concentrations at later time points as opposed to a BLZ945, when cells are treated with equimolar concentrations of both drugs. The amount of drug internalized was quantified by UV-vis spectroscopy. Data shown are mean±SEM from at least 3 replicates; *p<0.05; **p<0.01. (b) Treatment with B16/F10 tumor conditioned media activated CSF1R signaling (phosphorylation of receptor) in macrophages over time. Treatment of macrophages with BLN101 (as AK750 formulation) exerts a sustained inhibition of CSF1R activation as see with with Western blotting. (c) Treatment with TCM also decreases the expression of iNOS in the macrophages as detected using Western blotting. (d) The cells were treated with TCM for 24 hours, followed by which the TCM was replaced with DMEM basal media and the TCM treated cells were exposed to BLZ-945 or BLN101 (in AK750 formulation) and cell lysates were collected at 5 min, 1 hour, 6 hours and 24 hours respectively. Western blotting reveals that treatment with AK750 has a greater effect than BLZ945 in activating iNOS expression in the macrophages. e) Graph showing the quantification of iNOS levels.

FIG. 7. Effect of BLN101 on breast tumor growth inhibition. To validate the therapeutic efficacy of BLN101 (as AK750 formulation), we randomly sorted mice bearing 4T1 breast cancer into four groups and treated each group with one of the following: blank vehicle (control); AK750; an antiCSF1 antibody, and BLZ945. Treatment was strated when the tumors reached ~75 mm³ in volume. The day of first injection is considered Day 0). Vehicle-treated animals formed large tumors by Day 12, and consequently were killed. The animals in the other groups were also killed at the same time point to evaluate the effect of the treatments on tumor pathology. (a) Graph shows that while treatment with BLZ945 decreased tumor growth compared with vehicle-treated animals, treatment with AK750 resulted in complete inhibition of tumor growth. (b) Changes in body weight were within the acceptable limits. (c) Graph shows the number of metastatic nodules in lungs in different treatment groups. (d) Kaplan Meir Graph shows the effect of treatments on survival (e) Quantitative analysis of the tumor-associated macrophages (TAMs) using FACS revealed that treatment with AK750 significantly reduced M2 macrophage markers (CCD206) and increased the M1 pool (MHCII+, CD86+), which could mechanistically explain the in vivo efficacy.

FIG. 8. Effect of combination of BLN101 and anti-SIRPα antibody formulated in a single formulation. An anti-SIRPα antibody conjugated to a building block can assemble with BLN101 into a stable supramolecular structure. We term this supramolecular formulation as anti-SIRPα-AK750. (a) A representative FACS shows the improved binding of the anti-SIRPα-AK750 to macrophages as opposed to nonspecific binding. (b) Graphs show the quantification of binding of labeled anti-SIRPα-AK750 to macrophages. (c) We randomly sorted mice bearing B16/F10 melanoma into four groups and treated each group with a single dose of one of the following: blank vehicle (control); AK750; an antiSIRPα antibody, and anti-SIRPα-AK750. Treatment was started when the tumors reached ~75 mm³ in volume. The day of first injection is considered Day 0). Vehicle-treated animals formed large tumors by Day 10, and consequently were killed. The animals in the other groups were also killed at the same time point to evaluate the effect of the treatments on tumor pathology. (c) Graph shows that the effect of treatments on tumor growth. indicating that the combinatorial approach results in a synergistic outcome.

DETAILED DESCRIPTION

Figure 1A:
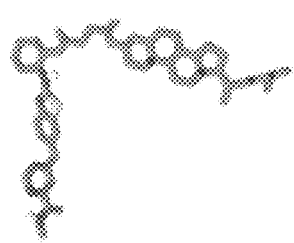
FIG. 1. (a) The quantum mechanical energy minimized structure of BLN01. (b) An all atomistic simulation of a lipid bilayer containing 20 mol % of BLN101 revealed the formation of a stable supramolecular structure, termed AK750. (c) Analysis of the deuterium order parameter, i.e. ordering of the lipid tail, as a measure of stability, revealed that the amphiphile resulted in a lipid tail ordering like that of a pure lipid-only bilayer. Furthermore, we measured ripple formation as a second measure of instability, which was quantified as the 'tilt' angle between vector joining center of mass of phospholipid tails and Z-axis (axis perpendicular to bilayer plane). A tilt angle of 0° is achieved means no ripples form, and a broad distribution indicates a large tilt angle and high bilayer instability. (d) The AK750 bilayer showed a narrow distribution around a tilt angle of 0°, which further validated the stability. (e) A representative high resolution Cryo-TEM image of BLN101 lipid nanoparticles fabricated with co-lipids (PC and DSPE-PEG. (f) dynamic laser scattering shows the narrow size distribution of the nanoparticles with a hydrodynamic radii of 100-200 nm.

The present disclosure is addressed to the needs of the art and provides for BLZ-945-lipid conjugates for treating cancer with a sustained inhibition of CSF/CSF-1R signalling pathway efficiently along with decreased toxicity.

The present disclosure thus relates to a compound of Formula I

Formula I wherein, 'Xa' is

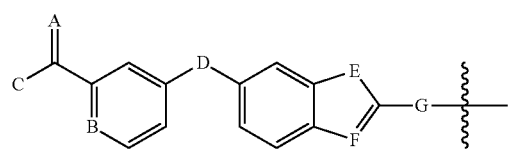

C=hydroxy, alkyl group, aryl group, cycloalkyl group

A=H, O, NH, S
B=CH, N
D=C, O, NH, S
E=C, O, NH, S
F=CH, N
G=C, O, NH, S
'Xb' is

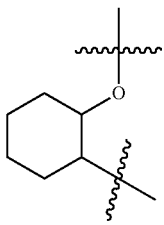

'Z' is a linker joining 'Xb' with 'L';
'L' is a lipid, a lipid derivative or a lipid conjugate or any combination thereof.

In a non-limiting embodiment, the present disclosure also encompasses any derivative, salt, tautomeric form, isomer, polymorph, solvate, or intermediates of compound of formula I thereof.

In a non-limiting embodiment, the linker group(s) in the compound(s) of Formula I of the present disclosure is selected from a group comprising a direct bond or an atom such as oxygen or sulfur, a unit such as $NR^1$, C(O), C(O)O, $C(O)NR^1$, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylherocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In another non-limiting embodiment, the linker group(s) in the compound(s) of Formula I of the present disclosure is selected from a group comprising a direct bond, ester, ether, amide or any functional group containing covalent linker.

In yet another non-limiting embodiment, the linker group(s) in the compound(s) of Formula I of the present disclosure is selected from a group comprising one or more of succinic acid, fumaric acid, propargylic acid, ethylene glycol, diethylene glycol, and natural or unnatural amino acids.

In still another non-limiting embodiment, the linker group(s) in the compound(s) of Formula I of the present disclosure is selected from a group comprising at least one of oxalic acid, malonic acid, glutaric acid, ethylene diamine, ethylene glycol, diethylene glycol, acetic acid, propionic acid, butyric acid, valeric acid, acrylic acid, but-2-enoic acid, pent-2-enoic acid, hex-2-enoic acid, 2-propynoic acid, but-2-ynoic acid, pent-2-ynoic acid, hex-2-ynoic acid, ethylene, propylene, 1-butene, 1-pentene, 1-hexene, acetylene, propyne, but-1-yne, pent-1-yne, and any combinations thereof.

In still another non-limiting embodiment, the linker group(s) in the compound(s) of Formula I of the present disclosure is selected from a group comprising C(O) $CH_2CH_2C(O)$—; —$C(O)(CH_2CH_2)_mC(O)(OCH_2CH_2)_n$—, wherein 'n' is 1 to 10 and 'm' is 1 to 4; —$C(O)(CH_2)_xCH_2C(O)NH(CH_2CH_2)_n$—, wherein 'n' is 1 to 10 and 'x' is 0 to 3; —$C(O)(CH_2)_mCH_2C(O)NH(CH_2CH_2)_nNHC(O)$—, wherein 'n' is 1 to 10 and 'm' is 1 to 4; —$C(O)CH_2(CH_2)_mC(O)NH$—, wherein 'm' is 1 to 4; —$C(O)(CH_2)_nCH_2(R)NHC(O)$—, wherein 'n' is 1 to 10 and R is H, alkyl, acid, amine, aryl, or thiol; —$C(O)(CH_2)_nCH_2(R)NHC(O)$—, wherein 'n' is 1 to 10 and R is H, alkyl, acid, amine, aryl or thiol; $C(O)(CH_2(R)CH_2)_nC(Y)X$—, wherein 'n' is 1 to 10, R is H, alkyl, acid, amine, aryl or thiol, Y is C, O, NH, S, and X is C, O, NH, S; $C(O)CH_2CH_2NHC(O)$—; —$C(O)CH_2CH_2C(O)NHCH_2CH_2NHC(O)$—; —$C(O)CH_2CH_2C(O)NHCH_2NHC(O)$—; —$C(O)CH_2OCH_2CH_2$—; —$C(O)CH_2CH_2OCH_2CH_2$—; —$C(O)CH_2OCH_2CH_2OCH_2CH_2$—; —$C(O)CH(R)NHC(O)CH_2$—, wherein R is H, $CH_3$, $CH(CH_3)_2$, $CH_2CH(CH_3)_2$, $C(CH_3)CH_2CH_3$, or $CH_2$-Phenyl; —$C(O)CH(R)NHC(O)CH_2CH_2$—, wherein R is H, $CH_3$, $CH(CH_3)_2$, $CH_2CH(CH_3)_2$, $C(CH_3)CH_2CH_3$, or $CH_2$-Phenyl; —$C(O)CH(R)NHC(O)(CH_2)_nC(O)$—, wherein R is H, $CH_3$, $CH(CH_3)_2$, $CH_2CH(CH_3)_2$, $C(CH_3)CH_2CH_3$, or $CH_2$-Phenyl, and n is 1, 2, or 3; —$C(O)CH(R)NHC(O)CH_2OCH_2CH_2$—, wherein R is H, $CH_3$, $CH(CH_3)_2$, $CH_2CH(CH_3)_2$, $C(CH_3)CH_2CH_3$, or $CH_2$-Phenyl; —$C(O)C≡C(CH_2)_n$—$C(O)$—, wherein n is 1, 2 or 3; —$C(O)C≡C(CH_2)_n$—, wherein n is 0, 1, or 2; —$C(O)CH=CH(CH_2)_nC(O)$—, wherein n is 0, 1, 2, or 3; —$C(O)CH=CH(CH_2)_n$—, wherein n is 1, 2, or 3; and —$C(O)CH_2CH_2C(O)NHCH_2C(O)$—.

In a non-limiting embodiment, the lipid(s) in the compound(s) of Formula I of the present disclosure is selected from a group comprising cholesterol, cholesterol derivatives, oleic acid, oleic acid derivative, alpha tocopherol, alpha tocopherol derivatives, phospholipid, phospholipid derivatives, fatty acid, naturally occurring lipid molecule which is conjugated to drug molecules, 1,3-Propanediol Dicaprylate/Dicaprate, 10-undecenoic acid, I-dotriacontanol, 1-heptacosanol, 1-nonacosanol, 2-ethyl hexanol, Androstanes, Arachidic acid, Arachidonic acid, arachidyl alcohol, Behenic acid, behenyl alcohol, Capmul MCM C10, Capric acid, capric alcohol, capryl alcohol, Caprylic acid, Caprylic/Capric Acid Ester of Saturated Fatty Alcohol C12-C18, Caprylic/Capric Triglyceride, Caprylic/Capric Triglyceride, Ceramide phosphorylcholine (Sphingomyelin, SPH), Ceramide phosphorylethanolamine (Sphingomyelin, Cer-PE), Ceramide phosphorylglycerol, Ceroplastic acid, Cerotic acid, Cerotic acid, ceryl alcohol, Cetearyl alcohol, Ceteth-10, cetyl alcohol, Cholanes, Cholestanes, cholesterol, cis-11-eicosenoic acid, cis-11-octadecenoic acid, cis-13-docosenoic acid, cluytyl alcohol, Dihomo-γ-linolenic, Docosahexaenoic acid, egg lecithin, Eicosapentaenoic acid, Eicosenoic acid, Elaidic acid, elaidolinolenyl alcohol, elaidolinoleyl alcohol, elaidyl alcohol, Erucic acid, erucyl alcohol, Estranes, Ethylene glycol distearate (EGDS), Geddic acid, geddyl alcohol, glycerol distearate (type I) EP (Precirol ATO 5), Glycerol Tricaprylate/Caprate; Glycerol Tricaprylate/Caprate (CAPTEX® 355 EP/NF); glyceryl monocaprylate (Capmul MCM C8 EP), Glyceryl Triacetate, Glyceryl Tricaprylate, Glyceryl Tricaprylate/Caprate/Laurate, Glyceryl Tricaprylate/Tricaprate, glyceryl tripalmitate (Tripalmitin), Henatriacontylic acid, Heneicosyl alcohol, Heneicosylic acid, Heptacosylic acid, Heptadecanoic acid, Heptadecyl alcohol, Hexatriacontylic acid, isostearic acid, isostearyl alcohol, Lacceroic acid, Lauric acid, Lauryl alcohol, Lignoceric acid, lignoceryl alcohol, Linoelaidic acid, Linoleic acid, linolenyl alcohol, linoleyl alcohol, Margaric acid, Mead, Melissic acid, melissyl alcohol, Montanic acid, montanyl alcohol, myricyl alcohol, Myristic acid, Myristoleic acid, Myristyl alcohol, neodecanoic acid, neoheptanoic acid, neononanoic acid, Nervonic, Nonacosylic acid, Nonadecyl alcohol, Nonadecylic acid, Nonadecylic acid, Oleic acid, oleyl alcohol, Palmitic acid, Palmitoleic acid, palmitoleyl alcohol, Pelargonic acid, pelargonic alcohol, Pentacosylic acid, Pentadecyl alcohol, Pentadecylic acid, Phosphatidic acid (phosphatidate, PA), Phosphatidylcholine (lecithin, PC), Phosphatidylethanolamine (cephalin, PE), Phosphatidylinositol (PI), Phosphatidylinositol bisphosphate (PIP2), Phosphatidylinositol phosphate (PIP), Phosphatidylinositol triphosphate (PIP3), Phosphatidylserine (PS), polyglyceryl-6-distearate, Pregnanes, Propylene Glycol Dicaprate, Propylene Glycol Dicaprylocaprate, Propylene Glycol Dicaprylocaprate, Psyllic acid, recinoleaic acid, recinoleyl alcohol, Sapienic acid, soy lecithin, Stearic acid, Stearidonic, stearyl alcohol, Tricosylic acid, Tridecyl alcohol, Tridecylic acid, Triolein, Undecyl alcohol, undecylenic acid, Undecylic acid, Vaccenic acid, α-Linolenic acid, and γ-Linolenic acid via a spacer, wherein the spacer is selected from a group comprising aliphatic dicarboxylic acid, unsaturated dicarboxylic acid, aldaric acid, fumaric acid, propargylic acid, acetylene dicarboxylic acid, aromatic/hetero aromatic dicarboxylic acid, ethylene glycol, diethylene glycol, natural or unnatural amino acids, or their derivatives individually or in any combination thereof.

In another non-limiting embodiment, the lipid(s) or lipid derivative(s) in the compound(s) of Formula I of the present disclosure is selected from a group comprising cholesterol, cholesterol derivatives, oleic acid, oleic acid derivative, alpha tocopherol, alpha tocopherol derivatives, phospholipid, phospholipid derivatives, fatty acid or naturally occurring lipid molecule; which is conjugated to drug molecules via a spacer, wherein the spacer is selected from a group comprising aliphatic dicarboxylic acid, unsaturated dicarboxylic acid, aldaric acid, fumaric acid, propargylic acid, acetylene dicarboxylic acid, aromatic/hetero aromatic dicarboxylic acid, ethylene glycol, diethylene glycol, natural or unnatural amino acids, or their derivatives individually or any combination thereof.

In a non-limiting embodiment, the lipid conjugate(s) in the compound(s) of Formula I is the lipid or the lipid derivative conjugated with a compound selected from a group comprising a kinase inhibitor, CSF-1R inhibitor, a chemotherapeutic drug, an immunomodulator or an antibody or any combination thereof.

In a non-limiting embodiment of the present disclosure, the compound of Formula I is BLZ-945-lipid conjugate(s).

Generally, the supramolecular combinatorial therapeutic of the present disclosure comprises a BLZ-945-lipid conjugate. It is to be recognized that the supramolecular combinatorial therapeutic can comprise only one type of BLZ-945 conjugate or two or more different types of BLZ-945 conjugates. Accordingly, in some embodiments, the supramolecular combinatorial therapeutic comprises only one type of BLZ-945 conjugate. In some other embodiments, the supramolecular combinatorial therapeutic comprises at least two (e.g., two, three, four, five, six, seven, eight, nine, ten or more) different types of BLZ-945 conjugates. By different types of BLZ-945 conjugates is meant that at least one element in the conjugates differs from each other. For example, the different types of conjugates can differ by the specific BLZ-945 in the conjugates, the specific lipids in the conjugates, or the way the BLZ-945 and the lipid are conjugated together, i.e., through a linker.

In addition to the BLZ-945 conjugate, supramolecular combinatorial therapeutic can further comprise a lipid conjugated kinase inhibitor. Thus, in some embodiments, the supramolecular combinatorial therapeutic comprises a BLZ-945-lipid conjugate and a kinase inhibitor-conjugate. The supramolecular combinatorial therapeutic comprising the BLZ-945 conjugate and the kinase inhibitor conjugate can have the conjugates in any desired combination or ratio. For example, the supramolecular combinatorial therapeutic can comprise two or more (e.g. two, three, four, five, six, seven, eight, nine, ten or more) different types of BLZ-945 conjugates and one type of kinase inhibitor conjugate. In some other examples, the supramolecular combinatorial therapeutic can comprise one type of BLZ-945 conjugate and two or more (e.g. two, three, four, five, six, seven, eight, nine, ten or more) different types of kinase inhibitor conjugates. In still in some other examples, the supramolecular combinatorial therapeutic can comprise two or more (e.g. two, three, four, five, six, seven, eight, nine, ten or more) different types of BLZ-945 conjugates and two or more (e.g. two, three, four, five, six, seven, eight, nine, ten or more) different types of kinase inhibitor conjugates. In certain exemplary embodiments, the kinase inhibitor is a CSF-1R or FMS tyrosine kinase inhibitors, The inhibitors include but is not limited to, compounds which target, decrease or inhibit the activity of Colony stimulating factor 1 receptor (CSF-1R). e.g., AC710, ARRY-382, AZD6495, BLZ945, CC-223, cediranib, cerdulatinib, crenolanib, dovitinib, GTP-14564, GW-2580, JNJ-28312141, JNJ-40346527, Ki-20227, linifanib, OSI-930, pazopanib, pexidartinib, quizartinib, tandutinib, TG02, etc. In still some other embodiments, the supramolecular combinatorial therapeutic can comprise two or more (e.g. two, three, four, five, six, seven, eight, nine, ten or more) different types of chemotherapeutic agents, two or more (e.g. two, three, four, five, six, seven, eight, nine, ten or more) different types of BLZ-945 conjugates, and two or more (e.g. two, three, four, five, six, seven, eight, nine, ten or more) different types of kinase inhibitor conjugates. In some embodiments, the supramolecular combinatorial therapeutic further comprises an antibody (or an antigen binding fragment thereof), optionally conjugated with a lipid.

In some embodiments, the supramolecular combinatorial therapeutic further comprises an antibody (or an antigen binding fragment thereof) conjugated with a lipid. Without limitations, the antibody can be useful for therapeutic purposes (i.e., a therapeutic antibody) or for targeting the supramolecular combinatorial therapeutic to a desired site (i.e., a targeting antibody). In some embodiments, the targeting ligand binds a protein, receptor, or marker expressed on the surface of a cancer cell. Targeting ligands that preferentially bind to and/or cross the membrane of cancer cells are known in the art, e.g. iRGD, RGD, Lyp-1 peptide (CGNKRTRGC), NGR peptide, iNGR, RGR peptide, CAR peptide, tCAR peptide (CARSKNK); FSH-33, Allatostatin 1, the pentapeptide CREKA, Hepatocarcinoma targeting peptide, Peptide GFE, anti-EGFR antibodies and/or antibody fragments, in particular Cetuximab, CendR, iRGD peptide (RGD-CendR hybrid peptide), small molecules, antibodies and/or antibody fragments binding to cancer-specific epitopes like e.g. CEA, Gastrin-releasing peptide receptors, Somatostatin receptors, Galanin receptors, Follicle-stimulating hormone receptors, p32 protein, Fibroblast growth factor receptors, HepG2, Epidermal growth factor receptors, Integrin αvβ6, Neuropilin-1 receptor and VEGF receptors and variants or combinations thereof. In some embodiments, a targeting agent can be iRGD, e.g. a peptide having the sequence CRGDKGPDC. In some embodiments, the targeting ligand binds EGFR. In some embodiments, the targeting ligand is a polyclonal or monoclonal antibody or a fragment thereof retaining epitope binding activity or an antibody-based binding moiety. In some embodiments, the targeting ligand is a polyclonal or monoclonal antibody, antibody fragments, a peptide, or a molecule that is capable of binding protein receptors expressed on the surface of cancer cells. In some embodiments, the targeting ligand is an antibody selected from the group consisting of C242 antibody (CanAg), Rituximab (CD20), Trastuzumab (Her2), Cetuximab (EGFR), Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope bind fragments thereof and any combinations thereof.

In some embodiments, the supramolecular combinatorial therapeutic further comprises an antibody (or an antigen binding fragment thereof) conjugated with a lipid. Without limitations, the antibody can be useful for therapeutic purposes (i.e., a therapeutic antibody) or for targeting the supramolecular combinatorial therapeutic to a desired site (i.e., a targeting antibody).

In some embodiments, the supramolecular combinatorial therapeutic further comprises an immunomodulator. Immunomodulators are active agents of immunotherapy, and can either activate or suppress an immune response. In certain embodiments, the immunomodulator activates and stimulates an immune response against cancer cells, non-limiting examples of which include immune cells (e.g., natural killer cells, lymphokine-activated killer cells, cytotoxic T cells and dendritic cells), antibodies (e.g., anti-PD-L1 and anti-PD-1 antibodies, anti-CD52, anti-VEGF-A, anti-CD30, anti-EGFR, anti-CD33, anti-CD20, anti-CTLA4, and anti-HER-2 antibodies), and cytokines (e.g., interferons and interleukins). In certain exemplary embodiments, the immunomodulator is conjugated with a lipid.

In another aspect, described herein is a method of treating cancer, comprising, administering a supramolecular combinatorial therapeutic as described herein to a patient in need of treatment for cancer. In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

In some embodiments, the method further comprises co-administering one or more additional anti-cancer therapy to the patient. In some embodiments, the additional therapy is selected from the group consisting of surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient. In some embodiments, the method further comprises co-administration of one or more immunomodulators to the subject.

The BLZ-945 uptake to tumor can be achieved in higher amounts by supramolecular assembly along with addition of some co-lipid to form nanoparticles with average particle size below 200 nm. Degradation of supramolecular assembly as well as the prodrug releases effective drug inside cells. Pharmaceutical composition of prodrug of a BLZ-945 comprises a linker wherein BLZ-945 is coupled through ester, ether, amide or other covalent conjugation with the linker. The lipid molecule can be cholesterol, oleic acid, alpha tocopherol, fatty acid or another naturally occurring lipid molecule which is conjugated to drug molecule through a suitable linker/spacer. The spacer can be composed of aliphatic dicarboxylic acid, unsaturated dicarboxylic acid, aldaric acid, fumaric acid, propargylic acid, acetylene dicarboxylic acid, aromatic/hetero aromatic dicarboxylic acid, ethylene glycol, diethylene glycol, natural or unnatural amino acids individually or in any combinations.

In another aspect, described herein is a method of treating allergy, comprising, administering a supramolecular combinatorial therapeutic as described herein to a patient in need of treatment for allergy.

In another aspect, described herein is a method of treating Systemic lupus erythematosus (SLE), comprising, administering a supramolecular combinatorial therapeutic as described herein to a patient in need of treatment for Systemic lupus erythematosus.

In another aspect, described herein is a method of treating nephritis, comprising, administering a supramolecular combinatorial therapeutic as described herein to a patient in need of treatment for nephritis.

In another aspect, described herein is a method of treating Chronic Obstructive Pulmonary Disease (COPD), comprising, administering a supramolecular combinatorial therapeutic as described herein to a patient in need of treatment for COPD.

In another aspect, described herein is a method of treating abnormal macrophage functions, comprising, administering a supramolecular combinatorial therapeutic as described herein to a patient in need of treatment for abnormal macrophage functions.

In some embodiments, the supramolecular combinatorial therapeutic is in the form of a particle, wherein the particle has a lipid layer forming a lumen, wherein a BLZ-945 conjugate is present in or on the outer surface of the lipid layer.

In one aspect, the disclosure provides a supramolecular combinatorial therapeutic comprising a BLZ-945 conjugate. Amount of the conjugate in the supramolecular combinatorial therapeutic can range from about 1% to about 99% (w/w). For example, the amount of the conjugate in the supramolecular combinatorial therapeutic can be from about 5% to about 95%, from about 10% to about 90%, from about 15% to about 85%, from about 20% to about 75%, or from about 25% to about 50%.

In some embodiments, the composition can comprise two or more (e.g., two, three, four, five, six, seven, eight, nine, ten or more) different BLZ-945 conjugates. The different conjugates can be present in any desired ratio. For example, the different conjugates can be in a ratio ranging from about 100:1 to 1:100. In some embodiments, the different conjugates can be in a ratio ranging from about 50:1 to 1:50, 25:1 to 1:25, 10:1 to 1:10, 5:1 to 1:5, or 2.5:1 to 1:2.5. In some embodiments, the different conjugates can be in a ratio of about 1:1.

Without limitations, the supramolecular combinatorial therapeutic can be in any shape, size or form. For example, the supramolecular combinatorial therapeutic can be in the form of a nano- or micro-structure. Such structures can include, but are not limited to liposome, emulsions, and micelles. In some embodiments, the supramolecular combinatorial therapeutic can be in the form of a liposome. As used herein, the term "liposome" encompasses any compartment enclosed by a lipid layer. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 m. Oligolamellar large vesicles and multilamellar vesicles have multiple, usually concentric, membrane layers and are typically larger than 0.1 m. Liposomes with several nonconcentric membranes, i.e., several smaller vesicles contained within a larger vesicle, are termed multivesicular vesicles.

In some embodiments, a lipid conjugated component of the supramolecular combinatorial therapeutic is present in or on the surface of the lipid layer. In some embodiments, the supramolecular combinatorial therapeutic is in the form of a liposome, wherein the non-lipid portion of a lipid conjugated component (e.g., BLZ-945, kinase inhibitor, chemotherapeutic agent, immunomodulator, or antibody portion of the conjugate) is on the outer surface of the lipid layer.

The supramolecular combinatorial therapeutic can also be in the form of an emulsion which may be of either the water-in-oil (w/o) or the oil-in-water (o/w) variety. Pharmaceutical excipients such as emulsifiers, stabilizers, dyes, preservatives, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

The supramolecular combinatorial therapeutic can be in the form of a particle. As used herein, the term "particle" encompasses liposomes, emulsions, vesicles and lipid particles. Generally, the particle can be of any shape or form, e.g., spherical, rod, elliptical, cylindrical, capsule, or disc; and these particles can be part of a network or an aggregate. Without limitations, the particle can have any size from nm to millimeters. In some embodiments, the particle is a microparticle or a nanoparticle. As used herein, the term "microparticle" refers to a particle having a particle size of about 1 µm to about 1000 µm. As used herein, the term "nanoparticle" refers to particle having a particle size of about 0.1 nm to about 1000 nm. Generally, the particles disclosed herein are nanoparticles and have an average diameter of from about 5 nm to about 500 nm. In some embodiments, the particles have an average diameter of from about 75 nm to about 500 nm, from about 25 nm to about 250 nm, from about 50 nm to about 150 nm, from about 75 nm to about 125 nm, from about 50 nm to about 500 nm, from about 75 nm to about 200 nm, from about 100 to about 175 nm, from about 125 nm to about 175 nm, from about 40 nm to about 90 nm, or from about 50 nm to about 80 nm.

In some embodiments a nanoparticle can be less than about 1 um in diameter, e.g., about 1 um or less in diameter, about 500 nm or less in diameter, about 400 nm or less in diameter, about 300 nm or less in diameter, about 200 nm or less in diameter, about 100 nm or less in diameter, about 50 nm or less in diameter, or about 10 nm or less in diameter. In some embodiments a nanoparticle can be less than 1 um in diameter, e.g., 1 um or less in diameter, 500 nm or less in diameter, 400 nm or less in diameter, 300 nm or less in diameter, 200 nm or less in diameter, 100 nm or less in diameter, 50 nm or less in diameter, or 10 nm or less in diameter. In some embodiments, the nanoparticles in a composition can be from about 1 nm to about 1 um in diameter, e.g. from about 1 nm to about 500 nm in diameter, from about 1 nm to about 200 nm in diameter, from about 10 nm to about 200 nm in diameter, from about 100 nm to about 200 nm in diameter, or from about 10 nm to about 100 nm in diameter. In some embodiments, the nanoparticles in a composition can be from 1 nm to 1 um in diameter, e.g. from 1 nm to 500 nm in diameter, from 1 nm to 200 nm in diameter, from 10 nm to 200 nm in diameter, from 100 nm to 200 nm in diameter, or from 10 nm to 100 nm in diameter.

In some embodiments, nanoparticles can be selected to be of specific sizes, e.g. less than about 200 nm in diameter. Methods of selecting nanoparticles of a particular size and/or range of sizes are known in the art and can include, by way of non-limiting example, filtration, sedimentation, centrifugation, and/or chromatographic methods, e.g. SEC.

In addition to a BLZ-945 conjugate, the supramolecular combinatorial therapeutic can further include one or more additional lipids and/or other components. Without wishing to be bound by a theory, other lipids can be included in the supramolecular combinatorial therapeutic for a variety of purposes, such as to prevent lipid oxidation, to stabilize bilayer, to reduce aggregation during formation or to attach ligands onto the particle surface. Any of a number of lipids can be present, including but not limited to, amphipathic, neutral, cationic, anionic lipids, sterols, and phospholipids. Further, such lipids can be used alone or in any combination with each other. In some embodiments, the supramolecular combinatorial therapeutic further comprises a lipoprotein particle, e.g., HDL or LDL. The supramolecular combinatorial therapeutic can comprise from about 1% to about 99% (w/w) of the additional lipid or component. Further the additional lipid or component can be present in 10:1 to 1:10 ratio with the conjugate. If two or more different additional lipids are present in the supramolecular combinatorial therapeutic, each lipid can be independently in 10:1 to 1:10 ratio with the conjugate. Further, if two or more different additional lipids are present in the supramolecular combinatorial therapeutic, the two lipids can be in 10:1 to 1:10 ratio. Without limitations, two different components (conjugate and lipid or two different lipids) of the supramolecular combinatorial therapeutic can be in ratio 10:1 to 1:10, 5:1 to 1:5, or 2.5:1 to 1:2.5. In some embodiments, two different components in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. If the supramolecular combinatorial therapeutic comprises more than two components ratio between any two components can be independent of ratio between any other two components.

The term "lipid" as used herein means a substance that is soluble in organic solvents and includes, but is not limited to, oils, fats, sterols, triglycerides, fatty acids, phospholipids, and the like. Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of cholesterol, 1,3-Propanediol Dicaprylate/Dicaprate, 10-undecenoic acid, 1-dotriacontanol, 1-heptacosanol, 1-nonacosanol, 2-ethyl hexanol, Androstanes, Arachidic acid, Arachidonic acid, arachidyl alcohol, Behenic acid, behenyl alcohol, Capmul MCM C10, Capric acid, capric alcohol, capryl alcohol, Caprylic acid, Caprylic/Capric Acid Ester of Saturated Fatty Alcohol C12-C18, Caprylic/Capric Triglyceride, Caprylic/Capric Triglyceride, Ceramide phosphorylcholine (Sphingomyelin, SPH), Ceramide phosphorylethanolamine (Sphingomyelin, Cer-PE), Ceramide phosphorylglycerol, Ceroplastic acid, Cerotic acid, ceryl alcohol, Cetearyl alcohol, Ceteth-10, cetyl alcohol, Cholanes, Cholestanes, cholesterol, cis-11-eicosenoic acid, cis-11-octadecenoic acid, cis-13-docosenoic acid, cluytyl alcohol, Dihomo-γ-linolenic, Docosahexaenoic acid, egg lecithin, Eicosapentaenoic acid, Eicosenoic acid, Elaidic acid, elaidolinolenyl alcohol, elaidolinoleyl alcohol, elaidyl alcohol, Erucic acid, erucyl alcohol, Estranes, Ethylene glycol distearate (EGDS), Geddic acid, geddyl alcohol, glycerol distearate (type I) EP (Precirol ATO 5), Glycerol Tricaprylate/Caprate, Glycerol Tricaprylate/Caprate (CAPTEX®355 EP/NF), glyceryl monocaprylate (Capmul MCM C8 EP), Glyceryl Triacetate, Glyceryl Tricaprylate, Glyceryl Tricaprylate/Caprate/Laurate, Glyceryl Tricaprylate/Tricaprate, glyceryl tripalmitate (Tripalmitin), Henatriacontylic acid, Heneicosyl alcohol, Heneicosylic acid, Heptacosylic acid, Heptadecanoic acid, Heptadecyl alcohol, Hexatriacontylic acid, isostearic acid, isostearyl alcohol, Lacceroic acid, Lauric acid, Lauryl alcohol, Lignoceric acid, lignoceryl alcohol, Linoelaidic acid, Linoleic acid, linolenyl alcohol, linoleyl alcohol, Margaric acid, Mead, Melissic acid, melissyl alcohol, Montanic acid, montanyl alcohol, myricyl alcohol, Myristic acid, Myristoleic acid, Myristyl alcohol, neodecanoic acid, neoheptanoic acid, neononanoic acid, Nervonic, Nonacosylic acid, Nonadecyl alcohol, Nonadecylic acid, Nonadecylic acid, Oleic acid, oleyl alcohol, Palmitic acid, Palmitoleic acid, palmitoleyl alcohol, Pelargonic acid, pelargonic alcohol, Pentacosylic acid, Pentadecyl alcohol, Pentadecylic acid, Phosphatidic acid (phosphatidate, PA), Phosphatidylcholine (lecithin, PC), Phosphatidylethanolamine (cephalin, PE), Phosphatidylinositol (PI), Phosphatidylinositol bisphosphate (PIP2), Phosphatidylinositol phosphate (PIP), Phosphatidylinositol triphosphate (PIP3), Phosphatidylserine (PS), polyglyceryl-6-distearate, Pregnanes, Propylene Glycol Dicaprate, Propylene Glycol Dicaprylocaprate, Propylene Glycol Dicaprylocaprate, Psyllic acid, recinoleaic acid, recinoleyl alcohol, Sapienic acid, soy lecithin, Stearic acid, Stearidonic, stearyl alcohol, Tricosylic acid, Tridecyl alcohol, Tridecylic acid, Triolein, Undecyl alcohol, undecylenic acid, Undecylic acid, Vaccenic acid, α-Linolenic acid, and γ-Linolenic acid.

Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, P3,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof, and the like. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and β-acyloxyacids, can also be used.

In some embodiments, the phospholipid in the supramolecular combinatorial therapeutic is selected from the group consisting of 1,2-Didecanoyl-sn-glycero-3-phosphocholine, 1,2-Dierucoyl-sn-glycero-3-phosphate (Sodium Salt), 1,2-Dierucoyl-sn-glycero-3-phosphocholine, 1,2-Dierucoyl-sn-glycero-3-phosphoethanolamine, 1,2-Dierucoyl-sn-glycero-3[Phospho-rac-(1 1-glycerol) (Sodium Salt), 1,2-Dilinoleoyl-sn-glycero-3-phosphocholine, 1,2-Dilauroyl-sn-glycero-3-phosphate (Sodium Salt), 1,2-Dilauroyl-sn-glycero-3-phosphocholine, 1,2-Dilauroyl-sn-glycero-3-phosphoethanolamine, 1,2-Dilauroyl-sn-glycero-3[Phospho-rac-(1-glycerol) (Sodium Salt), 1,2-Dilauroyl-sn-glycero-3[Phospho-rac-(1-glycerol) (Ammonium Salt), 1,2-Dilauroyl-sn-glycero-3-phosphoserine (Sodium Salt), 1,2-Dimyristoyl-sn-glycero-3-phosphate (Sodium Salt), 1,2-Dimyristoyl-sn-glycero-3-phosphocholine, 1,2-Dimyristoyl-sn-glycero-3-phosphoethanolamine, 1,2-Dimyristoyl-sn-glycero-3[Phospho-rac-(1-glycerol) (Sodium Salt), 1,2-Dimyristoyl-sn-glycero-3[Phospho-rac-(1-glycerol) (Ammonium Salt), 1,2-Dimyristoyl-sn-glycero-3[Phospho-rac-(1-glycerol) (Sodium/Ammonium Salt), 1,2-Dimyristoyl-sn-glycero-3-phosphoserine (Sodium Salt), 1,2-Dioleoyl-sn-glycero-3-phosphate (Sodium Salt), 1,2-Dioleoyl-sn-glycero-3-phosphocholine, 1,2-Dioleoyl-sn-glycero-3-phosphoethanolamine, 1,2-Dioleoyl-sn-glycero-3 [Phospho-rac-(1-glycerol) (Sodium Salt), 1,2-Dioleoyl-sn-glycero-3-phosphoserine (Sodium Salt), 1,2-Dipalmitoyl-sn-glycero-3-phosphate (Sodium Salt), 1,2-Dipalmitoyl-sn-glycero-3-phosphocholine, 1,2-Dipalmitoyl-sn-glycero-3-phosphoethanolamine, 1,2-Dipalmitoyl-sn-glycero-3 [Phospho-rac-(1-glycerol) (Sodium Salt), 1,2-Dipalmitoyl-sn-glycero-3[Phospho-rac-(1-glycerol) (Ammonium Salt), 1,2-Dipalmitoyl-sn-glycero-3-phosphoserine (Sodium Salt), 1,2-Distearoyl-sn-glycero-3-phosphate (Sodium Salt), 1,2-Distearoyl-sn-glycero-3-phosphocholine, 1,2-Distearoyl-sn-glycero-3-phosphoethanolamine, 1,2-Distearoyl-sn-glycero-3[Phospho-rac-(1-glycerol) (Sodium Salt), 1,2-Distearoyl-sn-glycero-3[Phospho-rac-(1-glycerol) (Ammonium Salt), 1,2-Distearoyl-sn-glycero-3-phosphoserine (Sodium Salt), Egg-PC, Hydrogenated Egg PC, Hydrogenated Soy PC, 1-Myristoyl-sn-glycero-3-phosphocholine, 1-Palmitoyl-sn-glycero-3-phosphocholine, 1-Stearoyl-sn-glycero-3-phosphocholine, 1-Myristoyl-2-palmitoyl-sn-glycero 3-phosphocholine, 1-Myristoyl-2-stearoyl-sn-glycero-3-phosphocholine, 1-Palmitoyl-2-myristoyl-sn-glycero-3-phosphocholine, 1-Palmitoyl-2-oleoyl-sn-glycero-3-phosphocholine, 1-Palmitoyl-2-oleoyl-sn-glycero-3-phosphoethanolamine, l-Palmitoyl-2-oleoyl-sn-glycero-3[Phospho-rac-(1-glycerol)] (Sodium Salt), 1-Palmitoyl-2-stearoyl-sn-glycero-3-phosphocholine, 1-Stearoyl-2-myristoyl-sn-glycero-3-phosphocholine, 1-Stearoyl-2-oleoyl-sn-glycero-3-phosphocholine, and 1-Stearoyl-2-palmitoyl-sn-glycero-3-phosphocholine.

In some embodiments, the phospholipid is SPOC, egg PC, or Hydrogenated Soy PC (HSPC). In one, the phospholipid in the composition is SOPC.

In some embodiments, the supramolecular combinatorial therapeutic further comprises a targeting ligand. As used herein the term "targeting moiety" or "targeting ligand" refers to any molecule that provides an enhanced affinity for a selected target, e.g., a cell, cell type, tissue, organ, region of the body, or a compartment, e.g., a cellular, tissue or organ compartment. The targeting moiety or ligand can comprise a wide variety of entities. Such ligands can include naturally occurring molecules, or recombinant or synthetic molecules. Exemplary targeting ligands include, but are not limited to, antibodies (polyclonal or monoclonal), antigen binding fragments of antibodies, antigens, folates. EGFR, albumin, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Additional exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

In some embodiments, the targeting ligand is a polyclonal or monoclonal antibody or a fragment thereof retaining epitope binding activity or an antibody-based binding moiety.

In some embodiments, the targeting ligand is a polyclonal or monoclonal antibody, antibody fragments, a peptide, or a molecule that is capable of binding protein receptors expressed on the surface of cancer cells.

In some embodiments, the targeting ligand is an antibody selected from the group consisting of C242 antibody (CanAg), Rituximab (CD20), Trastuzumab (Her2), Cetuximab (EGFR), Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope bind fragments thereof and any combinations thereof.

In some embodiments, the composition of BLZ-945—lipid conjugate can further comprise a therapeutic agent in addition to the BLZ-945—lipid conjugate. Without limitations, when present in the supramolecular combinatorial therapeutic, the therapeutic agent can be encapsulated in the supramolecular combinatorial therapeutic; present in a lipid layer of the supramolecular combinatorial therapeutic; or present on the surface of the supramolecular combinatorial therapeutic.

As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agricultural, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof, including, for example, DNA nanoplexes.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies (polyconal and monoclonal) and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine,* 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index,* the complete contents of all of which are incorporated herein by reference.

The therapeutic agent can be linked to a component of the supramolecular combinatorial therapeutic. For example, the therapeutic agent can be linked to a lipid or phospholipid component of the supramolecular combinatorial therapeutic. The therapeutic agent and the component of the supramolecular combinatorial therapeutic can be linked together by a bond or via a linker. This linker can be cleavable or non-cleavable, depending on the application. In certain embodiments, a cleavable linker can be used to release the therapeutic agent after transport to the desired target. The intended nature of the conjugation or coupling interaction, or the desired biological effect, will determine the choice of linker group. In some embodiments, the lipid in the lipid conjugated therapeutic agent is cholesterol.

The supramolecular combinatorial therapeutic can comprise from about 1% to about 99% (w/w) of the therapeutic agent or a conjugate thereof. Further the therapeutic agent or a conjugate thereof can be present in 10:1 to 1:10 ratio with the BLZ-945-lipid conjugate. Without limitations, BLZ-945-lipid conjugate and therapeutic agent (or a conjugate thereof) in the supramolecular combinatorial therapeutic can be in ratio 10:1 to 1:10, 5:1 to 1:5, or 2.5:1 to 1:2.5. In some embodiments, BLZ-945-lipid conjugate and therapeutic agent (or a conjugate thereof) in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10.

In some embodiments, the therapeutic agent is an antibody (e.g., polyclonal or monoclonal antibody) or an antigen binding fragment thereof. In one embodiment, the therapeutic agent is an antibody (e.g., polyclonal or monoclonal antibody), or an antigen binding fragment thereof, conjugated with a lipid, e.g., cholesterol. In some embodiments, the antibody is an immunomodulator comprising an anti-PD-1 antibody, an anti-PD-L1 antibody and combinations thereof. In some embodiments, the immunomodulator is conjugated with lipid, e.g. cholesterol or other lipids disclosed herein.

In some embodiments, the therapeutic agent is a chemotherapeutic or anti-cancer agent. As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

The term chemotherapeutic agent is a broad one covering many chemotherapeutic agents having different mechanisms of action. Generally, chemotherapeutic agents are classified according to the mechanism of action. Many of the available agents are anti-metabolites of development pathways of various tumors, or react with the DNA of the tumor cells. There are also agents which inhibit enzymes, such as topoisomerase I and topoisomerase II, or which are antimiotic agents.

Chemotherapeutic agents include, but are not limited to, an aromatase inhibitor; an antiestrogen, an anti-androgen (especially in the case of prostate cancer) or a gonadorelin agonist; a topoisomerase I inhibitor or a topoisomerase II inhibitor; a microtubule active agent, an alkylating agent, an anti-neoplastic anti-metabolite or a platin compound; a compound targeting/decreasing a protein or lipid kinase activity or a protein or lipid phosphatase activity, a further anti-angiogenic compound or a compound which induces cell differentiation processes; a bradykinin 1 receptor or an angiotensin II antagonist; a cyclooxygenase inhibitor, a bisphosphonate, a heparanase inhibitor (prevents heparan sulphate degradation), e.g., PI-88, a biological response modifier, preferably a lymphokine or interferons, e.g. interferon γ, a ubiquitination inhibitor or an inhibitor which blocks anti-apoptotic pathways; an inhibitor of Ras oncogenic isoforms or a farnesyl transferase inhibitor; a telomerase inhibitor, e.g., telomestatin; a protease inhibitor, a matrix metalloproteinase inhibitor, a methionine aminopeptidase inhibitor, e.g., bengamide or a derivative thereof; a proteasome inhibitor, e.g., PS-341 (bortezomib/Velcade); agents used in the treatment of hematologic malignancies or FMS-like tyrosine kinase inhibitors; an HSP90 inhibitors; histone deacetylase (HDAC) inhibitors; mTOR inhibitors; somatostatin receptor antagonists; integrin antagonists; antileukemic compounds; tumor cell damaging approaches, such as ionizing radiation; EDG binders; anthranilic acid amide class of kinase inhibitors; ribonucleotide reductase inhibitors; S-adenosylmethionine decarboxylase inhibitors; antibodies against VEGF or VEGFR; photodynamic therapy; angiostatic steroids; AT1 receptor antagonists; ACE inhibitors; and the like.

Other chemotherapeutic agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

The chemotherapeutic agent can be linked to a component of the supramolecular combinatorial therapeutic. For example, the chemotherapeutic agent can be linked to a lipid or phospholipid component of the supramolecular combinatorial therapeutic. The chemotherapeutic agent and the component of the supramolecular combinatorial therapeutic can be linked together by a bond or via a linker. This linker can be cleavable or non-cleavable, depending on the application. In certain embodiments, a cleavable linker can be used to release the chemotherapeutic agent after transport to the desired target. The intended nature of the conjugation or coupling interaction, or the desired biological effect, will determine the choice of linker group. In some embodiments, the lipid in the lipid conjugated chemotherapeutic agent is cholesterol.

The supramolecular combinatorial therapeutic can comprise from about 1% to about 99% (w/w) of the chemotherapeutic agent or a conjugate thereof. Further the chemotherapeutic agent or a conjugate thereof can be present in 10:1 to 1:10 ratio with the BLZ-945-lipid conjugate. Without limitations, BLZ-945-lipid conjugate and chemotherapeutic agent (or a conjugate thereof) in the supramolecular combinatorial therapeutic can be in ratio 10:1 to 1:10, 5:1 to 1:5, or 2.5:1 to 1:2.5. In some embodiments, BLZ-945-lipid conjugate and chemotherapeutic agent (or a conjugate thereof) in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10.

In some embodiments, the chemotherapeutic agent can be a kinase inhibitor, e.g. a Phosphoinositide 3-kinase (PI 3-kinase or PI3K) inhibitor. Phosphoinositide 3-kinases are a family of related enzymes that are capable of phosphorylating the 3 position hydroxyl group of the inositol ring of phosphatidylinositol. They are also known as phosphatidylinositol-3-kinases. PI3Ks interact with the IRS (Insulin receptor substrate) in order to regulate glucose uptake through a series of phosphorylation events. The phosphoinositol-3-kinase family is composed of Class I, II and Class III, with Class I the only ones able to convert PI(4,5)P2 to PI(3,4,5)P3 on the inner leaflet of the plasma membrane.

Class I PI3K are heterodimeric molecules composed of a regulatory and a catalytic subunit; they are further divided between IA and IB subsets on sequence similarity. Class IA PI3K are composed of one of five regulatory p85α, p55α, p50α, p85β or p55γ subunit attached to a p110α, β or δ catalytic subunit. The first three regulatory subunits are all splice variants of the same gene (Pik3r1), the other two being expressed by other genes (Pik3r2 and Pik3r3, p85β and p55γ, respectively). The most highly expressed regulatory subunit is p85α, all three catalytic subunits are expressed by separate genes (Pik3ca, Pik3cb and Pik3cd for p110α, p110β and p110δ, respectively). The first two p110 isoforms (α and β) are expressed in all cells, but p110δ is primarily expressed in leukocytes and it has been suggested it evolved in parallel with the adaptive immune system. The regulatory p101 and catalytic p110γ subunits comprise the type IB PI3K and are encoded by a single gene each.

Class II comprises three catalytic isoforms (C2α, C2β, and C2γ), but unlike Classes I and III, no regulatory proteins. These enzymes catalyse the production of PI(3)P from PI (may also produce PI(3,4)P2 from PI(4)P). C2α and C2β are expressed throughout the body, however expression of C2γ is limited to hepatocytes. The distinct feature of Class II PI3Ks is the C-terminal C2 domain. This domain lacks critical Asp residues to coordinate binding of $Ca^{2+}$, which suggests class II PI3Ks bind lipids in a $Ca^{2+}$ independent manner. Class III are similar to II in that they bias the production of PI(3)P from PI, but are more similar to Class I in structure, as they exist as a heterodimers of a catalytic (Vps34) and a regulatory (p150) subunits. Class III seems to be primarily involved in the trafficking of proteins and vesicles.

As used herein, a "PI3K inhibitor" refers to an agent that inhibits the activity of PI3K, as measured by the level of phosphorylation of the 3 position hydroxyl group of the inositol ring of phosphatidylinositol, or as measured by the activity and/or phosphorylation (where increased phosphorylation indicates PI3K activity) of molecules downstream of PI3K. Examples of such downstream molecules are known in the art and can include, but are not limited to AKT, SGK, mTOR, GSK3P, PSD-95, S6, and 4EBP1. Methods of measuring the activity of PI3K, directly or indirectly are well known in the art, and include, by way of non-limiting example determining the level of phosphorylation of a molecule downstream of PI3K using phospho-isoform specific antibodies, which are commercially available (e.g. anti-phospho-AKT antibody, Cat No. ab66138 Abcam, Cambridge, Mass.).

In some embodiments, a PI3K inhibitor can be LY294002, PI103, and/or PI828. Further non-limiting examples of PI3K inhibitors can include wortmannin, demethoxyviridin, IC486068, IC87114, GDC-0941, perifosine, CAL101, PX-866, IPI-145, BAY 80-6946, BEZ235, P6503, TGR1202, SF1126, INK1117, BKM120, IL147, XL765, Palomid 529, GSK1059615, ZSTK474, PWT33597, TG100-115, CAL263, GNE-447, CUDC-907, and AEZS-136.

In some embodiments, the conjugate comprises a PI3K inhibitor covalently linked with a lipid. In some embodiments, the lipid conjugated PI3K inhibitor is In some embodiments, the supramolecular combinatorial therapeutic comprises at least one BLZ-945-lipid conjugate (e.g., one two, three, four, five six, seven, eight, nine, ten or more different types of lipid conjugated PI3K inhibitor). The supramolecular combinatorial therapeutic can comprise from about 1% to about 99% (w/w) of the PI3K inhibitor conjugate. Further the PI3K inhibitor conjugate can be present in 10:1 to 1:10 ratio with the BLZ-945-lipid conjugate. If two or more different PI3K inhibitor conjugates are present in the composition, each PI3K inhibitor conjugate can be independently in 10:1 to 1:10 ratio with the conjugate. Further, if two or more different PI3K inhibitor conjugates are present in the composition, the two PI3K inhibitor conjugates can be in 10:1 to 1:10 ratio. Without limitations, two different components (conjugate and PI3K inhibitor conjugate) of the supramolecular combinatorial

FORMULA I

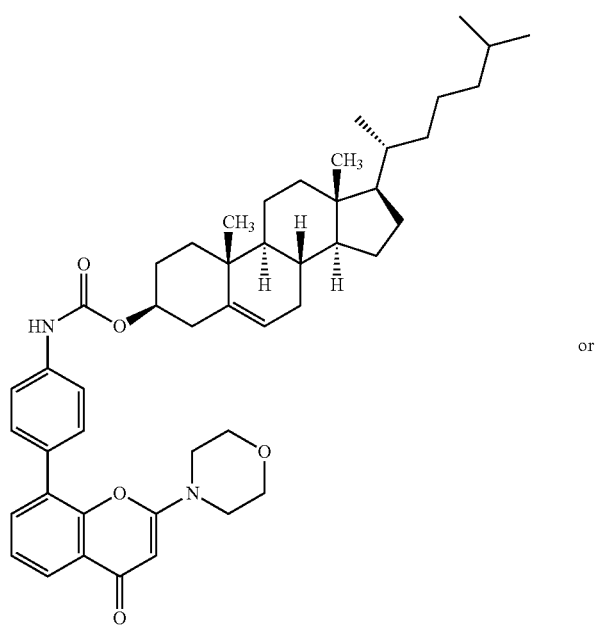

or

FORMULA II

Additional PI3K inhibitors covalently linked with a lipid are described, for example, in PCT Patent Publication No. WO2013188763, the content of which is incorporated herein by reference in its entirety.

therapeutic can be in ratio 10:1 to 1:10, 5:1 to 1:5, or 2.5:1 to 1:2.5. In some embodiments, two different components in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. If the supramolecular combinatorial therapeutic comprises more than two components ratio between any two components can be independent of ratio between any other two components.

In some embodiments, the supramolecular combinatorial therapeutic comprises a BLZ-945-lipid conjugate and a PI3K inhibitor-lipid conjugate.

In some embodiments, the supramolecular combinatorial therapeutic comprises a BLZ-945-lipid conjugate and a platinum-lipid conjugate.

In some embodiments, the supramolecular combinatorial therapeutic comprises a BLZ-945-lipid conjugate and an antibody (or an antigen binding fragment thereof) lipid conjugate. The antibody, or the antigen binding fragment thereof, can be a therapeutic agent or a targeting ligand.

In some embodiments, the supramolecular combinatorial therapeutic comprises a BLZ-945-lipid conjugate and an antibody (or an antigen binding fragment thereof) lipid conjugate, wherein the antibody is a therapeutic antibody or a targeting antibody or a combination thereof.

In a non-limiting embodiment of the present disclosure, BLZ-945-lipid conjugate is compound of formula 23.

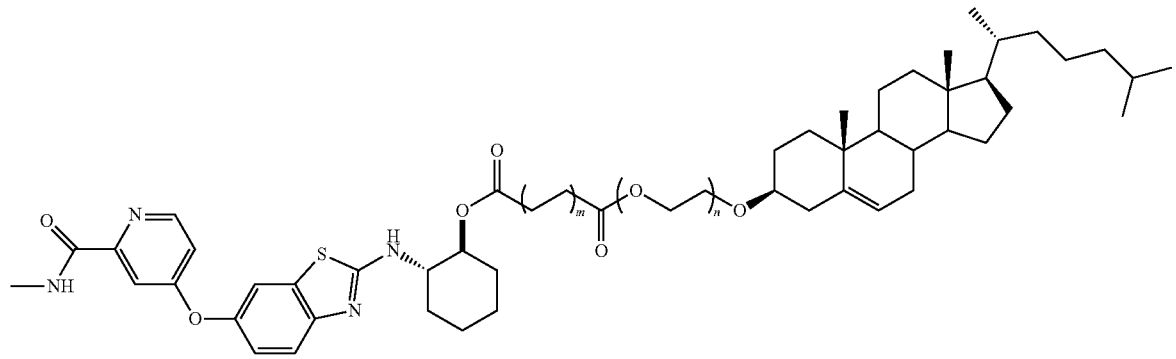

23 wherein 'n' is 1 to 10 and 'm' is 1 to 4.

In another non-limiting embodiment of the present disclosure, BLZ-945-lipid conjugate is compound of formula 24.

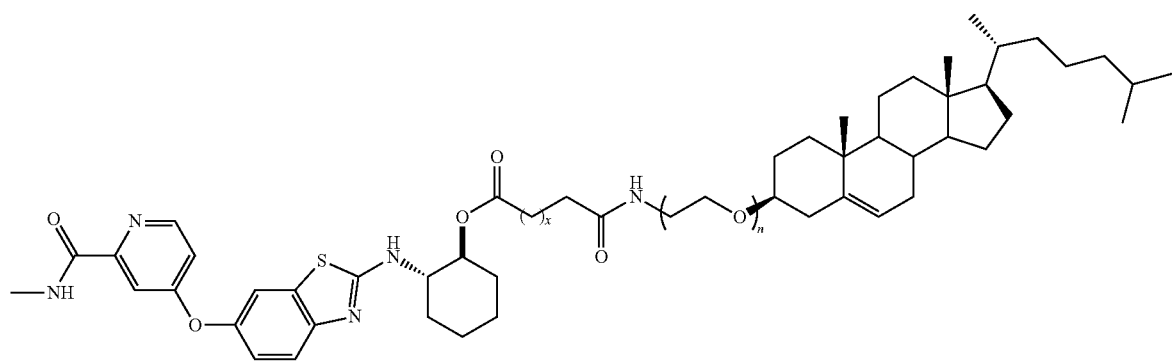

24 wherein 'n' is 1 to 10 and 'x' is 0 to 3.

In yet another non-limiting embodiment of the present disclosure, BLZ-945-lipid conjugate is compound of formula 25.

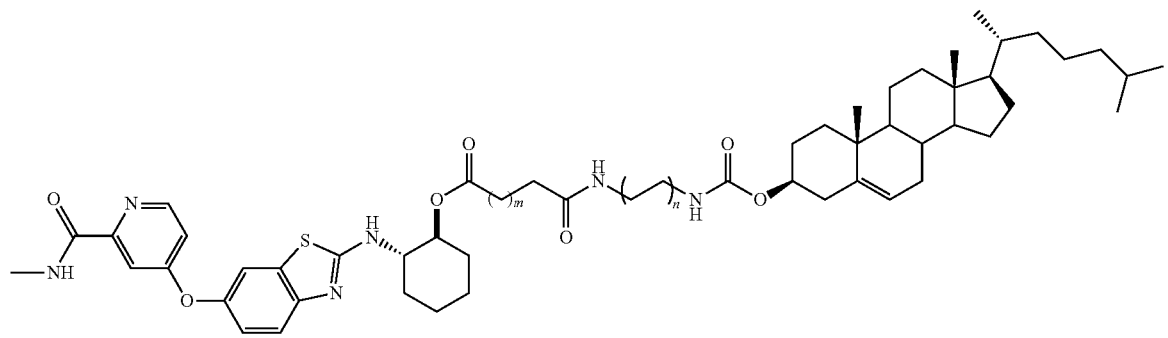

25 wherein 'n' is 1 to 10 and 'm' is 1 to 4.

In still another non-limiting embodiment of the present disclosure, BLZ-945-lipid conjugate is compound of formula 26.

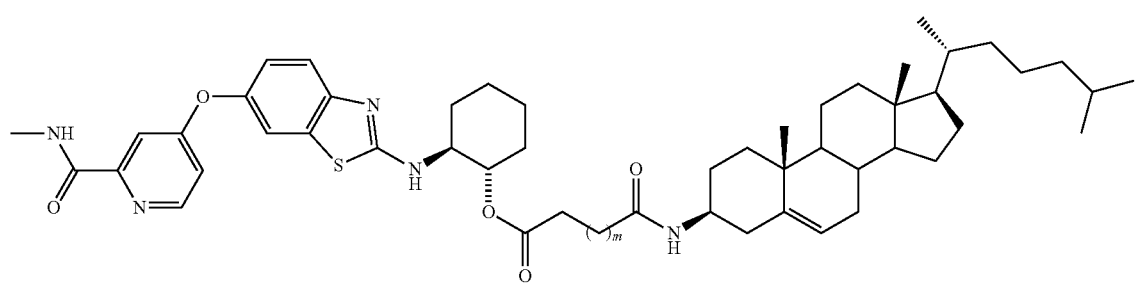

26 wherein and 'm' is 1 to 4.

In still another non-limiting embodiment of the present disclosure, BLZ-945-lipid conjugate is compound of formula 27.

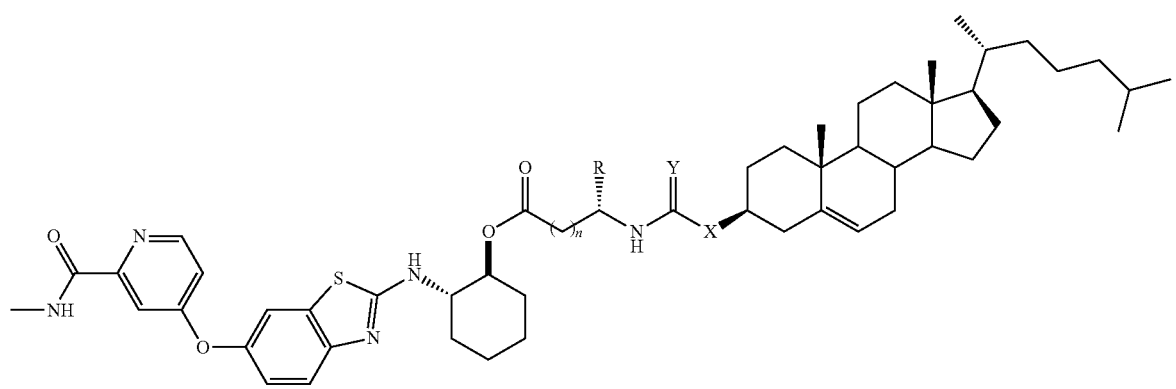

27 wherein 'n' is 1 to 10; R is H, alkyl, acid, amine, aryl or thiol; Y is C, O, NH, S; and X is C, O, NH, S.

In still another non-limiting embodiment of the present disclosure, BLZ-945-lipid conjugate is BLN101

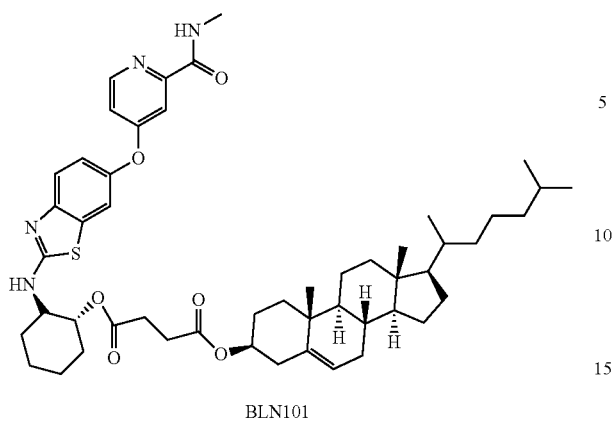
BLN101
The present disclosure further provides a BLZ-945—lipid conjugate compound selected from:
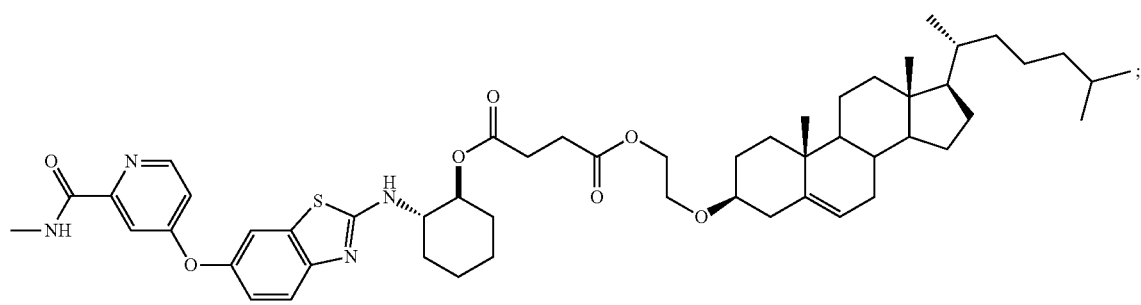
IO-801_01
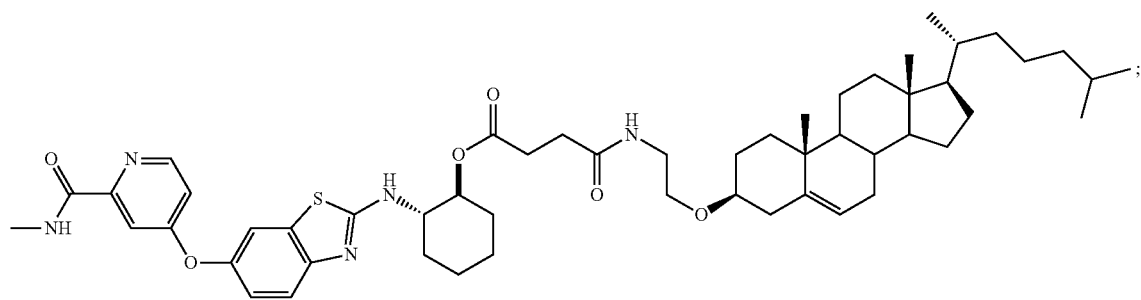
IO-801_02
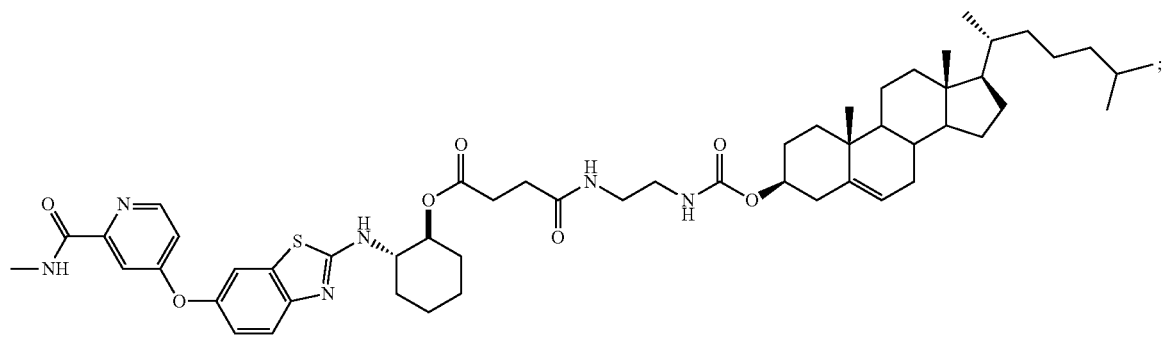
IO-801_03

IO-806_01

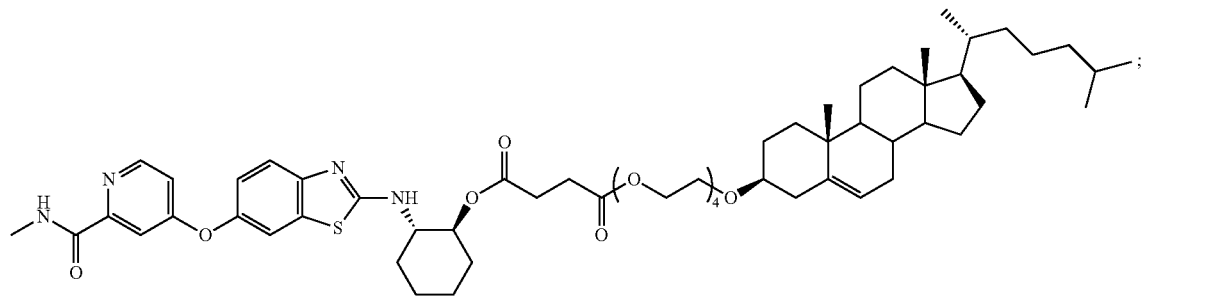

IO-806_02

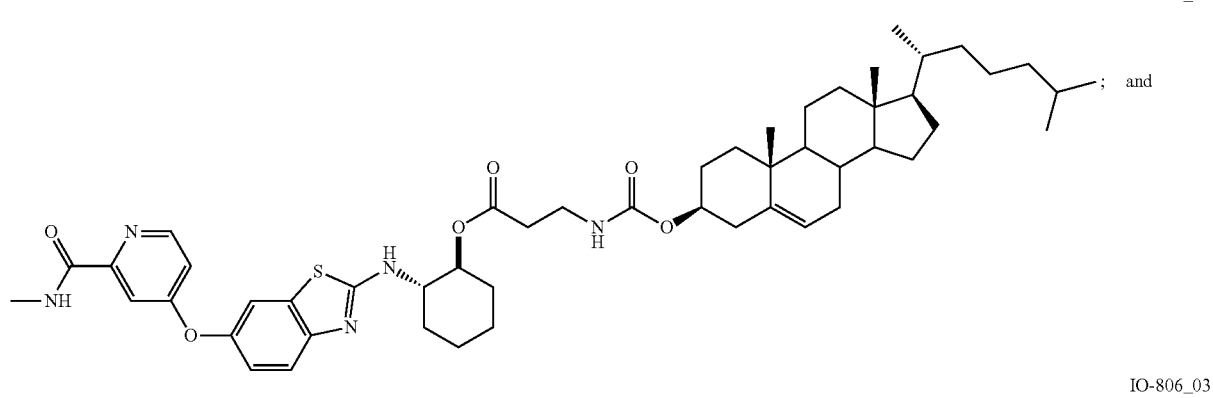
; and

IO-806_03

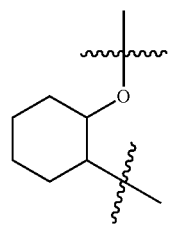 [SMILES: *OC1CCCCC1*]
.

The present disclosure also provides composition(s) comprising the compound of Formula I

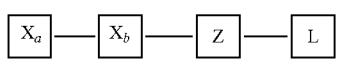

wherein, 'Xa' is

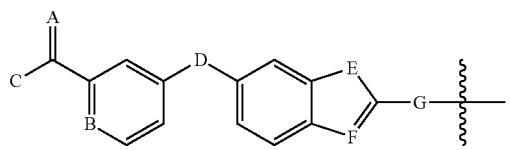

C=hydroxy, alkyl group, aryl group, cycloalkyl group
A=H, O, NH, S
B=CH, N
D=C, O, NH, S
E=C, O, NH, S
F=CH, N
G=C, O, NH, S
'Xb' is 'Z' is a linker joining 'Xb' with 'L'; and
'L' is a lipid, a lipid derivative or a lipid conjugate or any combinations thereof; or
any derivative, salt, tautomeric form, isomer, polymorph, solvate, or intermediates of compound of formula I thereof; along with pharmaceutically acceptable excipient.

In a non-limiting embodiment of the present disclosure, the composition comprises from about 1% to about 99% (w/w) of the compound of Formula I.

In another non-limiting embodiment of the present disclosure, the composition further comprises a kinase inhibitor, a chemotherapeutic agent or an immunomodulator or any combination thereof.

In yet another non-limiting embodiment of the present disclosure, the composition further comprises a co-lipid.

In still another non-limiting embodiment of the present disclosure, the co-lipid is selected from the group consisting of HSPC, DSPC, DPPC, DOPC, POPC, SOPC, Egg-PC, and DSPE-PEG, DPPE-PEG, DMPE-PEG or any combination thereof.

In a non-limiting embodiment of the present disclosure, the composition comprises from about 1% to about 99% (w/w) of the kinase inhibitor.

In a non-limiting embodiment of the present disclosure, the composition comprises from about 1% to about 99% (w/w) of the chemotherapeutic agent.

In another non-limiting embodiment of the present disclosure, the chemotherapeutic agent is selected from the group consisting of PI3K inhibitors; platinum compounds; inhibitors of topoisomerase I and II; alkylating agents; microtubule inhibitors; and angiogenesis inhibitors; or any combination thereof.

In yet another non-limiting embodiment of the present disclosure, the chemotherapeutic agent is selected from the group consisting of germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; and zoledronate; or any mixture thereof In still another non-limiting embodiment of the present disclosure, the PI3K inhibitor is selected from the group consisting of PI1103; P1828; LY294002; wortmannin; demethoxyviridin; IC486068; IC87114; GDC-0941; perifosine; CAL101; PX-866; IPI-145; BAY 80-6946; BEZ235; P6503; TGR1202; SF1126; INK1117; BKM120; IL147; XL765; Palomid 529; GSK1059615; ZSTK474; PWT33597; TG100-115; CAL263; GNE-447; CUDC-907; and AEZS-136, or any combination thereof.

In a non-limiting embodiment of the present disclosure, the chemotherapeutic agent is conjugated with a component of the composition.

In a non-limiting embodiment of the present disclosure, the chemotherapeutic agent is conjugated with Polyethylene glycol (PEG).

In a non-limiting embodiment of the present disclosure, the composition comprises from about 1% to about 99% (w/w) of the immunomodulator.

In a non-limiting embodiment of the present disclosure, the composition is a liposome, emulsion, or micelle.

In another non-limiting embodiment of the present disclosure, the composition is a nanoparticle, wherein the nanoparticle is about 1 nm to about 400 nm in diameter.

In a non-limiting embodiment of the present disclosure, the composition further comprises a pharmaceutically acceptable carrier.

In a non-limiting embodiment of the present disclosure, the composition further comprises a pharmaceutically acceptable excipient.

In another non-limiting embodiment of the present disclosure, the pharmaceutically acceptable excipient is selected from the group comprising adjuvant, diluent, carrier, granulating agents, binding agents, lubricating agents, disintegrating agent, sweetening agents, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agent, and other conventionally known pharmaceutically acceptable excipient, or any combination of excipients thereof.

In a non-limiting embodiment of the present disclosure, the composition inhibits colony stimulating factor or colony stimulating factor-1 receptor (CSF-1R) signaling pathway and is administered to a subject in need thereof through modes selected from a group comprising intravenous administration, intramuscular administration, intraperitoneal administration, hepatoportal administration, intra articular administration and pancreatic duodenal artery administration, or any combination thereof.

The present disclosure also provides a method of treating cancer, comprising, administering the compound of Formula I or derivative, salt, tautomeric form, isomer, polymorph, solvate, or intermediates thereof, or a composition thereof to a subject in need of treatment for cancer.

In a non-limiting embodiment of the present disclosure, the cancer is selected from the group consisting of breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer, or any combination thereof.

In another non-limiting embodiment of the present disclosure, the method comprises co-administering one or more additional anti-cancer therapy to the subject.

In yet another non-limiting embodiment of the present disclosure, the additional anti-cancer therapy is selected from the group consisting of surgery, chemotherapy, radiation therapy, thermotherapy, immunotherapy, hormone therapy, laser therapy, and anti-angiogenic therapy, or any combination thereof.

In still another non-limiting embodiment of the present disclosure, the additional anti-cancer therapy comprises administering a kinase inhibitor, a chemotherapeutic agent, an immunomodulator or any combination thereof, to the subject.

In a non-limiting embodiment of the present disclosure, the immunomodulator activates an immune response against cancer cells, wherein the immunomodulator is selected from the group consisting of antibody, natural killer cells, lymphokine-activated killer cells, cytotoxic T cells and dendritic cells, anti-PD-L1 antibodies, anti-PD-1 antibodies, anti-CD52 antibodies, anti-VEGF-A antibodies, anti-CD30 antibodies, anti-EGFR antibodies, anti-CD33 antibodies, anti-CD20 antibodies, anti-CTLA4 antibodies, anti-HER-2 antibodies, interferons, and interleukins, or any combination thereof.

In another non-limiting embodiment of the present disclosure, the antibody is a therapeutic antibody or a targeting antibody or a combination thereof.

The present disclosure also provides a method for inhibition of CSF or CSF-1R signalling pathway in a cell, wherein said method comprises act of contacting the cell with the compound of formula I, derivative, salt, tautomeric form, isomer, polymorph, solvate, or intermediates thereof, or a composition thereof.

In some embodiments, the technology described herein relates to a pharmaceutical composition comprising a supramolecular combinatorial therapeutic and a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminium hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a composition as described herein.

In some embodiments, the pharmaceutical composition comprising a supramolecular combinatorial therapeutic can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

The present disclosure further provides a process for preparation of the compound of Formula I, said process comprising steps of:
reacting a lipid, a lipid derivative or a lipid conjugate or any combination thereof, with a linker to obtain a molecule I;
reacting the molecule I with 'alicyclic derivative of N-Boc amino-alcohol' to obtain a molecule II; and
reacting the molecule II with 'compound 22' to obtain a compound of Formula I;
wherein said 'alicyclic derivative of N-Boc amino-alcohol' is

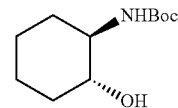

wherein said compound 22 is

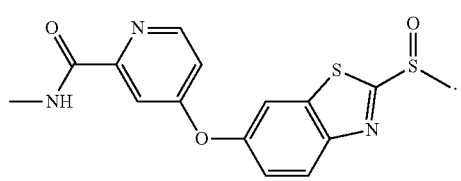

In a non-limiting embodiment, the present disclosure provides a process for preparation of the compound of Formula 23, said process comprising steps of:

reacting a compound of formula 4 with alicyclic derivative of N-Boc amino-alcohol followed by deprotection using Trifluoro acetic acid and dichloromethane to obtain a compound of formula 16, wherein said compound of formula 4 is:

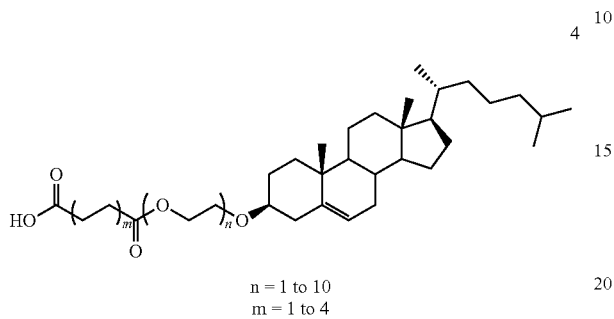

n = 1 to 10
m = 1 to 4 and
wherein said compound of formula 16 is:

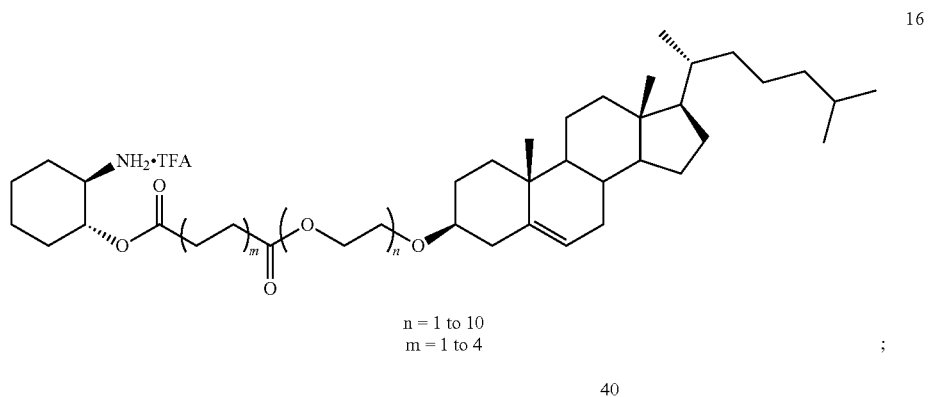

n = 1 to 10
m = 1 to 4 and
reacting the compound of formula 16 with the compound of formula 22 to obtain the compound of formula 23.

In yet another non-limiting embodiment, the present disclosure provides a process for preparation of the compound of Formula 24, said process comprising steps of:

reacting a compound of formula 8 with alicyclic derivative of N-Boc amino-alcohol followed by deprotection using Trifluoro acetic acid and dichloromethane to obtain a compound of formula 17, wherein said compound of formula 8 is: 8 is:

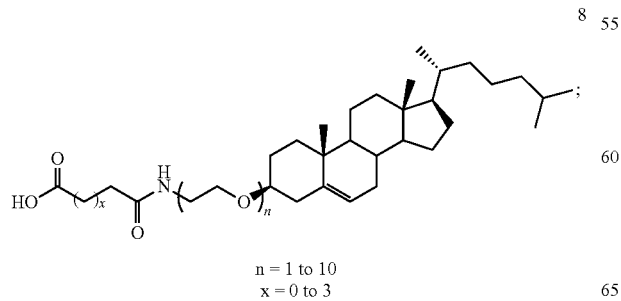

n = 1 to 10
x = 0 to 3 and
wherein said compound of formula 17 is:

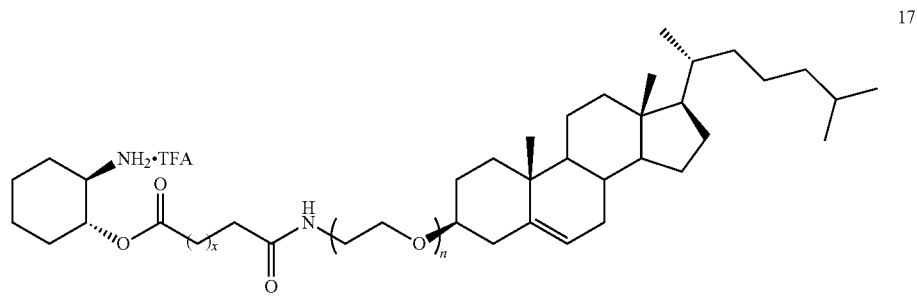

wherein n=1 to 10 and x=0 to 3; and
reacting the compound of formula 17 with the compound of formula 22 to obtain the compound of formula 24.

In still another non-limiting embodiment, the present disclosure provides a process for preparation of the compound of Formula 25, said process comprising steps of:
reacting a compound of formula 11 with alicyclic derivative of N-Boc amino-alcohol followed by deprotection using Trifluoro acetic acid and dichloromethane to obtain compound of formula 18, wherein said compound of formula 11 is:

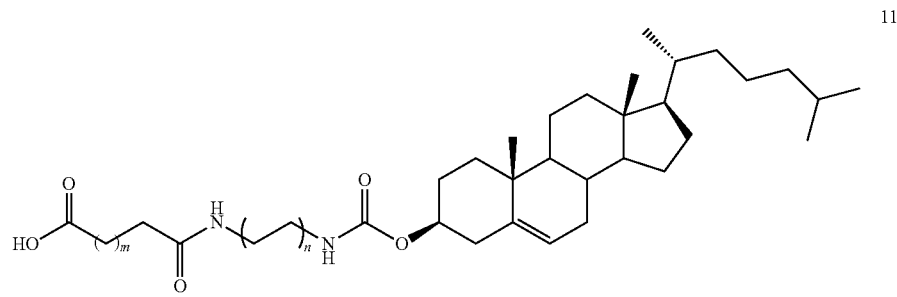

wherein 'n' is 1 to 10 and 'm' is 1 to 4,
wherein said compound of formula 18 is:

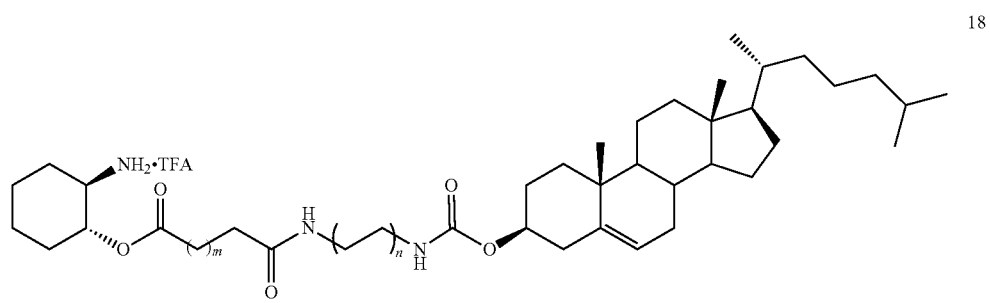

wherein 'n' is 1 to 10 and 'm' is 1 to 4; and
reacting the compound of formula 18 with the compound of formula 22 to obtain the compound of formula 25.

In still another non-limiting embodiment, the present disclosure provides a process for preparation of the compound of Formula 26, said process comprising steps of:

reacting a compound of formula 14 with alicyclic derivative of N-Boc amino-alcohol followed by deprotection using Trifluoro acetic acid and dichloromethane to obtain a compound of formula 19, wherein said compound of formula 14 is:

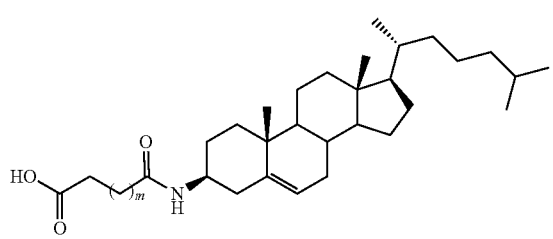

14 wherein 'm' is 1 to 4,
and
wherein said compound of formula 19 is:

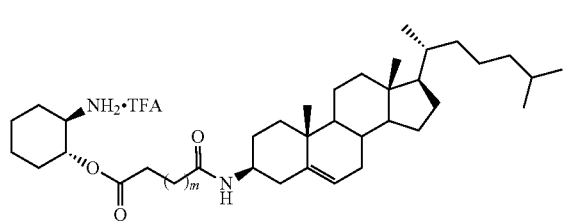

19 wherein 'm' is 1 to 4; and
reacting the compound of formula 19 with the compound of formula 22 to obtain the compound of formula 26.

In still another non-limiting embodiment, the present disclosure provides a process for preparation of the compound of Formula 27, said process comprising steps of:
reacting a compound of formula 15 with alicyclic derivative of N-Boc amino-alcohol followed by deprotection using Trifluoro acetic acid and dichloromethane to obtain a compound of formula 20,
wherein said compound of formula 15 is:

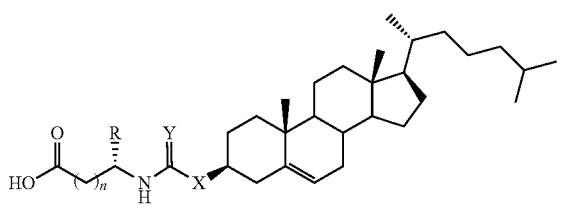

15 wherein 'n' is 1 to 10; R is H, alkyl, acid, amine, aryl, thiols; Y is C, O, NH, S; X is C, O, NH, S;

wherein said compound of formula 20 is:

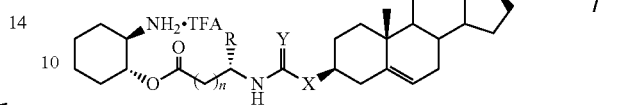

20 wherein 'n' is 1 to 10; R is H, alkyl, acid, amine, aryl, thiols; Y is C, O, NH, S; X is C, O, NH, S; and
reacting the compound of formula 20 with the compound of formula 22 to obtain the compound of formula 27.

In still another non-limiting embodiment of the present disclosure, the process for preparation of the compound of Formula I is carried out at a temperature ranging from about −10° C. to about 100° C., and for a time period ranging from about 5 minutes to about 24 hours.

In still another non-limiting embodiment of the present disclosure, the process for preparation of the compound of Formula I comprises the steps of isolation, purification or a combination thereof of the corresponding product; wherein said isolation and purification is carried out by acts selected from a group comprising addition of solvent, washing with solvent, cooling, quenching, filtration, extraction, and chromatography or any combination of acts thereof.

The present disclosure further provides a formulation comprising the compound of Formula I

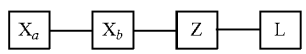

Formula I wherein, 'Xa' is

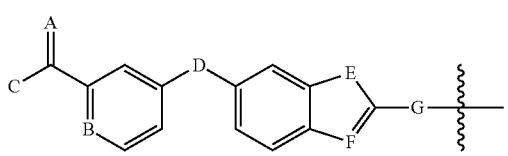

C=hydroxy, alkyl group, aryl group, cycloalkyl group
A=H, O, NH, S
B=CH, N
D=C, O, NH, S
E=C, O, NH, S
F=CH, N
G=C, O, NH, S
'Xb' is

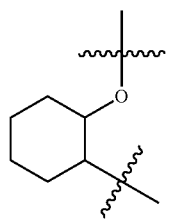 [SMILES: *OC1CCCCC1*]

'Z' is a linker joining 'Xb' with 'L'; and

'L' is a lipid, a lipid derivative or a lipid conjugate or any combinations thereof; or any derivative, salt, tautomeric form, isomer, polymorph, solvate, or intermediates of compound of formula I thereof; along with phospholipid or PEGylated phospholipid or a combination thereof.

In a non-limiting embodiment of the present disclosure, the phospholipid or PEGylated phospholipid is selected from a group comprising HSPC, DSPC, DPPC, DOPC, POPC, SOPC, Egg PC, DPPE-PEG, DMPE-PEG and DSPE-PEG or any combination thereof; wherein the composition comprises about 1% to about 99% (w/w) of these phospholipid and PEGylated phospholipid or any combination thereof.

In a non-limiting embodiment of the present disclosure, the formulation comprises the compound along with HSPC, POPC and DSPE-PEG in a ratio 5:55:35:5.

In a non-limiting embodiment of the present disclosure, the formulation comprises the compound along with HSPC, POPC and DSPE-PEG in a ratio 10:50:35:5.

In a non-limiting embodiment of the present disclosure, the formulation comprises the compound along with HSPC, POPC and DSPE-PEG in a ratio 15:50:30:5.

The compounds, compositions and methods described herein can be administered to a subject having or diagnosed as having cancer. In some embodiments, the methods described herein comprise administering an effective amount of compositions described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition described herein needed to alleviate at least one or more symptom of the disease or disorder, and relates to a sufficient amount of pharmacological composition to provide the desired effect. The term "therapeutically effective amount" therefore refers to an amount of a composition described herein that is sufficient to provide a particular anti-tumor effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

In certain embodiments, an effective dose of a composition as described herein can be administered to a patient once. In certain embodiments, an effective dose of a composition as described herein can be administered to a patient repeatedly. For systemic administration, subjects can be administered a therapeutic amount of a composition as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size and/or growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity a composition as described herein. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition as described herein can be administered over a period of time, such as over a 5 minute, 10 minute, 15 minute, 20 minute, or 25 minute period.

The dosage ranges for the administration of a composition as described herein, according to the methods described herein depend upon, for example, the form of a composition as described herein, its potency, and the extent to which symptoms, markers, or indicators of a condition described herein are desired to be reduced, for example the percentage reduction desired for tumor growth. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition as described herein in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size and/or growth). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. a decreased in tumor size and/or growth.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, PI3K, e.g. its ability to decrease the level and/or activity of PI3K can be determined, e.g. by measuring the level of a PI3K polypeptide (and/or mRNA encoding such a polypeptide) and/or the activity of PI3K. Methods for measuring the level of a given mRNA and/or polypeptide are known to one of skill in the art, e.g. RTPCR with primers can be used to determine the level of RNA and Western blotting with an antibody can be used to determine the level of a polypeptide. The activity of, e.g. PI3K can be determined using methods known in the art and described above herein.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "composition" or "pharmaceutical composition" are used interchangeably and refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the term "amphiphilic" refers to a molecule that has both a hydrophobic portion and a lipophobic portion, i.e. at least one a polar, water-soluble group and at least one a nonpolar, water-insoluble group. Typically, in a two phase system having a polar, aqueous phase and a non-polar, non-aqueous phase, an amphiphilic molecule will partition to the interface of the two phases. In simpler non limiting terms, an amphiphile is a molecule that is soluble in both an aqueous environment and a non-aqueous environment. The term "amphiphile" refers to an amphiphilic molecule.

As used herein the term "comprising" or "comprises" is used in reference to compositions, methods, and respective component(s) thereof, that are essential to the method or composition, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1—Preparation of BLZ-945-Lipid Conjugates and Intermediates Thereof

In a process for the preparation of the BLZ-945-lipid conjugates, a scheme for the preparation of the final compound was divided into 2 parts:

Preparation of the ligand

Attaching of other part to the molecule to make the final compound.

Preparation of the Ligand

In scheme 1, cholesterol was converted to compound 3 using the reported procedure. Compound 3 was further treated with cyclic acid anhydride in presence of pyridine at room temperature for overnight to yield compound 4.

Starting from previously reported compound 3, tosylation of the hydroxyl group was performed using known procedure and then converted to compound 6 using sodium azide at room temperature. (Scheme 2). The azide thus prepared was reduced to amine, which was again treated with cyclic acid anhydride to give carboxylic acid derivative 8.

In scheme 3, commercially available cholesteroyl chloride was initially treated with diamine of different chain length to give compound 10. Amine 10 was again treated with cyclic acid anhydride to give carboxylic acid derivative 11 of different chain length.

By following a known procedure compound 2 was transformed to azide derivative 12 in presence of BF3.Et2O and trimethyl silyl azide. (Scheme 4) The azide thus produced was successively reduced and then treated with cyclic acid anhydride of different chain length to prepare compound 14.

Different amino acid with varying chain lengths as well as di/tripeptide of various combination was directly attached with commercially available cholesteroyl chloride in known alkaline condition to give different cholesterol acid derivatives 15. (Scheme 5)

Scheme 1
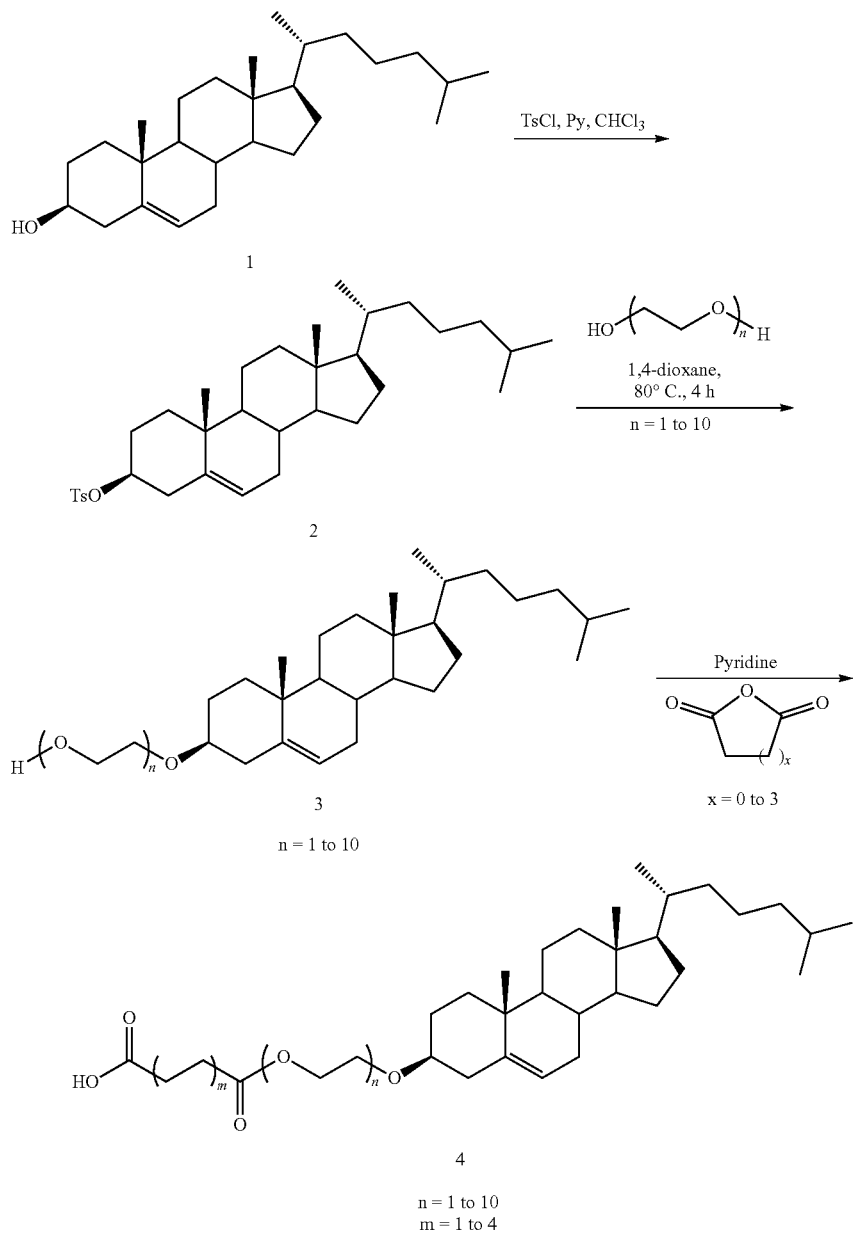
Scheme 2
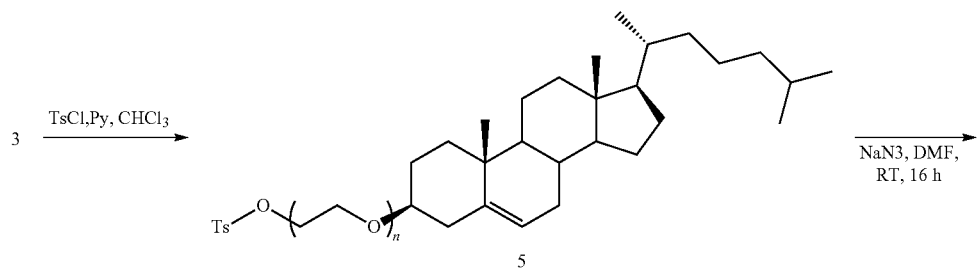

-continued
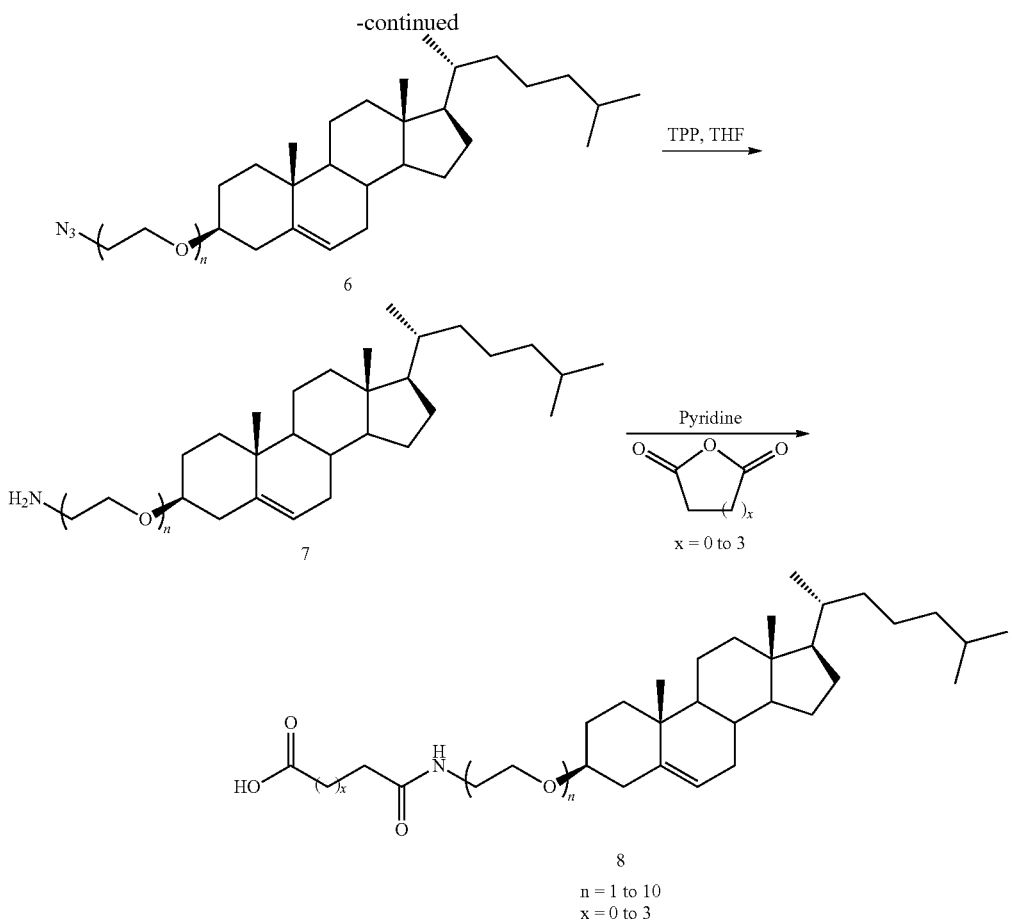
Scheme 3
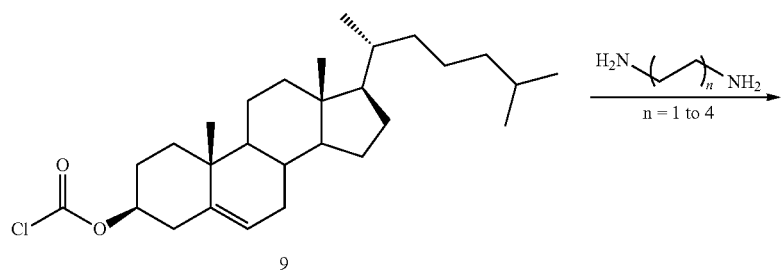
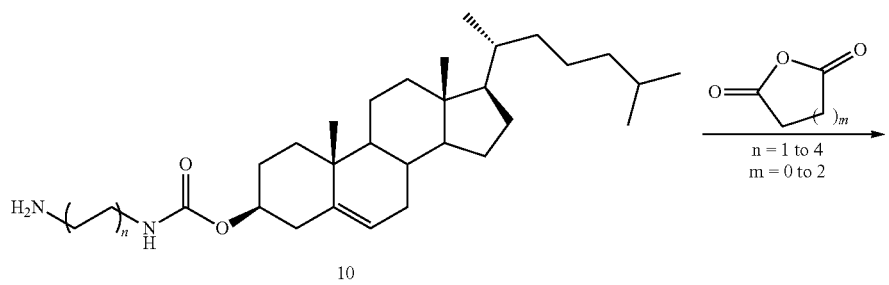

-continued
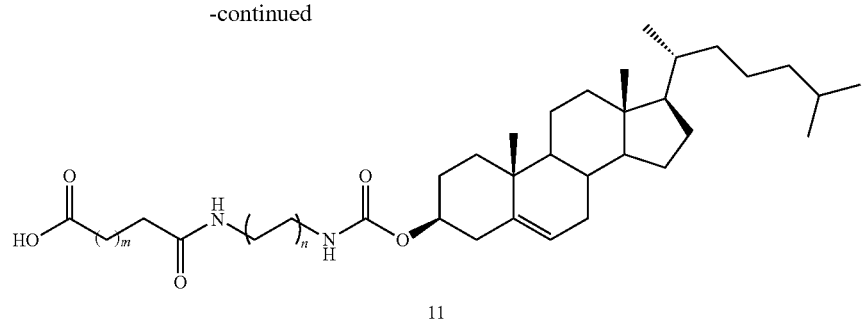
11
Scheme 4
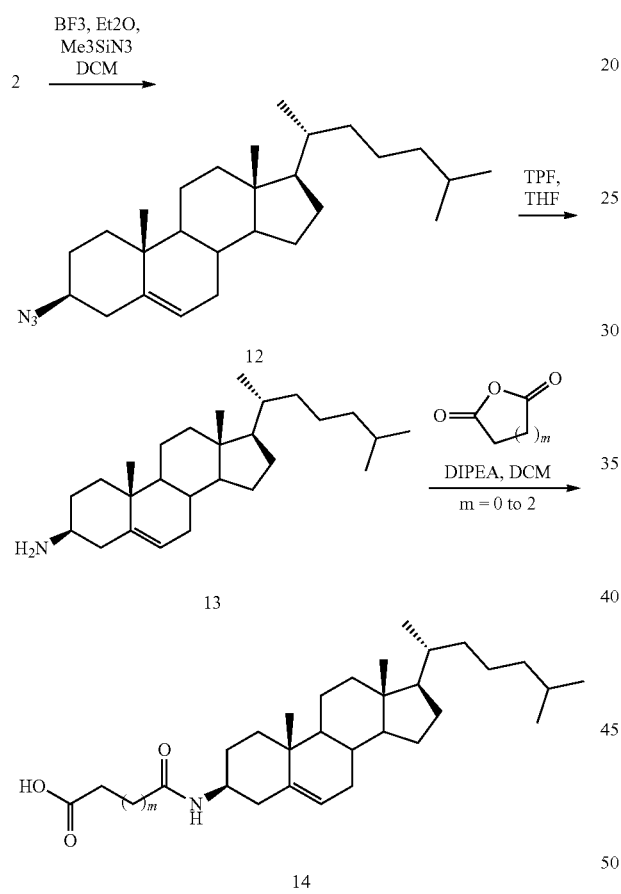
Scheme 5
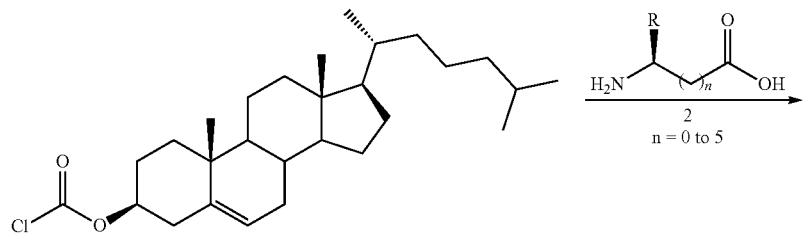

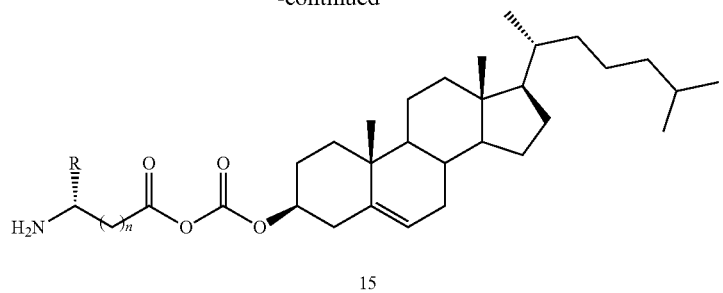

15

Preparation of Compound 22

Compound 21 is oxidized in presence of meta-Chloroperoxybenzoic acid (mCPBA) to obtain compound 22. (Scheme 6)

Scheme 6

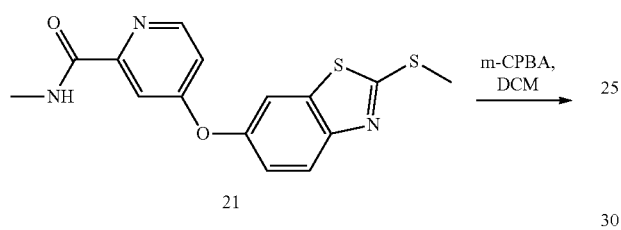

21

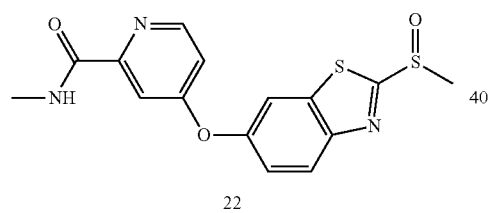

22

Attaching of Other Part to the Molecule to Make the BLG945-Lipid Conjugates

The acid compound (compound 4, compound 8, compound 11, compound 14, compound 15 obtained from Scheme 1, Scheme 2, Scheme 3, Scheme 4, Scheme 5 respectively) thus prepared was then coupled with commercially available alicyclic derivative of N-Boc amine-alcohols and subsequently deprotected to get the amines. (Scheme 7)

Scheme 7

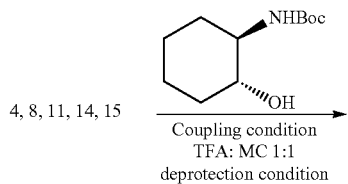

4, 8, 11, 14, 15 → Coupling condition
TFA: MC 1:1
deprotection condition

-continued
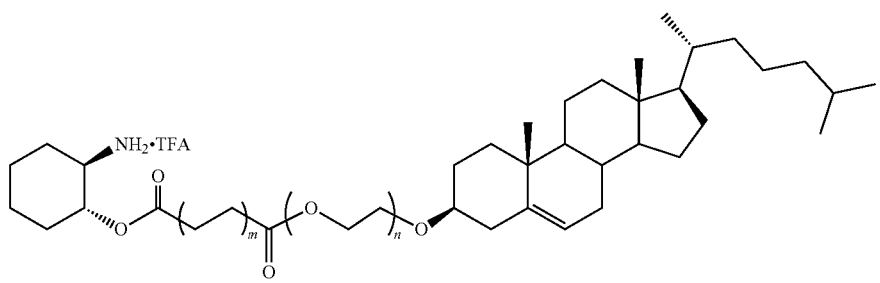
16
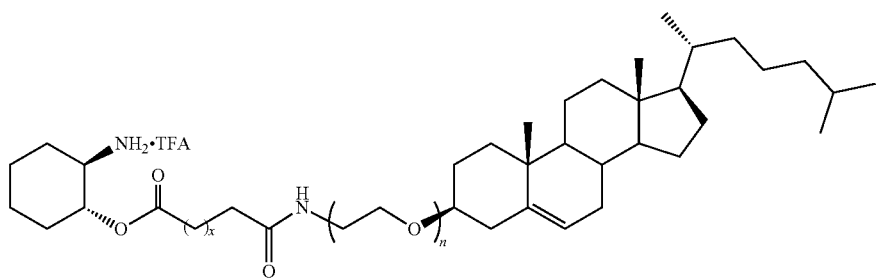
17
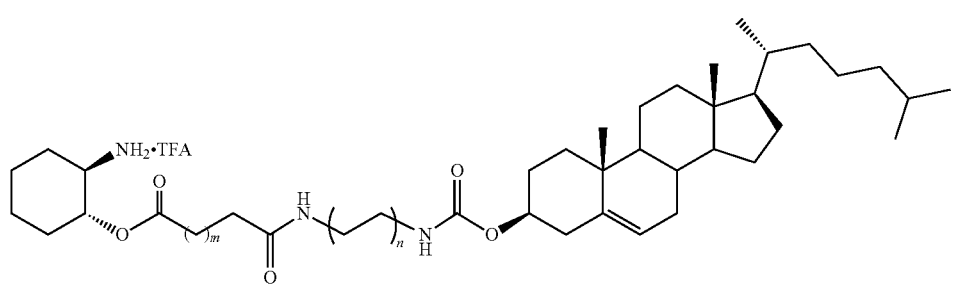
18
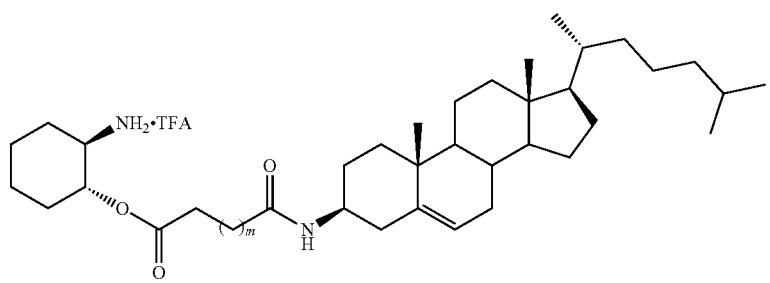
19
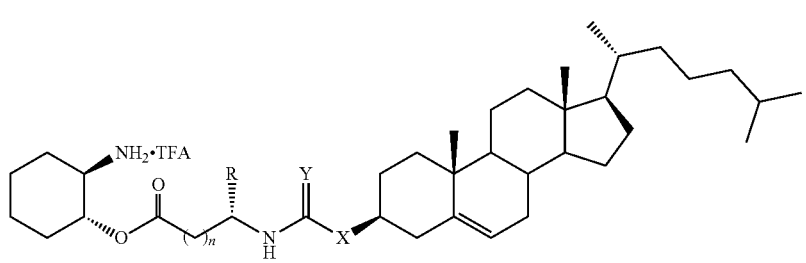
20
n = 1 to 10
m = 1 to 4

The amine salt (16-20) thus produced was treated with freshly prepared sulphoxide derivative i.e. compound 22 (obtained from Scheme 6) using diisopropyl ethyl amine in N-methyl morpholine at elevated temperature for 3 days.[viii]

The compound formation was monitored by using TLC method. (Scheme 8) The crude reaction mixture was then evaporated and then purified by column chromatography to get the final compound.

Scheme 8

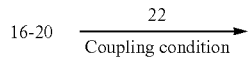

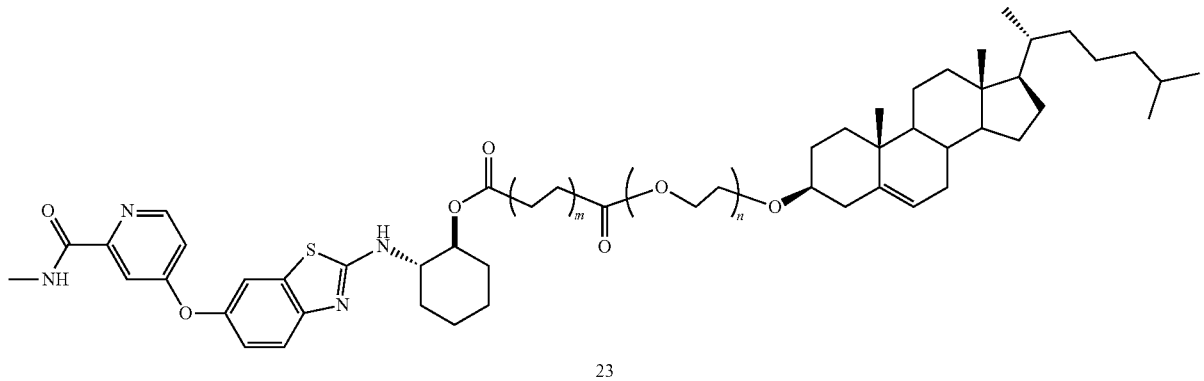

23

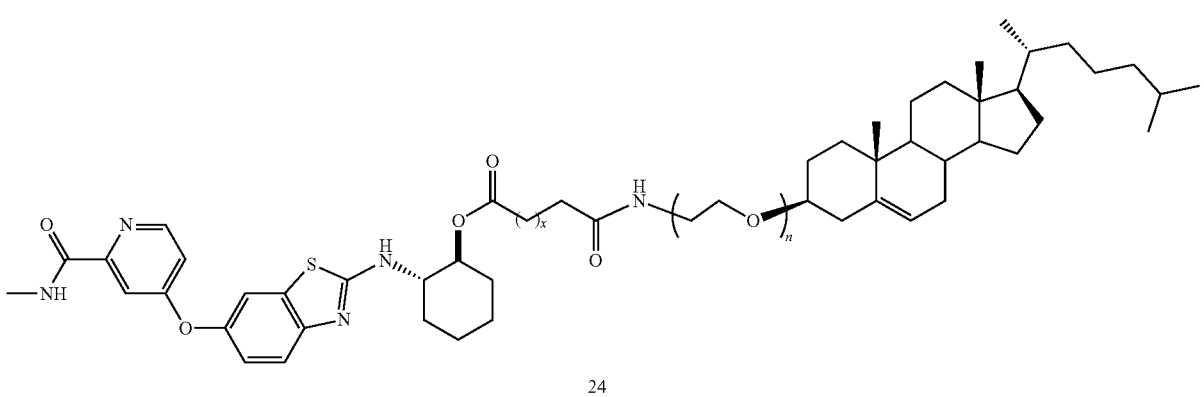

24

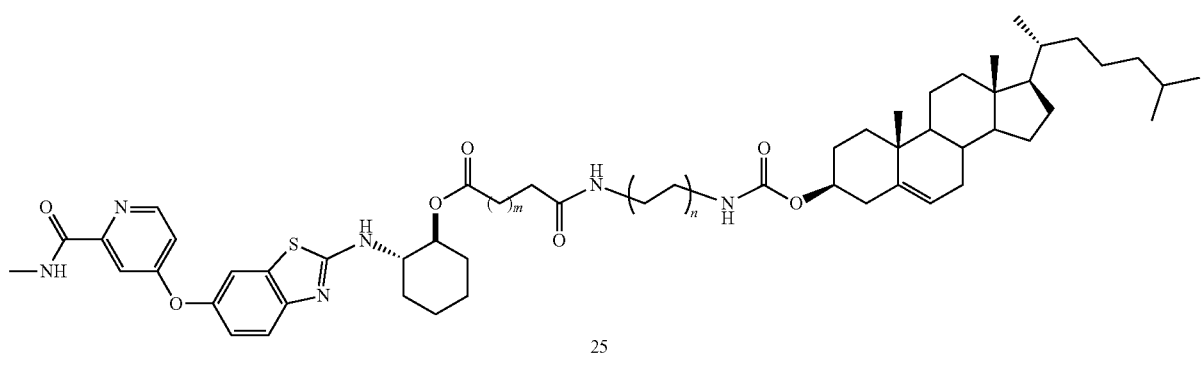

25

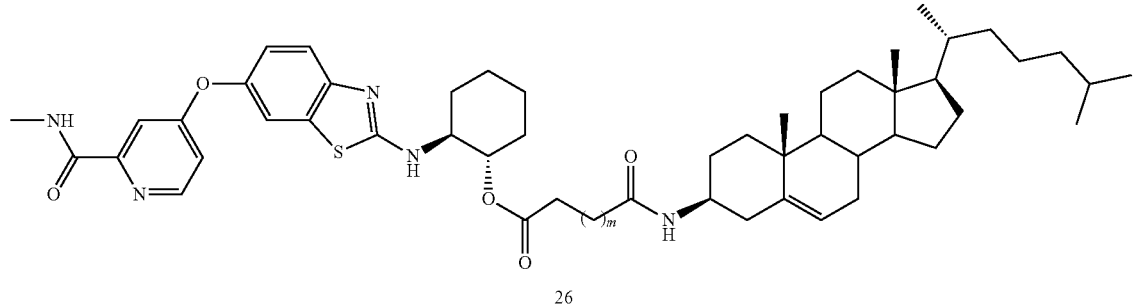

26

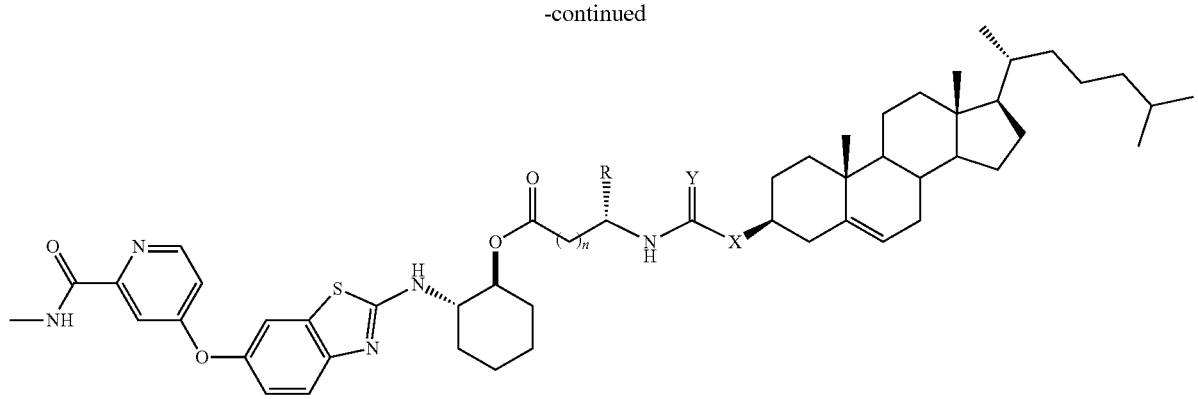

27 n = 1 to 10
m = 1 to 4
R = alkyl groups, acids, amines, aromatic, thiols

According to the scheme described above, compound IO-801_01 is synthesized by following the below mentioned scheme. (Scheme 9) Staring from commercially available cholesterol the known intermediate 28[ix] was prepared. The alcohol 28 was further treated with succinic anhydride to give corresponding acid 29 which was further coupled with commercially available tert-butyl ((1S,2S)-2-hydroxycyclo-hexyl)carbamate to yield compound 30. Compound 30 thus formed was then treated with 1:1 DCM:TFA for Boc group deprotection, the crude product thus obtained was consecutively used for the last replacement reaction with freshly prepared compound 22 to produce the final compound in moderate yield.

Scheme 9

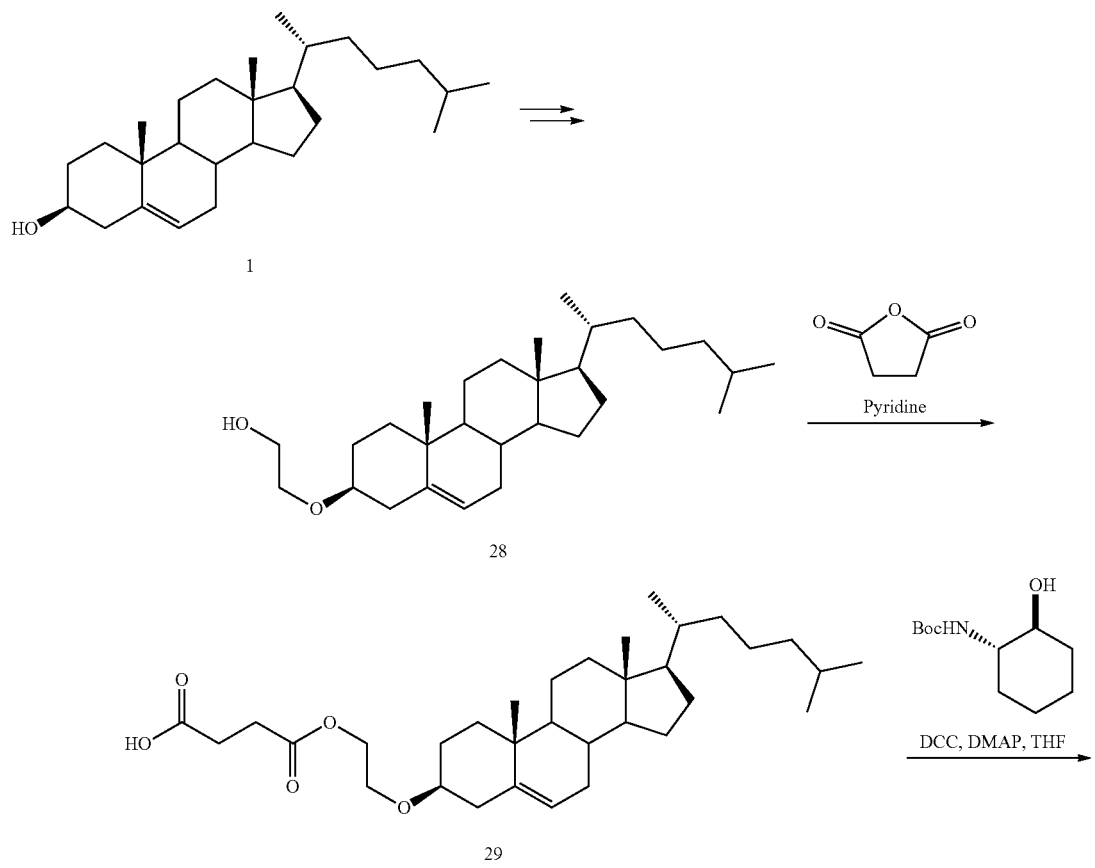

-continued

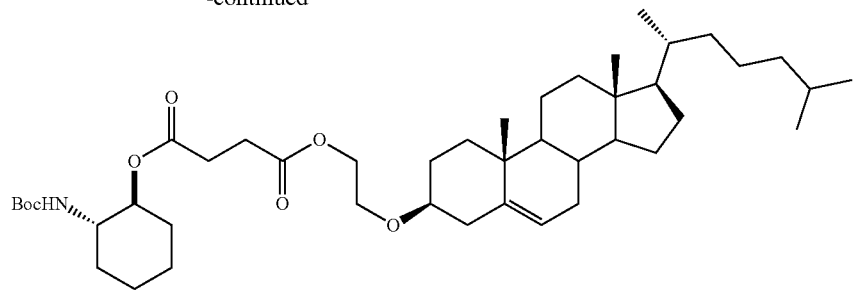

30

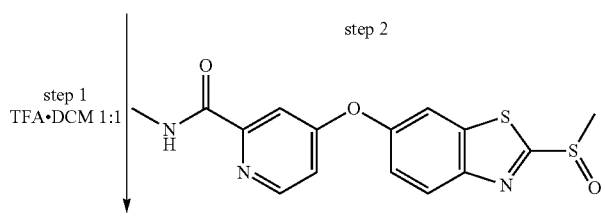

step 1
TFA•DCM 1:1 step 2

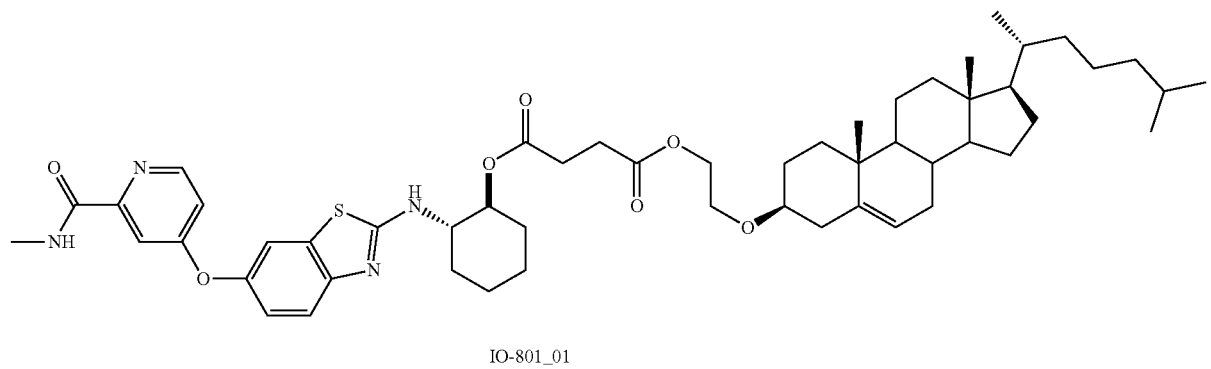

IO-801_01

Other schemes have also been worked for the preparation of the final compound IO-801_01. Starting from the intermediate acid 29. Commercially available (1S,2S)-cyclohexane-1,2-diol was first coupled to acid under usual DCC coupling condition to get the compound 31. The alcohol was then oxidised to ketone and then successively reductive amination with amine 32 to give the final compound IO-801_01. (Scheme 10)

Scheme 10

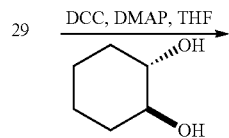

-continued
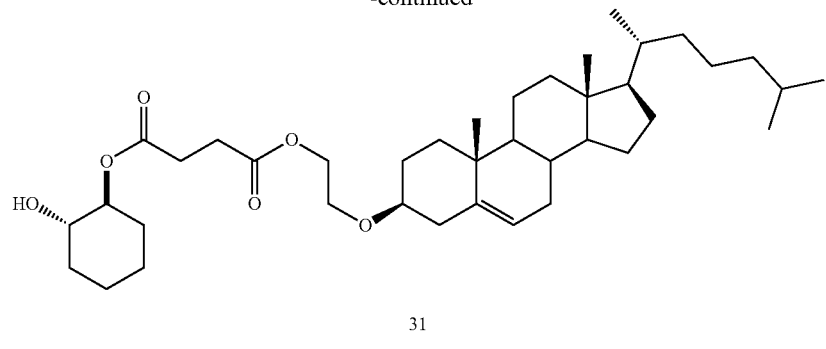
31
Step 1: PCC oxidation
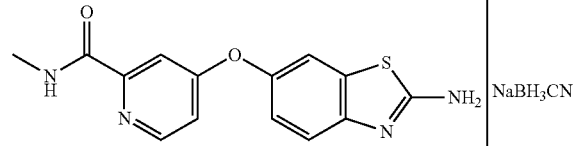 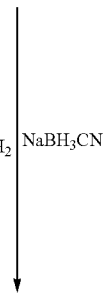
32
Step: 2
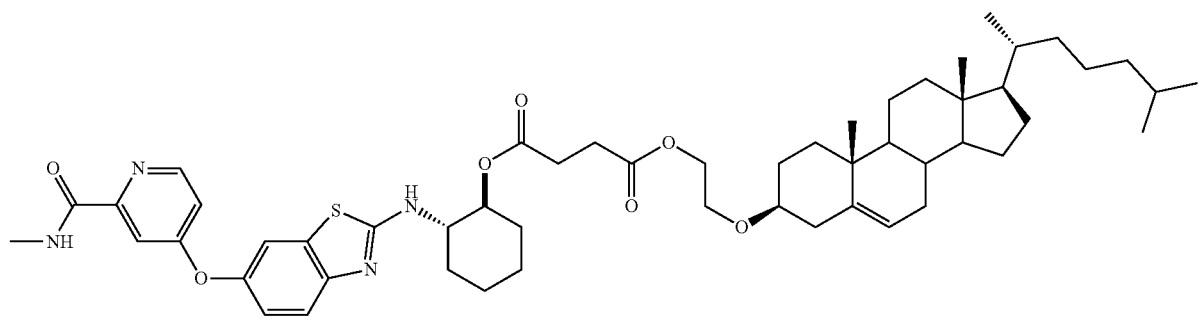
IO-801_01
In scheme 11, compound 30 was first treated with TFA: dichloromethane to deprotect the Boc group and further used for the reaction with 2-chlorobenzo[d]thiazol-6-ol to produce the compound in moderate yield. Compound 30 thus produced was treated with 4-chloro-N-methylpicolinamide to give the compound 23 in poor yield.
Scheme 11
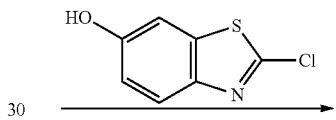
30

-continued
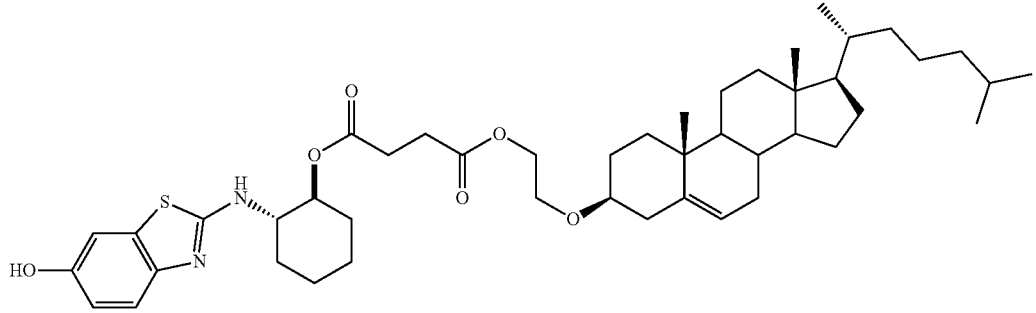
33
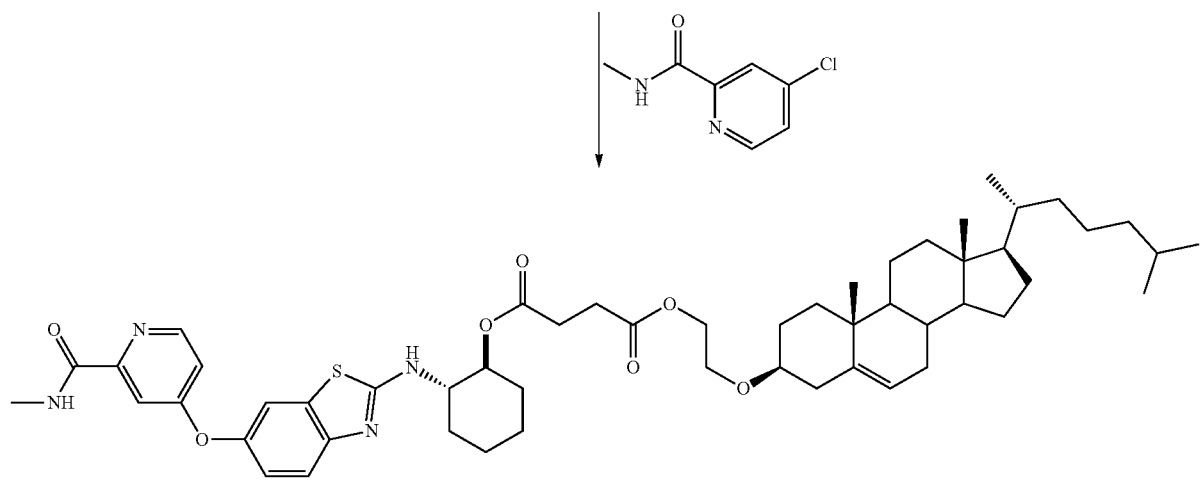
IO-801_01
Scheme 12
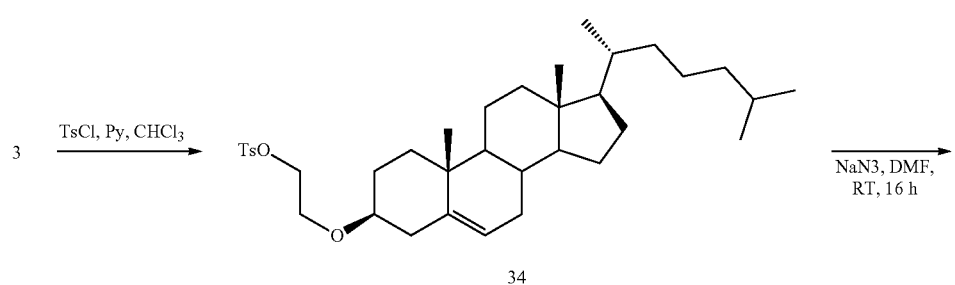
34
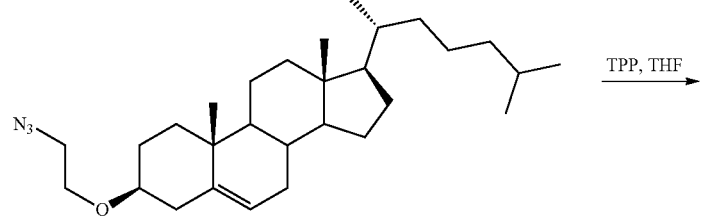
35

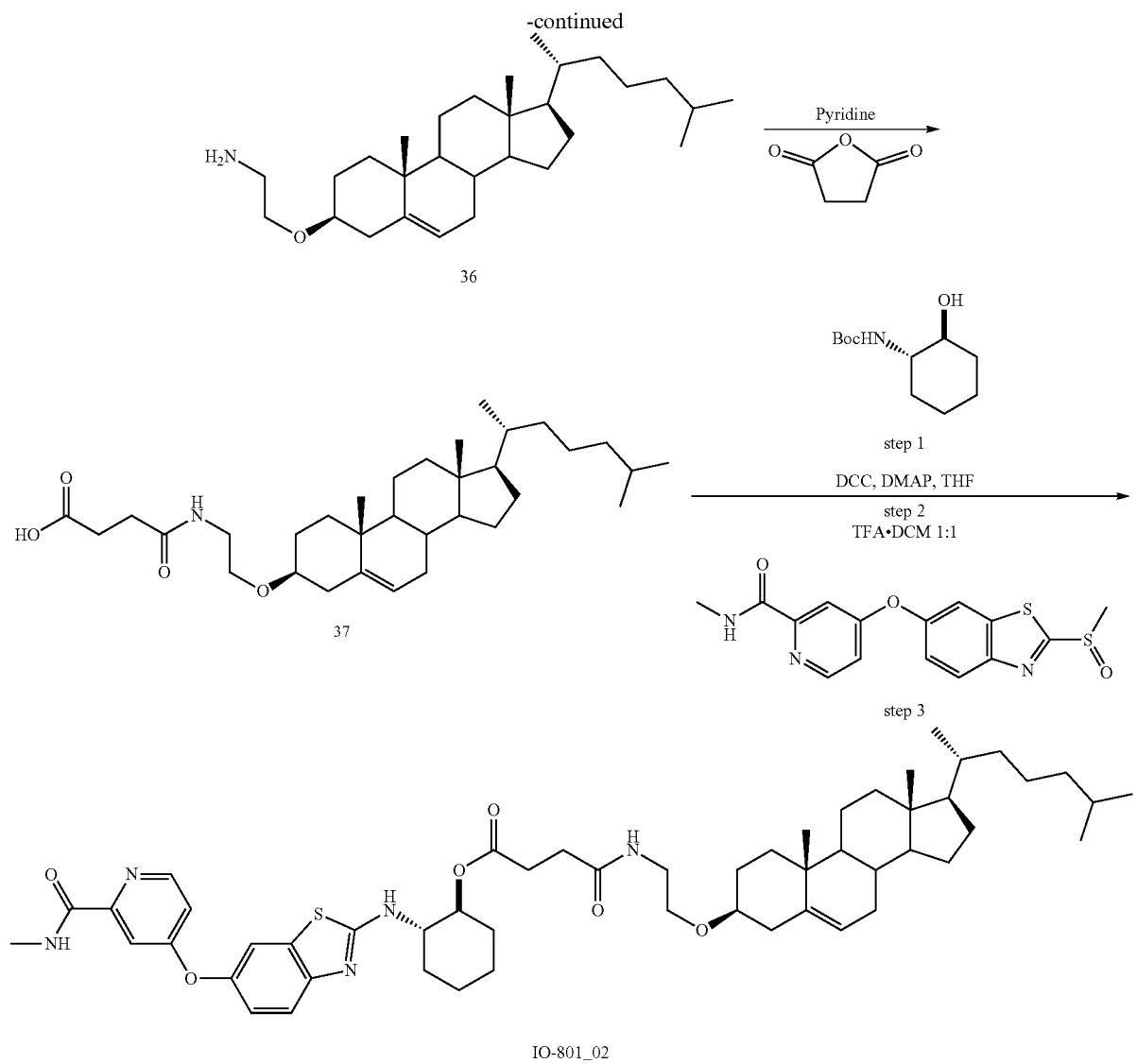

IO-801_02

For the preparation of the compound IO-801_02 intermediate acid 37, similar procedure is followed which is described previously. (Scheme 13) And then the acid was coupled with the commercially available tert-butyl (((1S,2S)-2-hydroxycyclohexyl)carbamate, compound thus formed was then treated with 1:1 DCM:TFA for Boc group deprotection, the crude product thus obtained was consecutively used for the last replacement reaction with freshly prepared compound 22 to produce the final compound in moderate yield.

Scheme 13

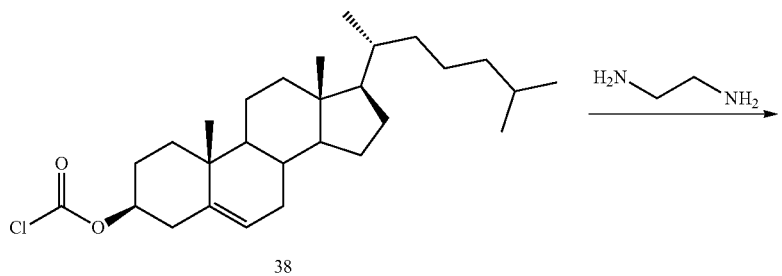

71 72
-continued
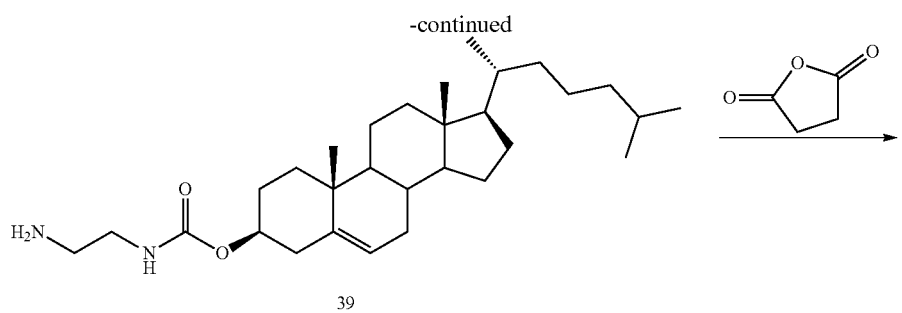
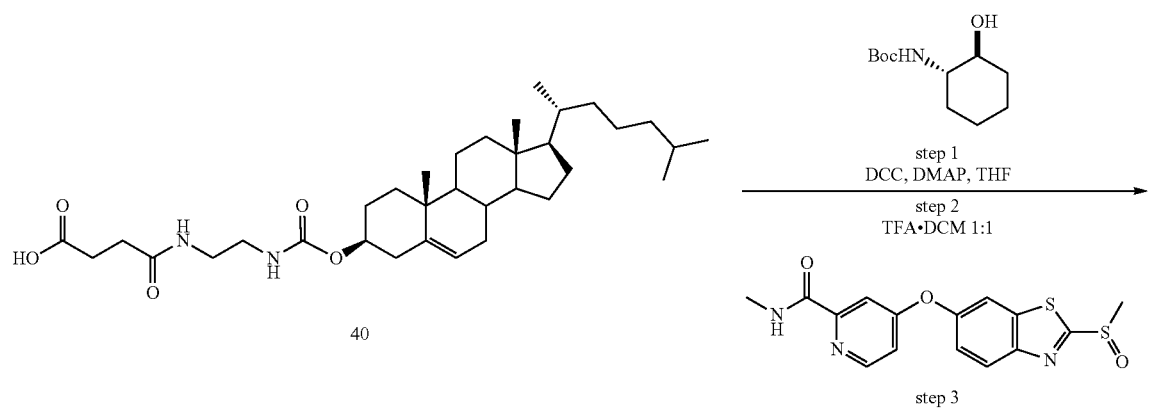
Scheme 14
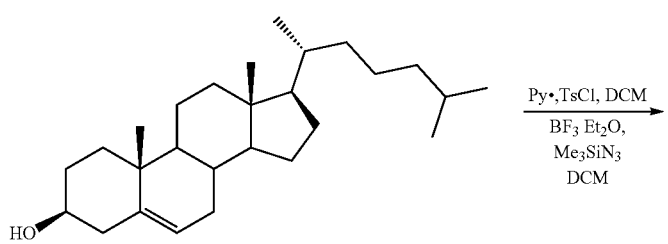

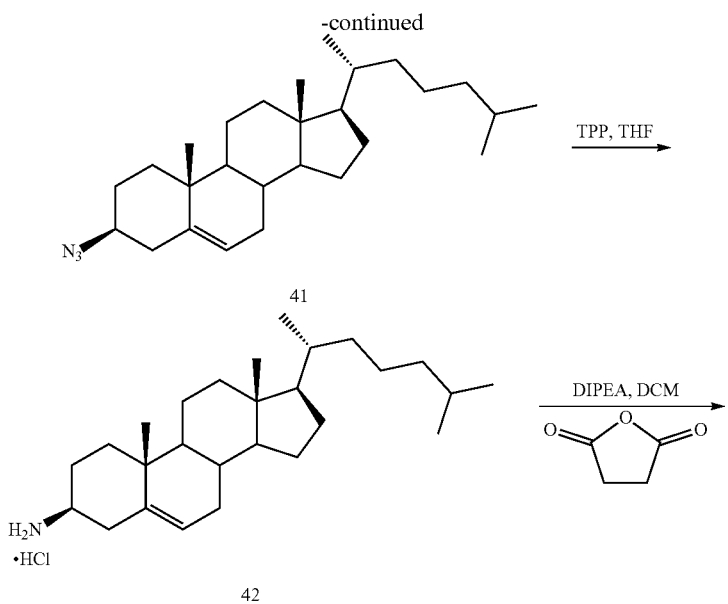
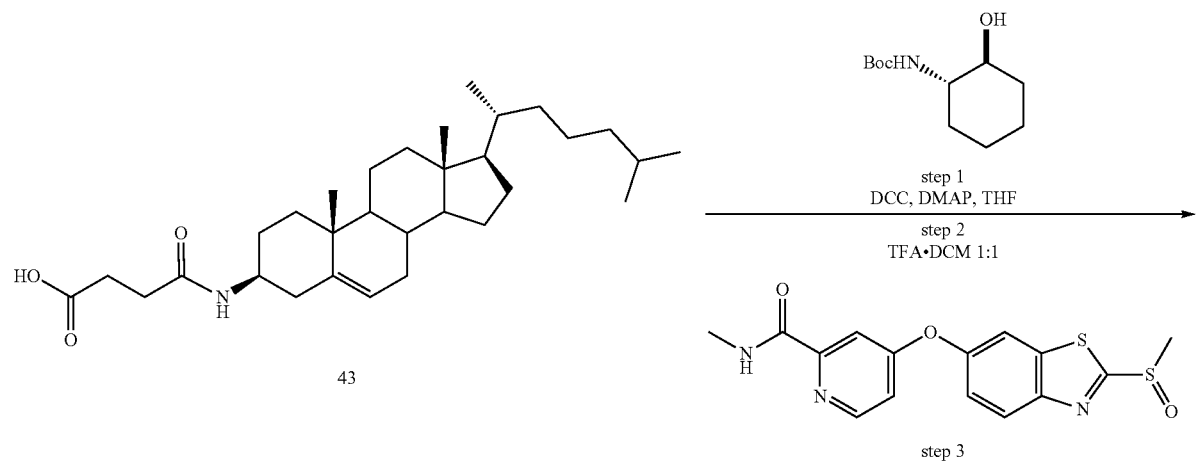
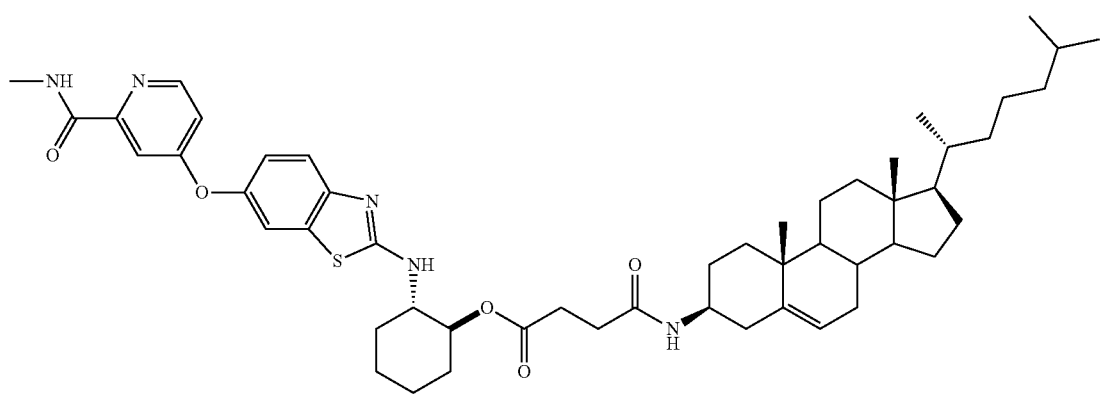

Scheme 15
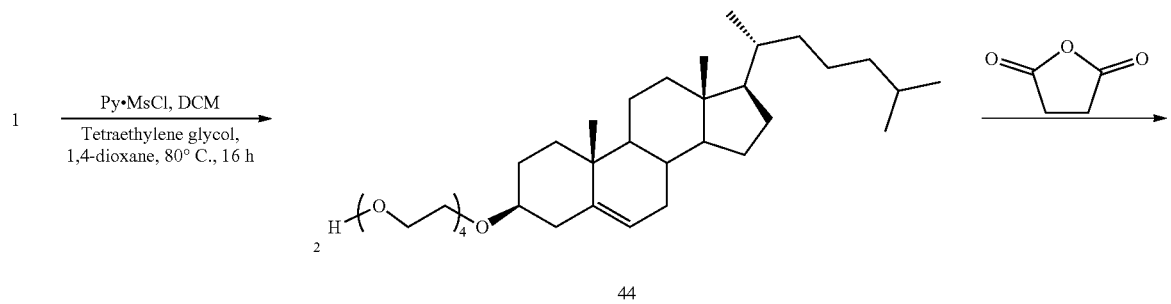
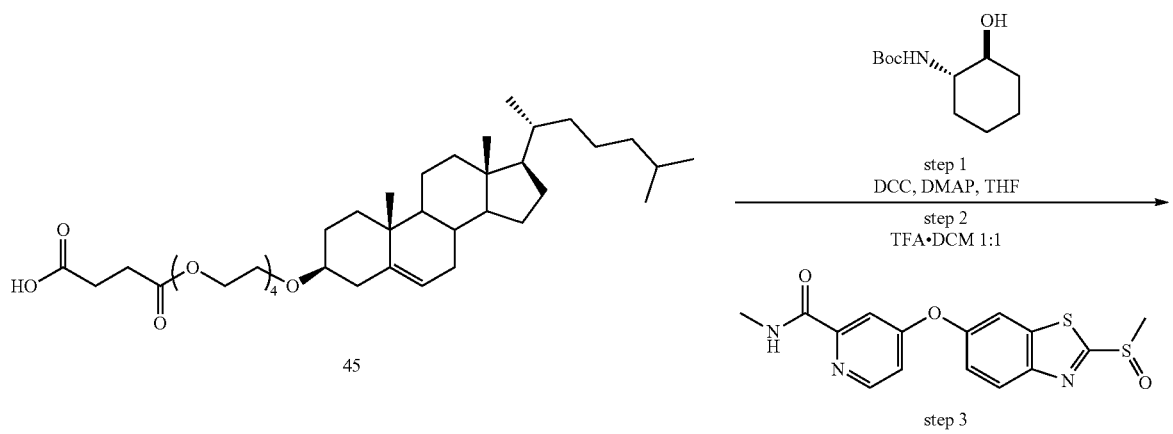
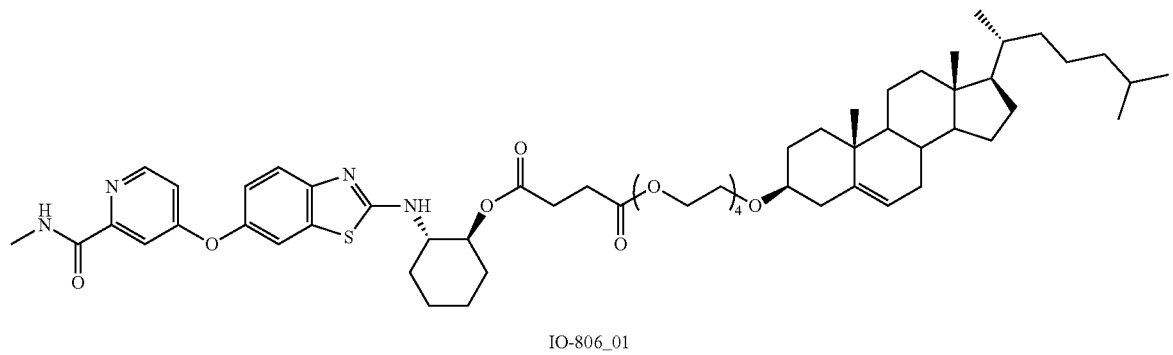
Scheme 16
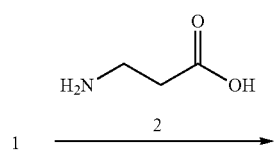

-continued
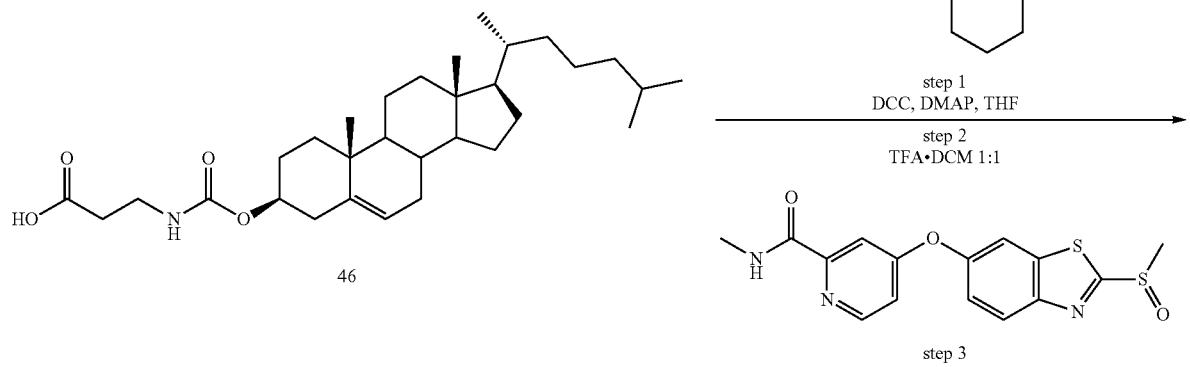
step 1
DCC, DMAP, THF
step 2
TFA·DCM 1:1
step 3
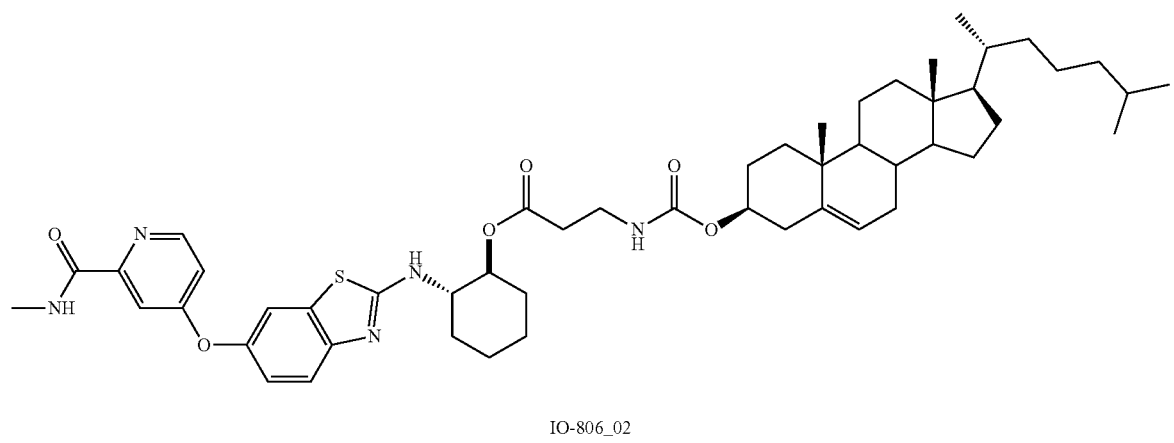
IO-806_02
Scheme 17
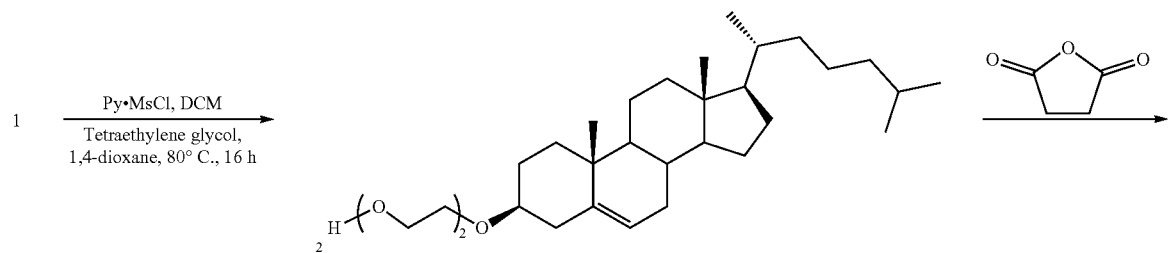

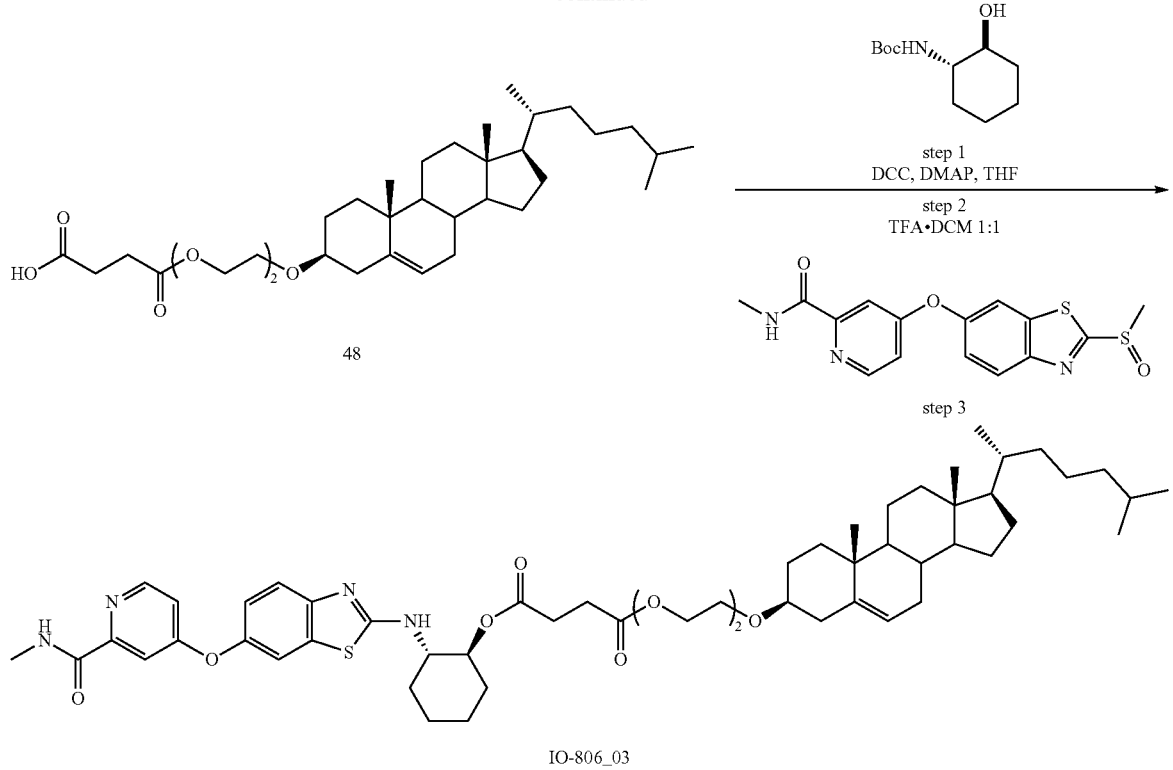

General Procedure for the Preparation of Compound 28

To a solution of cholesterol (1 eq) in chloroform (8 mL) was added pyridine (8 mL) followed by tosyl chloride (1.2 eq) at 0° C. The solution was stirred at same temperature for 6 h. Reaction was monitored by TLC. Solvent was evaporated under reduced pressure, water was added and extracted with chloroform, separate the layer. The organic layer was washed with 1N HCl solution (100 mL), dried the organic layer over anhydrous sodium sulfate and evaporated. The crude compound was dissolved in 40 mL $CHCl_3$ and MeOH (300 mL) was added to get a white precipitate, filter it and dried to get intermediate tosylate in good yield.

$^1$H NMR (500 MHz, $CDCl_3$) δ 7.87-7.80 (d, 2H), 7.41-7.32 (d, 2H), 5.37-5.28 (m, 1H), 4.21-4.12 (t, 2H), 3.70-3.63 (m, 2H), 3.17-3.05 (m, 1H), 2.47 (s, 3H), 2.28-2.23 (m, 1H), 2.16-2.07 (m, 1H), 2.05-1.94 (m, 2H), 1.88-1.78 (m, 5H), 1.63-1.22 (m, 12H), 1.21-1.06 (m, 6H), 1.04-1.00 (m, 2H), 0.99 (s, 3H), 0.95-0.92 (m, 3H), 0.90-0.87 (m, 6H), 0.69 (s, 3H).

To a solution of intermediate tosylate (1 eq) in 1,4-dioxane (80 mL) was added mono/di/tri/poly ethylene glycol (1.2 eq) and contents were heated at 80° C. for 16 h. Cool the reaction mass, solvent was evaporated on reduced pressure. Water was added and extracted with chloroform (100 mL). Layer was separated, organic layer was washed with sat. sodium bicarbonate solution (100 mL), brine, dried over anhydrous sodium sulfate and evaporated. The crude compound was purified by column chromatography using 10-15% ethyl acetate:hexane to get compound of moderate yield Compound 28:

$^1$H NMR (500 MHz, $CDCl_3$): δ 5.42-5.33 (m, 1H), 3.76-3.72 (m, 2H), 3.64-3.59 (m, 2H), 3.26-3.18 (m, 1H), 2.43-2.36 (m, 1H), 2.29-2.18 (m, 1H), 2.08-1.77 (m, 8H), 1.63-1.42 (m, 8H), 1.40-1.22 (m, 6H), 1.21-1.05 (m, 8H), 1.03 (s, 3H), 1.01-0.96 (m, 2H), 0.95-0.92 (m, 3H), 0.90-0.87 (m, 6H), 0.70 (s, 3H).

Compound 44:

$^1$H NMR (500 MHz, $CDCl_3$) δ), 5.39-5.29 (m, 1H), 3.77-3.63 (m, 16H), 3.26-3.73 (m, 2H), 3.71-3.67 (m, 10H), 3.66-3.64 (m, 4H), 3.25-3.16 (m, 1H), 2.07-1.80 (m, 5H), 1.63-1.42 (m, 8H), 1.40-1.23 (m, 5H), 1.20-1.05 (m, 7H), 1.01 (s, 3H), 0.95-0.92 (m, 3H), 0.90-0.85 (m, 6H), 0.69 (s, 3H). MS (ES-MS) $[M+Na]^+$ calcd for $C_{35}H_{62}O_5Na$ m/z 585.45, found m/z 585.46.

General Procedure for the Azide Formation

Experimental Procedure:

To a solution of tosylate (1 eq.) in dry DMF was added sodium azide (1.2 eq.) and stirred at room temperature for 16 h, water was added and extracted with ethyl acetate, brine washing was given to the organic layer, dried over anhydrous sodium sulfate and evaporated. The crude compound was purified by column chromatography to give azide of moderate yield.

Compound 35:

$^1$H NMR (500 MHz, $CDCl_3$) δ 5.43-5.34 (m, 1H), 3.73-3.63 (m, 2H), 3.45-3.34 (t, 2H), 3.28-3.18 (m, 1H), 2.44-2.36 (m, 1H), 2.29-2.19 (m, 1H), 2.06-1.78 (m, 5H), 1.63-1.24 (m, 13H), 1.23-1.04 (m, 8H), 1.03 (s, 3H), 0.95-0.93 (m, 3H), 0.90-0.87 (m, 6H), 0.70 (s, 3H).

Compound 41:

To a solution of tosylate (1 eq.) in anhydrous $CH_2Cl_2$, $TMSN_3$ (1.1 eq.) was added, followed by boron trifluoride etherate (2 eq.). The reaction was stirred at 22° C. for 2 h. When the starting material was no longer visible by TLC analysis (hexanes), the reaction was slowly poured into saturated aqueous $NaHCO_3$ (100 mL) and vigorously stirred for 10 min. The organic layer was separated and the aqueous layer was extracted with diethyl ether (60 mL×2). The organic layers were combined, washed with deionized water (100 ml.), dried over anhydrous $Na_2SO_4$ and concentrated under reduced pressure to give the crude product as light yellow solid. Flash column chromatography (hexanes) afforded the product as white solid.

Compound 41:

$^1$H NMR (500 MHz, CDCl$_3$) δ 5.45-5.38 (m, 1H), 3.28-3.16 (m, 1H), 2.35-2.26 (m, 2H), 2.08-1.80 (m, 5H), 1.64-1.44 (m, 8H), 1.42-1.33 (m, 3H), 1.31-1.23 (m, 3H), 1.19-1.07 (m, 7H), 1.03 (s, 3H), 0.95-0.92 (m, 3H), 0.91-0.87 (m, 6H), 0.70 (s, 3H).

General Procedure for the Azide Reduction to Amine

Experimental Procedure:

To a solution of azide (1 eq.) in dry THF was added triphenyl phosphine (1.5 eq.) and refluxed for 2 h. After monitoring the TLC to check the complete conversion of starting material, water was added to the reaction mixture and further refluxed for another 30 mins. Then solvent was evaporated under reduced pressure. The residue was taken in ethyl acetate and added HCl in ethyl acetate drop wise under stirring. Solid was precipitated out, filter the solid, washed it with ethyl acetate and dried.

Compound 36:

$^1$H NMR (500 MHz, CDCl$_3$) δ 8.49-8.13 (m, 2H), 5.43-5.26 (m, 1H), 3.83-3.71 (m, 2H), 3.31-3.13 (m, 3H), 2.49-2.29 (m, 4H), 2.26-2.17 (m, 1H), 2.05-1.80 (m, 5H), 1.62-1.22 (m, 12H), 1.21-1.03 (m, 6H), 1.01 (s, 3H), 0.95-0.92 (m, 3H), 0.90-0.86 (m, 6H), 0.69 (s, 3H). MS (ES-MS) [M+H]$^+$ calcd for $C_{29}H_{51}NO$ m/z 430.40, found m/z 430.22.

Compound 42:

$^1$H NMR (500 MHz, CDCl$_3$) δ 5.46-5.32 (m, 1H), 3.08-2.94 (m, 1H), 2.51-2.37 (m, 2H), 2.04-1.65 (m, 6H), 1.62-1.42 (m, 5H), 1.40-1.29 (m, 3H), 1.19-0.95 (m, 12H), 0.93-0.89 (m, 3H), 0.88-0.82 (m, 6H), 0.67 (s, 3H).

General Procedure for the Carbamate Formation with Cholesteryl Chloroformate

Experimental Procedure:

Cholesteryl chloroformate (1 eq.) was dissolved in alkyldiamine (80 mL) and the mixture stirred for 18 h. The reaction mixture was then quenched with water and extracted with dichloromethane. The organic extracts were dried ($Na_2SO_4$) and the solvent was removed in vacuo to afford a residue, which was purified by flash column chromatography.

Compound 39:

$^1$H NMR (500 MHz, CDCl$_3$) δ 6.74-6.54 (t, 1H), 5.19-5.05 (m, 1H), 4.22-4.05 (m, 1H), 2.91-2.80 (m, 2H), 2.47-2.39 (t, 2H), 2.14-1.93 (m, 2H), 1.83-1.53 (m, 6H), 1.39-1.10 (m, 11H), 1.07-1.01 (m, 1H), 0.99-0.83 (m, 7H), 0.83-0.76 (m, 5H), 0.73-0.70 (m, 3H), 0.66-0.62 (m, 6H), 0.47 (s, 3H).

Experimental Procedure:

To a solution of cholesteryl chloroformare (1 eq.) in THF was added amino acid (1.2 eq.) and 10% sodium carbonate solution and mixture was stirred at room temperature for 1.5 h. The reaction was neutralized with 2N HCl solution and extracted with DCM, organic layer was separated, washed with water and brine, dried and evaporated.

Compound 46:

$^1$H NMR (500 MHz, CDCl$_3$) δ 7.12-6.99 (m, 1H), 5.38-5.27 (m, 1H), 4.34-4.26 (m, 1H), 3.18-3.14 (m, 2H), 2.39-2.35 (m, 2H), 2.32-2.15 (m, 4H), 1.99-1.89 (m, 4H), 1.87-1.74 (m, 5H), 1.55-1.46 (m, 8H), 1.43-1.37 (m, 4H), 1.17-1.03 (m, 12H), 0.98-0.95 (m, 3H), 0.91-0.89 (m, 3H), 0.86-0.83 (m, 6H), 0.66 (s, 3H). MS (ES-MS) [M+Na]$^+$ calcd for $C_{31}H_{51}NNaO_4$ m/z 524.37, found m/z 524.39.

General Procedure for the Reaction with Acid Anhydride

Compound 29:

To a solution of compound 28 (0.3 g, 0.69 mmol) in pyridine (3 mL) was added succinic anhydride (0.083 g, 0.69 mmol) and stirred at room temperature for 16 h. Solvent was evaporated under reduced pressure, water was added and extracted with chloroform (25 mL), separate the layer. The organic layer was washed with 1N HCl solution, dried the organic layer over anhydrous sodium sulfate and evaporated. The crude compound was purified by column chromatography to obtain compound 29. Yield: 0.25 g, 67.75%.

Compound 29:

$^1$H NMR (500 MHz, CDCl$_3$): δ 5.43-5.29 (m, 1H), 4.30-4.19 (t, 2H), 3.73-3.67 (m, 2H), 3.26-3.15 (m, 1H), 2.75-2.64 (m, 5H), 2.41-2.34 (m, 1H), 2.28-2.19 (m, 1H), 2.06-1.95 (m, 2H), 1.94-1.73 (m, 3H), 1.69-1.23 (m, 12H), 1.21-1.03 (m, 7H), 1.02, (s, 3H), 1.00-0.96 (m, 1H), 0.95-0.91 (m, 3H), 0.90-0.84 (m, 6H), 0.70 (s, 3H).

Compound 37:

MS (ES-MS) [M+H]$^+$ calcd for $C_{33}H_{56}NO_4$ m/z 530.42, found m/z 530.28.

Compound 40:

$^1$H NMR (500 MHz, CDCl$_3$) δ 12.21-11.76 (m, 1H), 7.93-7.81 (t, 1H), 7.08-6.97 (t, 1H), 5.41-5.27 (m, 1H), 4.36-4.25 (m, 1H), 3.12-2.93 (m, 4H), 2.45-2.36 (t, 2H), 2.33-2.15 (m, 4H), 2.02-1.88 (m, 2H), 1.86-1.72 (m, 3H), 1.59-1.45 (m, 5H), 1.43-1.28 (m, 5H), 1.26-1.19 (m, 1H), 1.17-0.94 (m, 12H), 0.93-0.88 (m, 3H), 0.87-0.81 (m, 6H), 0.66 (s, 3H).

Compound 43:

$^1$H NMR (500 MHz, CDCl$_3$) δ 5.41-5.27 (m, 1H), 3.71-3.55 (m, 1H), 2.68-2.64 (t, 2H), 2.47-2.40 (t, 2H), 2.30-2.22 (m, 1H), 2.13-2.04 (m, 1H), 2.03-1.89 (m, 2H), 1.87-1.77 (m, 3H), 1.60-1.46 (m, 5H), 1.44-1.28 (m, 6H), 1.27-1.22 (m, 1H), 1.19-1.02 (m, 7H), 1.01-0.93 (m, 5H), 0.92-0.88 (m, 3H), 0.87-0.82 (m, 6H), 0.67 (s, 3H). MS (ES-MS) [M+H]$^+$ calcd for $C_{31}H_{52}NO_3$ m/z 486.39, found m/z 486.30.

Compound 45:

$^1$H NMR (500 MHz, CDCl$_3$) δ 11.28-11.08 (m, 1H), 5.39-5.32 (m, 1H), 4.31-4.26 (m, 2H), 3.77-3.63 (m, 16H), 3.26-3.08 (m, 2H), 2.74-2.62 (m, 4H), 2.42-2.34 (m, 1H), 2.27-2.17 (m, 1H), 2.07-1.80 (m, 5H), 1.60-1.53 (m, 5H), 1.48-1.45 (m, 3H), 1.38-1.34 (m, 2H), 1.21-1.06 (m, 6H), 1.01 (s, 3H), 0.95-0.92 (m, 3H), 0.90-0.87 (m, 6H), 0.70 (s, 3H). MS (ES-MS) [M+Na]$^+$ calcd for $C_{39}H_{66}O_8Na$ m/z 685.47, found m/z 685.55.

General Procedure for the Preparation of Sulphoxide

Compound 22:

To a solution of commercially available N-methyl-4-((2-(methylthio)benzo[d]thiazol-6-yl)oxy)picolinamide (0.1 g, 0.30 mmol) in DCM (3 mL) was added m-CPBA (0.057 g, 0.33 mmol) and stirred at room temperature for 1.5 h. Reaction quenched using sat. solution of aq. NaHCO$_3$. Separate the layer, dried and evaporated to get desired product. Yield: 0.09 g, 86.53% and proceed as such for next step. Mass and 1H NMR spectra of the compound corroborate with the reported literature.[xii]

General Procedure for the Coupling Reaction 23-27

Experimental Procedure:

To a solution of A (1.5 eq.) in DMF was added DMAP (0.5 eq.) followed by compound B (1.0 eq.). cooled to 0° C., then added DCC (1.5 eq.) and stirred at room temperature for 16 h. Water was added and extracted with DCM, dried and evaporated. Crude compound was purified by column chromatography. Purified compound without any further characterization proceeded for deprotection reaction.

To a solution of N-Boc protected amine (1.0 eq.) in DCM was added TFA (2.0 eq.). and stirred at room temperature for 3 h. Solvent was evaporated completely and proceed as such for next step.

To a solution of amine salt (1 eq.) in dry NMP was added DIPEA (5 eq.) followed by freshly prepared compound 22 (1.2 eq.) and heated at 110° C. for 3 days. The crude mixture was concentrated to get dark brown sticky liquid which was further purified by column chromatography using methanol: dichloromethane to get the final compound.

IO-801_01:

$^1$H NMR (500 MHz, CDCl$_3$) δ 8.45-8.31 (d, 1H), 8.12-7.95 (m, 1H), 7.77-7.66 (m 1H), 7.63-7.51 (d, 1H), 7.36-7.30 (d, 1H), 7.13-7.02 (m, 1H), 6.98-6.90 (m, 1H), 5.38-5.34 (m, 1H), 4.89-4.79 (m, 1H), 4.24-4.17 (t, 2H), 3.74-3.60 (m, 3H), 3.26-3.14 (m, 1H), 3.05-2.98 (d, 3H), 2.69-2.49 (m, 4H), 2.40-2.30 (m, 2H), 2.27-1.77 (m, 12H), 1.60-1.41 (m, 10H), 1.40-1.31 (m, 4H), 1.27-1.26 (m, 2H), 1.20-1.03 (m, 7H), 1.01 (s, 3H), 0.94-0.91 (d, 3H), 0.89-0.87 (m, 6H), 0.69 (s, 3H). $^{13}$C NMR (126 MHz, CDCl$_3$) δ 175.07, 172.26, 171.14, 167.74, 166.62, 164.45, 152.31, 149.68, 148.76, 140.68, 121.78, 119.80, 118.74, 113.89, 113.71, 110.23, 79.63, 75.09, 65.78, 64.35, 60.39, 59.23, 56.76, 56.17, 50.17, 42.32, 39.78, 39.52, 39.01, 37.18, 36.84, 36.19, 35.78, 31.94, 31.89, 29.69, 29.43, 29.15, 28.33, 28.23, 28.01, 26.15, 24.29, 23.83, 23.52, 22.81, 22.56, 21.07, 21.04, 19.37, 18.72, 14.20, 11.86. MS (ES-MS) [M+H]$^+$ calcd for C$_{53}$H$_{75}$N$_4$O$_{7S}$ m/z 911.54, found m/z 911.19.

IO-801_02:

$^1$H NMR (500 MHz, CDCl$_3$) δ 8.50-8.38 (d, 1H), 8.10-8.01 (m, 1H), 7.73-7.67 (m 1H), 7.41-7.33 (m, 1H), 7.22-7.15 (m, H), 7.03-6.95 (m, 1H), 5.39-5.33 (m, 1H), 4.91-4.81 (m, 1H), 3.62-3.52 (t, 2H), 3.44-3.33 (m, 2H), 3.23-3.11 (m, 1H), 3.06-2.98 (d, 3H), 2.67-2.55 (m, 2H), 2.54-2.45 (m, 2H), 2.39-2.28 (m, 2H), 2.25-2.12 (m, 3H), 2.10-1.93 (m, 3H), 1.92-1.79 (m, 5H), 1.60-1.39 (m, 12H), 1.35 (m, 4H), 1.21-1.03 (m, 10H), 1.01 (s, 3H), 0.95-0.91 (d, 3H), 0.90-0.87 (m, 6H), 0.69 (s, 3H). $^{13}$C NMR (126 MHz, CDCl$_3$) δ 175.33, 172.51, 166.26, 164.29, 156.78, 152.38, 149.79, 140.59, 121.85, 120.60, 114.12, 110.18, 79.35, 74.98, 66.36, 56.75, 56.17, 50.16, 49.17, 42.32, 39.83, 39.77, 39.52, 39.09, 37.15, 36.85, 36.19, 35.78, 33.94, 31.93, 31.89, 31.06, 30.06, 29.70, 28.41, 28.23, 28.02, 26.17, 25.62, 24.94, 24.29, 23.84, 22.81, 22.56, 21.07, 19.38, 18.72, 11.86. MS (ES-MS) [M+H]$^+$ calcd for C$_{53}$H$_{76}$N$_5$O$_6$S m/z 910.55, found m/z 910.23.

IO-801_03:

$^1$H NMR (500 MHz, CDCl$_3$) δ 8.47-8.37 (d, 1H), 8.11-8.01 (m, 1H), 7.83-7.60 (m 2H), 7.43-7.32 (m, 1H), 7.22-7.08 (m, H), 7.07-6.95 (m, 1H), 6.91-6.63 (m, 1H), 5.67-5.49 (m, 1H), 5.39-5.34 (m, 1H), 4.918-4.82 (m, 1H), 4.54-4.41 (m, 1H), 4.54-4.41 (m, 1H), 0.88-3.42 9 m, 2H), 3.38-3.17 (m, 4H), 3.08-2.95 (d, 3H), 2.66-2.23 (m, 8H), 2.19-1.77 (m, 8H), 1.68-1.22 (m, 16H), 1.21-1.05 (m, 6H), 1.01 (s, 3H), 0.94-0.92 (d, 3H), 0.91-0.84 (m, 6H), 0.69 (s, 3H). $^{13}$C NMR (126 MHz, CDCl$_3$) δ 172.96, 172.21, 166.76, 164.58, 156.92, 152.17, 149.72, 148.39, 139.78, 122.53, 119.50, 119.15, 114.09, 113.62, 109.81, 75.51, 74.62, 59.10, 56.69, 56.15, 53.43, 50.04, 42.31, 40.66, 40.25, 39.74, 39.52, 38.60, 37.02, 36.56, 36.19, 35.79, 31.91, 31.86, 31.81, 31.16, 31.06, 30.32, 29.69, 28.22, 28.15, 28.01, 26.16, 24.28, 23.94, 23.83, 22.82, 22.69, 22.56, 21.04, 19.33, 18.72, 11.86. MS (ES-MS) [M+H]$^+$ calcd for C$_{54}$H$_{77}$N$_6$O$_7$S m/z 953.56, found m/z 953.24.

IO-803_01:

$^1$H NMR (500 MHz, CDCl$_3$) δ 8.49-8.37 (d, 1H), 8.10-7.97 (m, 1H), 7.81-7.62 (m 2H), 7.64-7.52 (d, 1H), 7.35 (s, 1H), 7.19-7.10 (m, 1H), 7.05-6.92 (m, 1H), 6.01-5.77 (m, 1H), 5.38-5.28 (m, 1H), 4.95-4.78 (m, 1H), 3.87-3.43 (m, 2H), 2.63-2.54 (m, 2H), 2.50-2.33 (m, 4H), 2.31-2.24 (m, 1H), 2.21-2.06 (m, 2H), 2.04-1.91 (m, 2H), 1.90-1.80 (m, 5H), 1.65-1.31 (m, 15H), 1.29-1.25 (m, 2H), 1.21-1.03 (m, 8H), 1.00 (s, 3H), 0.95-0.91 (d, 3H), 0.91-0.86 (m, 6H), 0.69 (s, 3H). $^{13}$C NMR (126 MHz, CDCl$_3$) δ 173.16, 170.60, 166.77, 164.54, 152.23, 149.69, 148.35, 140.33, 121.84, 119.35, 119.32, 113.93, 113.47, 109.99, 75.54, 58.78, 56.68, 56.15, 50.08, 49.81, 42.30, 39.73, 39.52, 39.22, 37.87, 36.55, 36.19, 35.80, 33.95, 31.85, 31.83, 31.72, 31.33, 31.01, 30.26, 29.68, 29.05, 28.22, 28.00, 26.14, 24.26, 24.18, 23.95, 23.86, 22.81, 22.56, 20.96, 19.32, 18.72, 11.86. MS (ES-MS) [M+H]$^+$ calcd for C$_{51}$H$_{72}$N$_5$O$_5$S m/z 866.53, found m/z 866.40.

IO-806_01:

$^1$H NMR (500 MHz, CDCl$_3$) δ 8.45-8.33 (d, 1H), 8.09-7.96 (m, 1H), 7.76-7.66 (m 1H), 7.65-7.55 (m, 1H), 7.36-7.31 (m, 1H), 7.09-7.05 (m, 1H), 6.98-6.92 (m, 1H), 5.38-5.32 (m, 1H), 4.89-4.76 (m, 1H), 4.24-4.17 (m, 2H), 3.85-3.75 (m, 1H), 3.71-3.60 (m, 14H), 3.24-3.11 (m, 1H), 3.05-2.94 (d, 3H), 2.70-2.49 (m, 4H), 2.41-2.32 (m, 2H), 2.25-2.16 (m, 1H), 2.15-2.07 (m, 1H), 2.05-1.74 (m, 7H), 1.68-1.40 (m, 11H), 1.38-1.31 (m, 4H), 1.29-1.22 (m, 4H), 1.20-1.03 (m, 7H), 1.00 (s, 3H), 0.94-0.91 (d, 3H), 0.89-0.85 (m, 6H), 0.69 (s, 3H). $^{13}$C NMR: (126 MHz, CDCl$_3$) δ 172.41, 172.20, 166.58, 164.44, 152.32, 149.70, 148.88, 140.95, 121.55, 119.80, 118.87, 113.93, 113.70, 110.19, 79.54, 79.50, 75.09, 70.89, 70.59, 70.54, 70.52, 69.05, 67.27, 63.89, 59.15, 56.78, 56.17, 50.20, 42.33, 39.79, 39.52, 39.07, 37.24, 36.87, 36.20, 35.78, 31.95, 31.90, 31.43, 30.70, 29.69, 29.41, 29.11, 28.37, 28.23, 28.01, 26.14, 24.29, 23.92, 23.83, 23.62, 22.81, 22.56, 21.07, 19.38, 18.72, 12.17, 11.86. MS (ES-MS) [M+H]$^+$ calcd for C$_{59}$H$_{87}$N$_4$O$_{10}$S m/z 1043.61, found m/z 1043.47.

IO-806_02:

$^1$H NMR (500 MHz, CDCl$_3$) δ 8.44-8.36 (d, 1H), 8.09-7.96 (m, 1H), 7.75-7.56 (m, 2H), 7.37-7.30 (m, 1H), 7.10-7.03 (m, 1H), 7.00-6.93 (m, 1H), 5.42-5.21 (m, 2H), 4.87-4.74 (m, 1H), 4.52-4.38 (m, 1H), 3.91-3.73 (m, 1H), 3.49-3.24 (m, 2H), 3.07-2.94 (d, 3H), 2.52-2.42 (m, 2H), 2.41-2.30 (m, 2H), 2.27-2.10 (m, 2H), 2.04-1.90 (m, 2H), 1.88-1.78 (m, 5H), 1.60-1.41 (m, 10H), 1.38-1.32 (m, 3H), 1.31-1.21 (m, 6H), 1.19-1.05 (m, 7H), 0.99 (s, 3H), 0.94-0.91 (d, 3H), 0.90-0.85 (m, 6H), 0.71 (s, 3H). $^{13}$C NMR (126 MHz, CDCl$_3$) δ 172.17, 167.22, 166.57, 164.44, 152.31, 149.72, 148.95, 139.81, 122.48, 119.89, 118.92, 113.96, 113.76, 110.11, 75.36, 74.49, 59.24, 56.69, 56.15, 50.01, 42.31, 39.73, 39.52, 38.53, 36.97, 36.75, 36.55, 36.19, 35.79, 35.32, 31.90, 31.87, 31.54, 30.84, 29.69, 28.22, 28.08, 28.01, 26.15, 24.28, 24.00, 23.84, 23.69, 22.81, 22.69, 22.56, 21.03, 19.32, 18.72, 11.86. MS (ES-MS) [M+H]$^+$ calcd for C$_{51}$H$_{72}$N$_5$O$_6$S m/z 882.52, found m/z 882.55.

IO-806_03:

$^1$H NMR (500 MHz, CDCl$_3$) δ 8.44-8.34 (d, 1H), 8.10-7.95 (m, 1H), 7.75-7.66 (d, 1H), 7.64-7.52 (d, 1H), 7.39-7.30 (m, 1H), 7.13-7.02 (m, 1H), 6.99-6.91 (m, 1H), 5.41-5.27 (m, 1H), 5.00-4.89 (m, 1H), 4.16-4.01 (m, 2H), 3.89-3.75 (m, 1H), 3.67-3.54 (m, 8H), 3.23-3.11 (m, 1H), 3.06-2.97 (d, 3H), 2.41-2.27 (m, 2H), 2.24-2.08 (m, 2H), 2.06-1.93 (m, 2H), 1.92-1.79 (m, 5H), 1.62-1.41 (m, 11H), 1.40-1.32 (m, 3H), 1.29-1.26 (m, 5H), 1.20-1.04 (m, 7H), 0.99 (s, 3H), 0.94-0.91 (d, 3H), 0.90-0.85 (m, 6H), 0.68 (s, 3H). $^{13}$C NMR (126 MHz, CDCl$_3$) δ 170.69, 166.99, 166.57, 164.42, 152.32, 149.70, 148.90, 140.88, 121.60, 119.80, 118.94, 113.89, 113.71, 110.22, 79.53, 75.33, 70.85, 70.79, 70.54, 68.65, 67.22, 59.02, 56.78, 56.17, 50.18, 42.32, 39.79, 39.52, 39.06, 37.22, 36.86, 36.20, 35.78, 31.95, 31.93, 31.89, 29.69, 28.35, 28.23, 28.01, 26.14, 24.29, 23.98, 23.83, 23.61, 22.81, 22.56, 21.07, 19.38, 18.72, 11.86. MS (ES-MS) [M+H]$^+$ calcd for C$_{53}$H$_{77}$N$_4$O$_7$S m/z 913.55, found m/z 913.59.

BLN101—the drug BLZ-945 is conjugated to cholesterol through a linker —C(O)CH$_2$CH$_2$C(O)— to obtain BLN101.

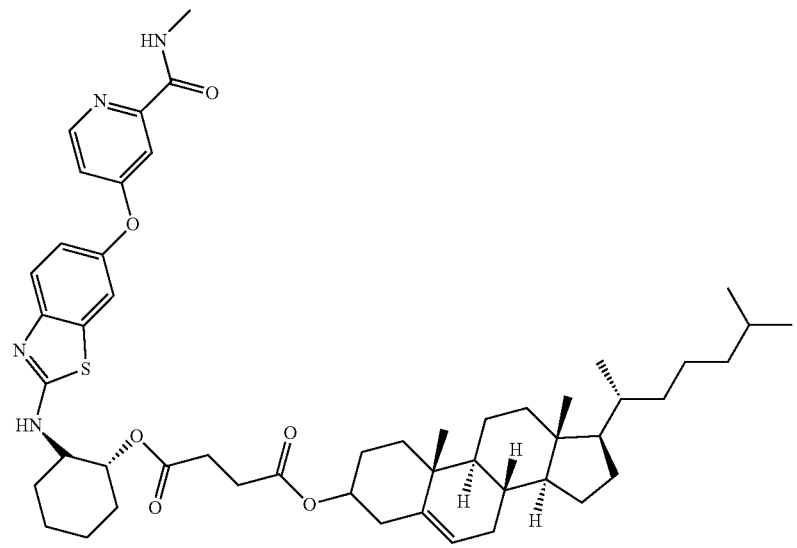

BLN101

A process for preparing a compound BLN101, said process comprising the steps of:
reacting cholesterol with succinic anhydride to obtain BLN-INT in presence of pyridine,
wherein BLN-INT is

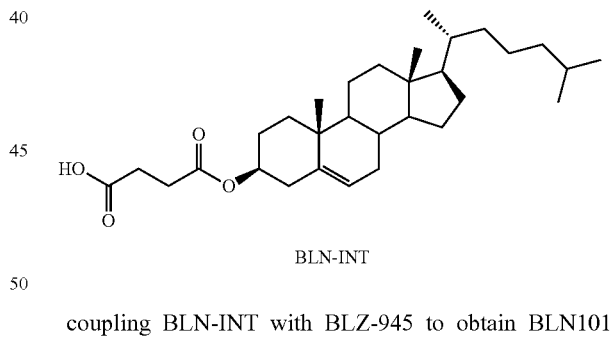

BLN-INT coupling BLN-INT with BLZ-945 to obtain BLN101.

Scheme 18

BLN101

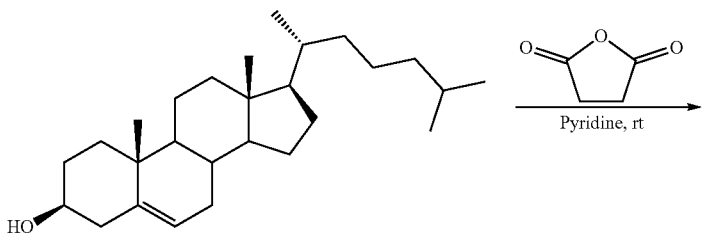

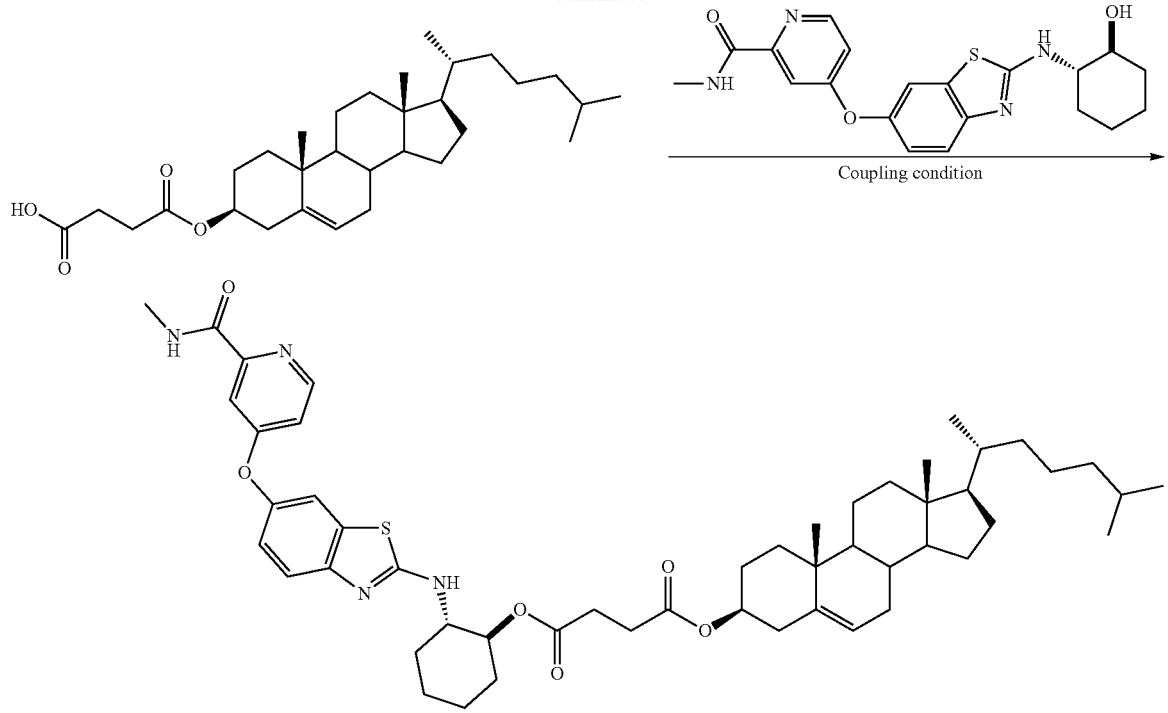

BLN101

Example 2—Formulations Comprising BLZ-945-Lipid Conjugates

Supramolecular nanostructures were formulated using thin film hydration method with varying mole ratios of phospholipids (such as HSPC, POPC, SOPC, Egg PC, etc.), PEGylated-phospholipids (such as DSPE-PEG) and CSF1R inhibitor conjugates. % Encapsulation efficiency of the CSF1R inhibitors in the supramolecules was determined by UV spectrophotometry. Average size, polydispersity index (PDI) and surface potential of the nanoparticles were measured by Dynamic light scattering (DLS).

These supramolecules were lyophilized (5% Lactose solution was used as cryo-protectant) over 16-20 hrs. The amorphous white solid powder formed thereafter was reconstituted by adding required volume of water. DLS study of this reconstituted supramolecular formulation reveals similar size, PDI, surface potential of supramolecules as it was before lyophilization.

To clarify the characteristics of these supramolecules, some examples of its implementation are described hereby:

Formulation 1

HSPC, POPC, IO-806_03 and DSPE-PEG, taken in 55:35:5:5 mol % ratio, were dissolved in Chloroform. All lipid solutions were mixed homogeneously in round bottom flask and organic solvent was evaporated by rotary evaporator resulting in a thin lipid film. The lipid film was kept under high vacuum for 3-4 hr. It was, then, hydrated (by adding 5% Lactose solution to it) for 1.0 h at 60° C. in hot water bath. Next, hydrated nanoparticles were sequentially extruded through 400 nm, 200 nm and 100 nm pore size membrane held by filter support for 11 times at 60° C. using Avanti extruder supported over hot plate. It is evident from UV measurement that 4.2 mol % of IO-806_03 was encapsulated in the supramolecule. DLS measurement reveals average size of the nanoparticles to be 153.4 nm, PDI 0.100 and surface potential −20.9 mV. The resulting solution was lyophilized and stored at 4° C.

Formulation 2

HSPC, POPC, IO-806_02 and DSPE-PEG, taken in 55:35:5:5 mol % ratio, were dissolved in Chloroform. All lipid solutions were mixed homogeneously in round bottom flask and organic solvent was evaporated by rotary evaporator resulting in a thin lipid film. The lipid film was kept under high vacuum for 3-4 hr. It was, then, hydrated (by adding 5% Lactose solution to it) for 1.0 h at 60° C. in hot water bath. Next, hydrated nanoparticles were sequentially extruded through 400 nm, 200 nm and 100 nm pore size membrane held by filter support for 11 times at 60° C. using Avanti extruder supported over hot plate. It is evident from UV measurement that 4.0 mol % of IO-806_02 was encapsulated in the supramolecule. DLS measurement reveals average size of the nanoparticles to be 131.5 nm, PDI 0.064 and surface potential −24.8 mV. The resulting solution was lyophilized and stored at 4° C.

Formulation 3

HSPC, POPC, IO-803_01 and DSPE-PEG, taken in 55:35:5:5 mol % ratio, were dissolved in Chloroform. All lipid solutions were mixed homogeneously in round bottom flask and organic solvent was evaporated by rotary evaporator resulting in a thin lipid film. The lipid film was kept under high vacuum for 3-4 hr. It was, then, hydrated (by adding 5% Lactose solution to it) for 1.0 h at 60° C. in hot water bath. Next, hydrated nanoparticles were sequentially extruded through 400 nm, 200 nm and 100 nm pore size membrane held by filter support for 11 times at 60° C. using Avanti extruder supported over hot plate. It is evident from UV measurement that 4.1 mol % of IO-803_01 was encapsulated in the supramolecule. DLS measurement reveals average size of the nanoparticles to be 137.9 nm, PDI 0.058 and surface potential −24.5 mV. The resulting solution was lyophilized and stored at 4° C.

Formulation 4

HSPC, POPC, IO-801_03 and DSPE-PEG, taken in 50:35:10:5 mol % ratio, were dissolved in Chloroform. All lipid solutions were mixed homogeneously in round bottom flask and organic solvent was evaporated by rotary evaporator resulting in a thin lipid film. The lipid film was kept under high vacuum for 3-4 hr. It was, then, hydrated (by adding 5% Lactose solution to it) for 1.0 h at 60° C. in hot water bath. Next, hydrated nanoparticles were sequentially extruded through 400 nm, 200 nm and 100 nm pore size membrane held by filter support for 11 times at 60° C. using Avanti extruder supported over hot plate. It is evident from UV measurement that 9.4 mol % of IO-801_03 was encapsulated in the supramolecule. DLS measurement reveals average size of the nanoparticles to be 146.0 nm, PDI 0.043 and surface potential −28.2 mV. The resulting solution was lyophilized and stored at 4° C.

Formulation 5

HSPC, POPC, IO-801_02 and DSPE-PEG, taken in 50:30:15:5 mol % ratio, were dissolved in Chloroform. All lipid solutions were mixed homogeneously in round bottom flask and organic solvent was evaporated by rotary evaporator resulting in a thin lipid film. The lipid film was kept under high vacuum for 3-4 hr. It was, then, hydrated (by adding 5% Lactose solution to it) for 1.0 h at 60° C. in hot water bath. Next, hydrated nanoparticles were sequentially extruded through 400 nm, 200 nm and 100 nm pore size membrane held by filter support for 11 times at 60° C. using Avanti extruder supported over hot plate. It is evident from UV measurement that 6.3 mol % of IO-801_02 was encapsulated in the supramolecule. DLS measurement reveals average size of the nanoparticles to be 181.3 nm, PDI 0.137 and surface potential 3.46 mV. The resulting solution was lyophilized and stored at 4° C.

Example 3—Nanoparticles of BLZ-945-Lipid Conjugates

Figure 1B:
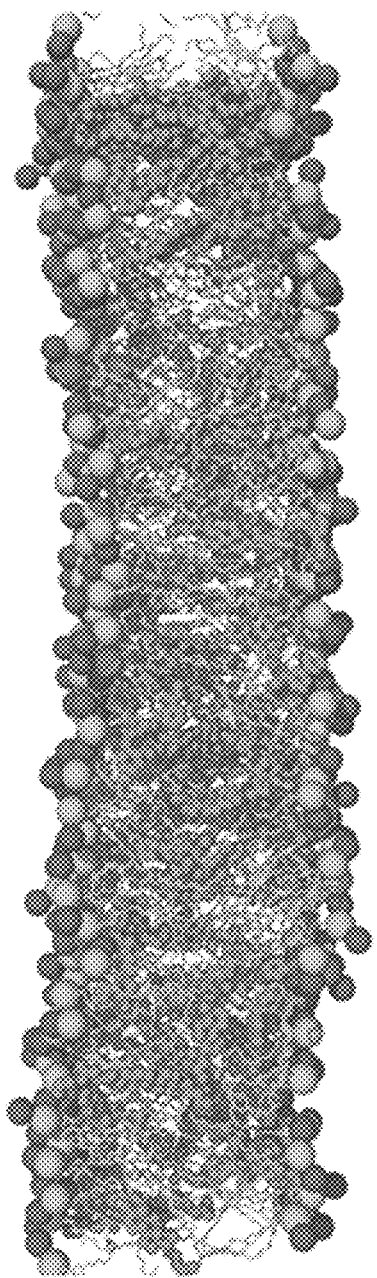
Figure 1C:
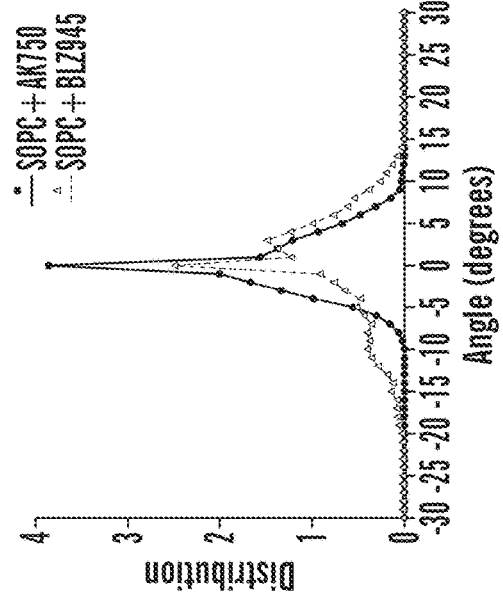
Figure 1D:
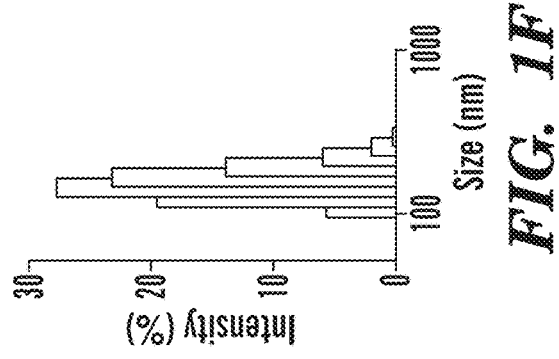
Figure 1E:
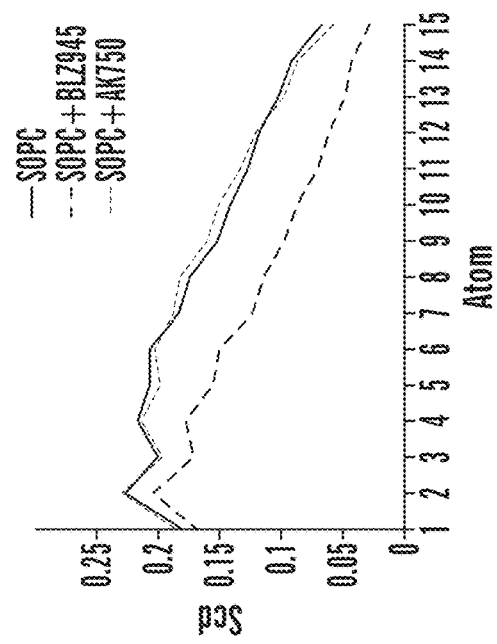
Figure 1F:
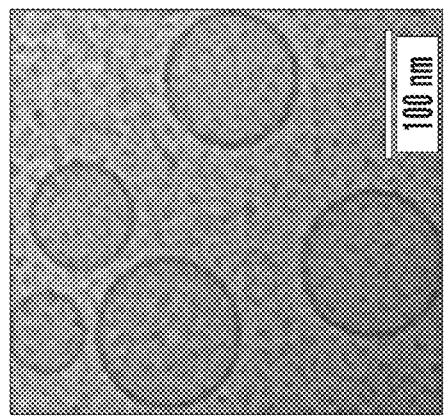

Nanoparticles of Compound BLN101 Unlike classical nanoparticles, or liposomes, where the drug is loaded in a carrier matrix, BLN1 facilitates the supramolecular assembly of the nanoparticle (termed AK750), meaning that stability of the structures at >20 mol % of the BLN101 is excellent. The quantum mechanical energy minimized structure of a CSF1R-inhibiting amphiphile is shown in FIG. 1b. Indeed, an all atomistic simulation of a lipid bilayer containing 20 mol % of BLN101 revealed the formation of a stable supramolecular structure, termed AK750 (FIG. 1c). Analysis of the deuterium order parameter, i.e. ordering of the lipid tail, as a measure of stability, revealed that the amphiphile resulted in a lipid tail ordering like that of a pure lipid-only bilayer (FIG. 1d). Furthermore, ripple formation is measured as a second measure of instability, which was quantified as the 'tilt' angle between vector joining center of mass of phospholipid tails and Z-axis (axis perpendicular to bilayer plane). A tilt angle of 0° is achieved means no ripples form, and a broad distribution indicates a large tilt angle and high bilayer instability. As shown in FIG. 1e, the AK750 bilayer showed a narrow distribution around a tilt angle of 0°, which further validated the stability. Figure if provides a representative high resolution Cryo-TEM image of BLN101 lipid nanoparticles fabricated with co-lipids (PC and DSPE-PEG). Further, the dynamic laser scattering of FIG. 1g shows the narrow size distribution of the nanoparticles with a hydrodynamic radii of 100-200 nm.

Example 4—Activity of BLZ-945-Lipid Conjugates

Activity Studies of Compound of Formula I

Efficacy of BLN101 vs BLZ945 on the ability to inhibit CSF1R in vitro is studied. RAW264.7 cells are treated with BLZ945 (67 nM) or BLN101 (67 nM) for different time points, at the end of which the cells were exposed to CSF1 (10 ng/ml) for 20 min. The cells were then lysed and analyzed for phosphorylated CSF1R levels. As shown in FIG. 2, BLN101 resulted in a sustained and statistically significantly greater inhibition of CSF1R as compared with BLZ945. Thus, activity studies have demonstrated that BLZ101 is a potent inhibitor of CSF1R.

iNOS is a marker for M1 macrophages. Efficacy of BLN101 (in formulation AK750) vs BLZ945 on increase in iNOS expression in vitro is studied. It is observed that exposure to Tumor Conditioned Media over 24 h decreases INOS levels. Measurement of the expression of iNOS in RAW264.7 cells at different time points after treatment with B-16-tumour conditioned media followed by BLZ-945 or BLN101 (as AK750 formulation) treatment across different time points. As shown in FIG. 3, AK750 results in enhanced iNOS expression, suggesting a switch to M1 phenotype from M2 phenotype.

Figure 4:
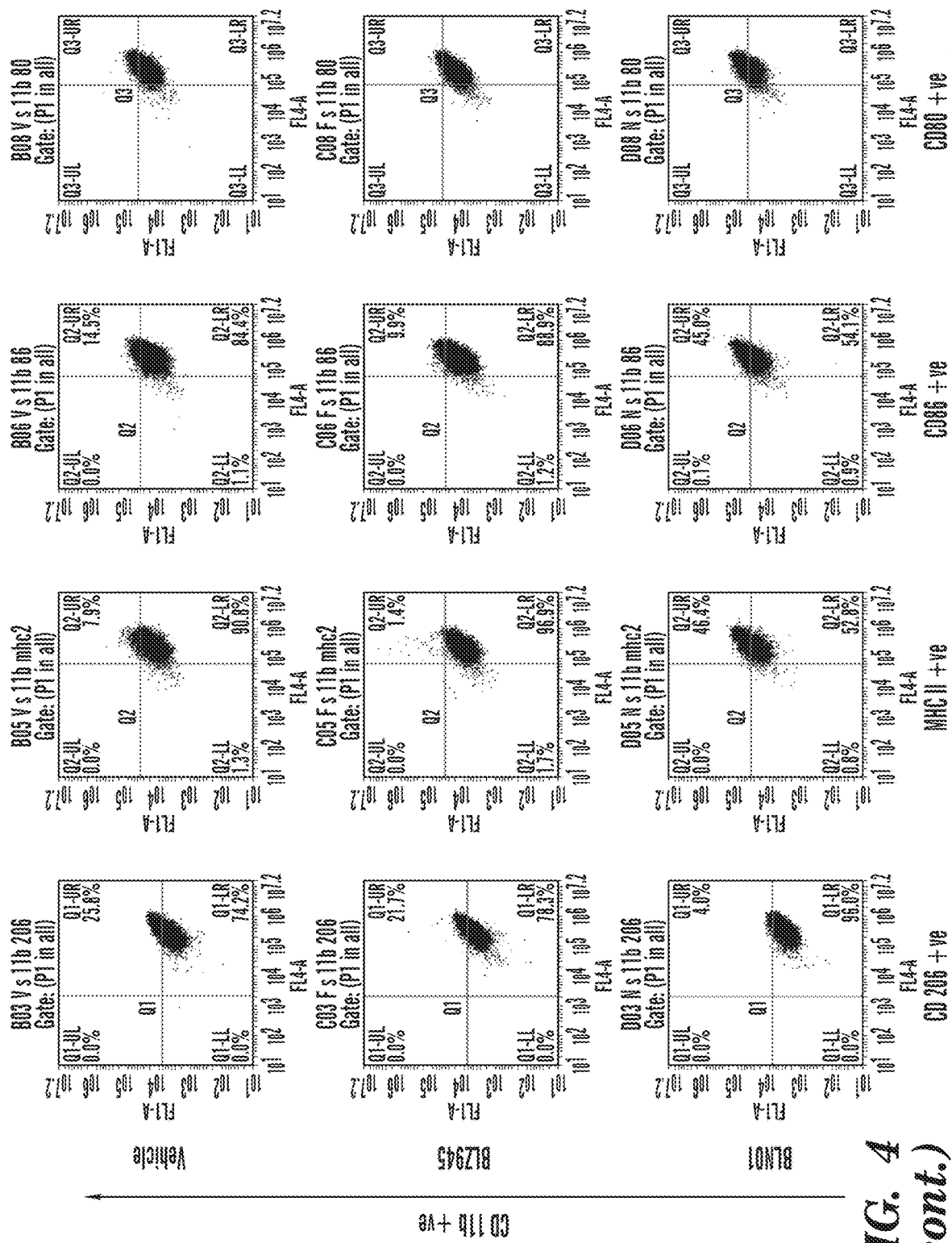
FIG. 4. Effect of BLZ-945 and BLN101 (formulated as AK750) in repolarization of the M2-macrophage phenotype formed upon stimulation with IL-4 to the M1-macrophage phenotype. Monocytes were treated with IL-4 for 24 hours, followed by which they were treated with BLZ-945 or BLN101 (formulated as AK750) in basal DMEM media, and cells were collected at different time points. M1 and M2 markers expression on the macrophages and their isotype control was evaluated separately by FACS. Graph represents the representative M1/M2 ratio by taking into account the various individual M1 and M2 markers that were analyzed using FACS. Data are representative of 3 separate experiments.

Efficacy of BLN101 to switch macrophages to a predominant M1 lineage is studied. Treatment of monocytes with IL4 is known to facilitate the differentiation of monocytes into macrophages. Further, activation of CSF1R skews it to a M2 phenotype. Monocytes are treated first with IL4 for 24 hours, and then exposed the cells to the CSF1R inhibitors, BLZ945 and BLN101 for 24 h. At different time points analysis of the cells for expression of markers CD11b+CD206+, CD11b+MHC-II+, CD11b+CD86+ and CD11b+CD80+ on the cells using flow cytometry. Results indicate that the treatment with BLN101 significantly increases the markers associated with M1 macrophages while reducing the M2 macrophage markers as compared with vehicle- or BLZ945 treatment. (FIG. 4). These results indicate that BLN101 is a more effective drug for facilitating the differentiation towards a M1 macrophage.

Figure 5A:
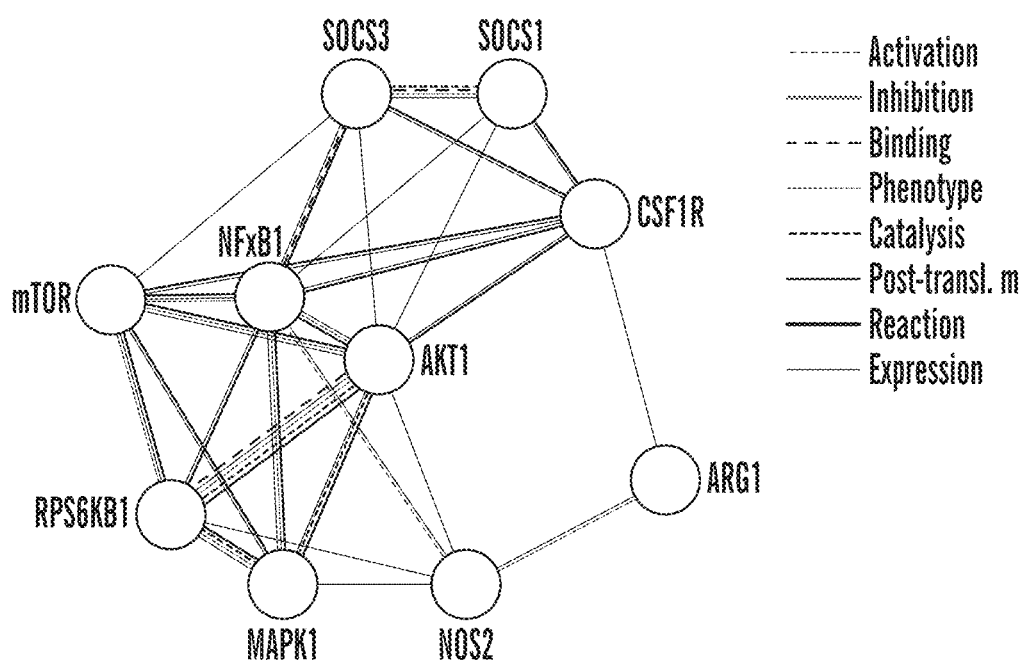
FIG. 5. Mechanistic insights into the efficacy of BLN101. (a-g) Mechanisms underlying the efficacy of BLN101 (administered as formulation AK750) (a) String map of the direct and indirect protein interactions with CSF1R. (b) The macrophages were incubated with AK750, BLZ945 or PLX3397 for 4 hours, and then exposed to MCSF for 2 h after a washout period of either 7 h (early time point) or 48 h (late time point). This allowed us to delineate the key pathways and dissect the persistent effects of the treatments post drug-washout. (c) Western blotting shows the effects of BLN101 (as formulation AK750) as compared with CSF1R inhibitors, BLZ945 and PLX3397, which are currently in the clinics for treatment of solid tumors. AK750 results in greater inhibition of specific downstream pathways over a longer period of time compared with other CSF1R inhibitors.
Figure 5B:
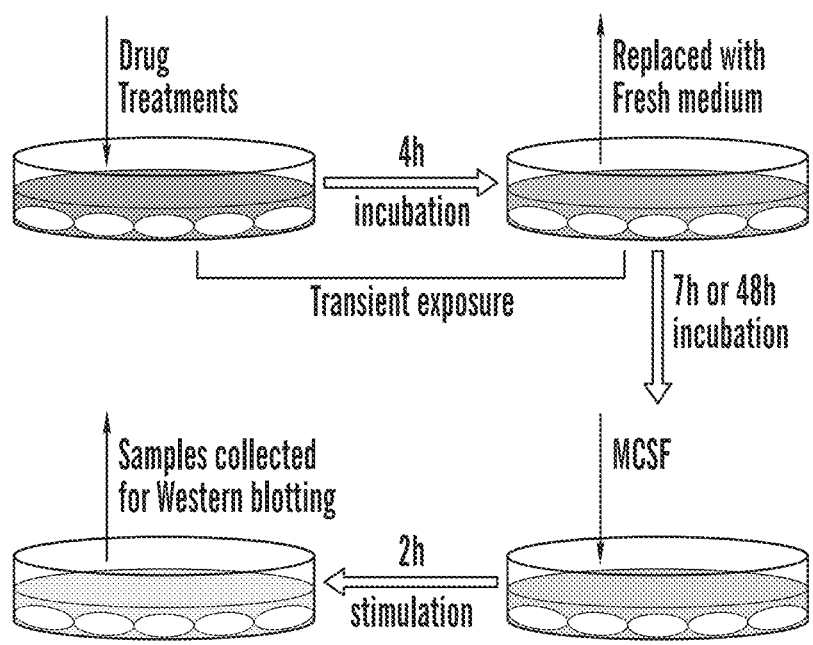
Figure 5C:
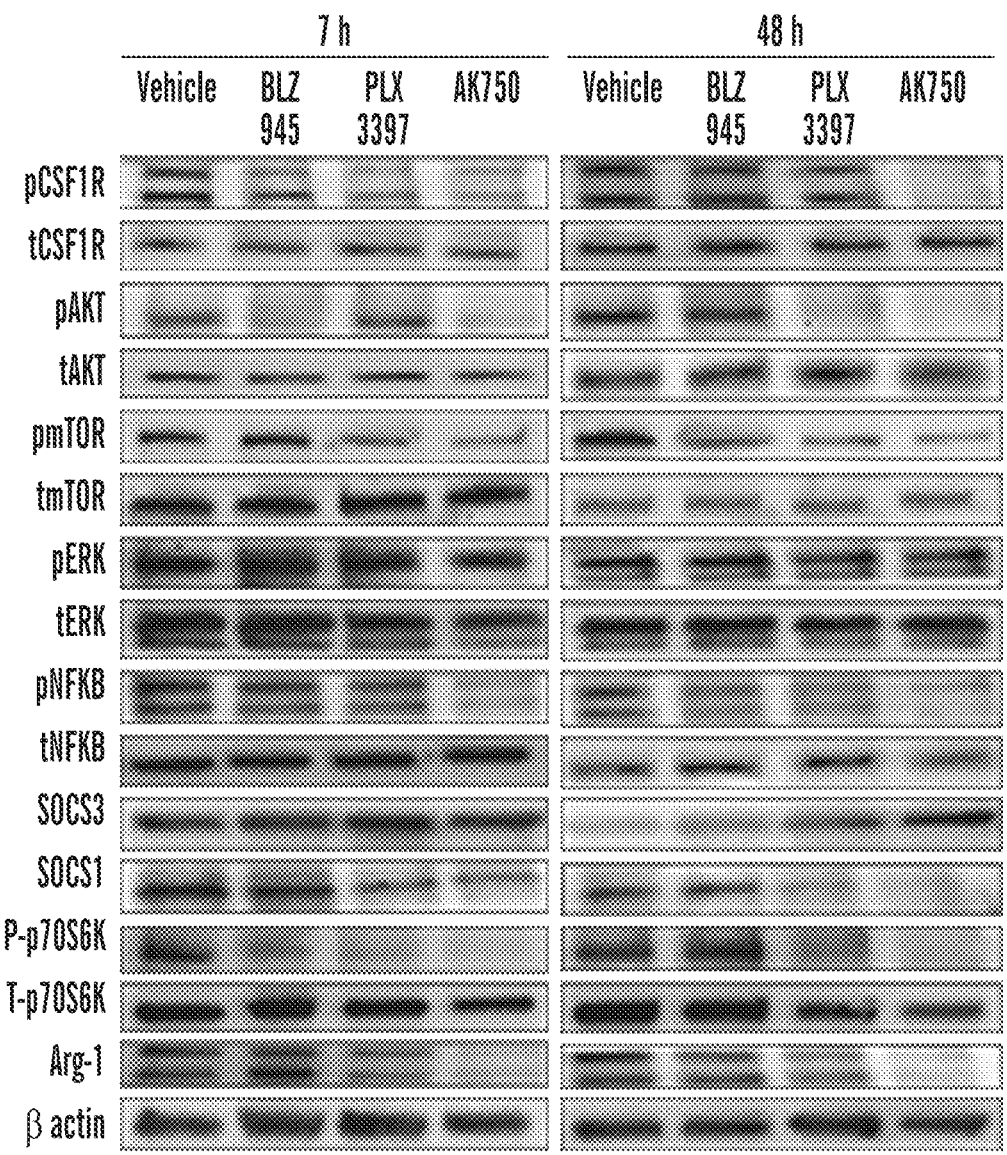
Figure 5D:
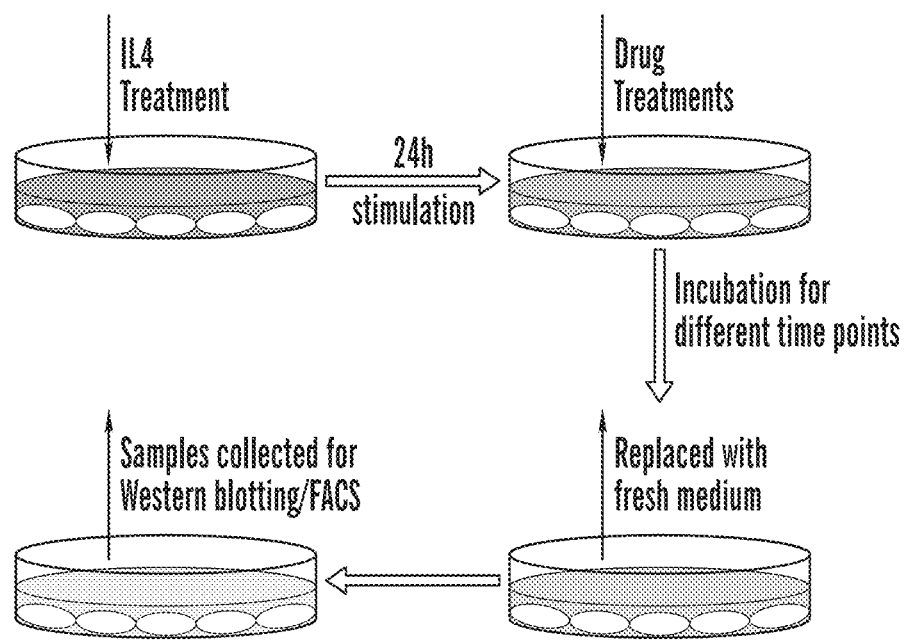
Figure 5E:
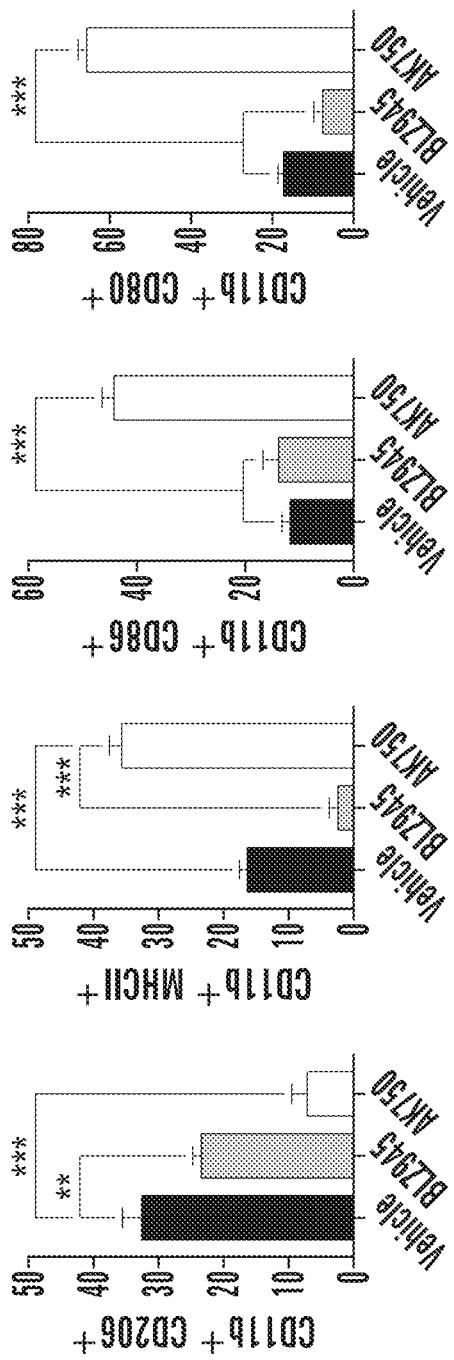
Figure 5F:
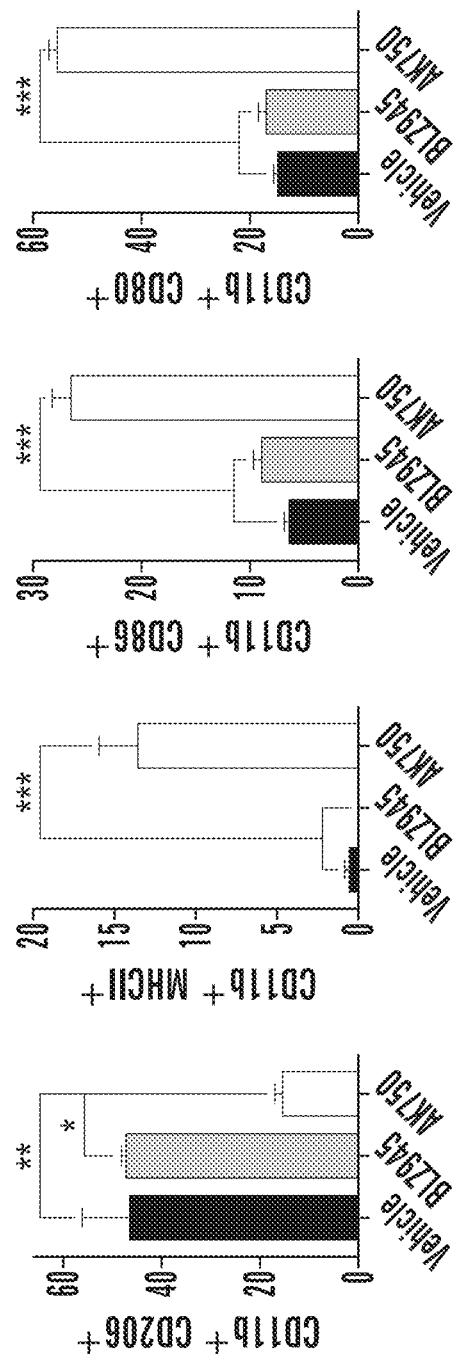
Figure 5G:
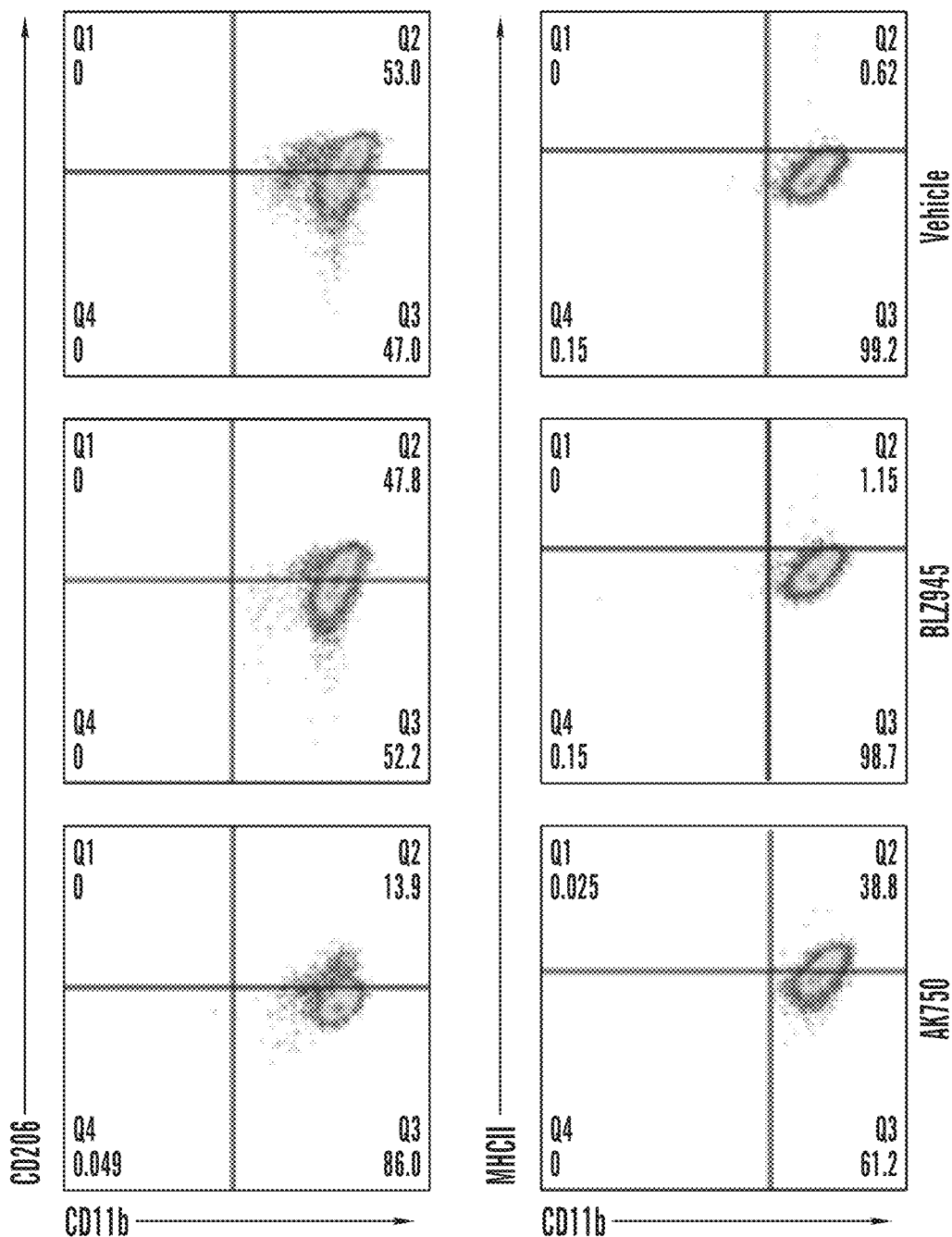

Mechanisms underlying the efficacy of BLN101 (administered as formulation AK750). A string map of the direct and indirect protein interactions with CSF1R (FIG. 5a) is studied the effects of different CSF1R inhibitors on these proteins. The macrophages were incubated with AK750, BLZ945 or PLX3397 for 4 hours, and then exposed to MCSF for 2 h after a washout period of either 7 h (early time point) or 48 h (late time point) (FIG. 5b). This allows to delineate the key pathways and dissect the persistent effects of the treatments post drug-washout. Both BLZ945 and PLX3397 are currently in the clinics for treatment of solid tumors. As shown in FIG. 5c, while PLX3397 and AK750 inhibited phosphorylation of CSF1R at 7 hours, only the latter was effective in inducing a complete inhibition at 48 h. Interestingly, the downstream signaling pathway that was dominantly ablated by AK750, but not by BLZ945 and PLX3397, in a sustained manner was the AKT-mTOR-p70S6K pathway. This is consistent with recent observations that PI3K acts as a macrophage switch between immune stimulation and suppression by inhibiting macrophage inflammatory responses. No effect on the MAPK signaling pathway is observed, although it is implicated in CSF1R signaling[21]. Additionally, AK750 resulted in a sustained, high suppressor of cytokine signaling (SOCS) 3 to SOCS1 ratio compared with BLXZ945 and PLX3397. In human tumor, expression of SOCS3 is associated with M1 polarizing environment and tumor kill, while SOCS1-expressing macrophages support tumor survival[22]. Compared with other treatments, AK750-treated macrophages also exhibited the highest iNOS to Arginase-1 ratio, which is a hallmark of M1 macrophages. SOCS1 is implicated in PI3K activity, which can mediate Arginase 1 expression in M2 macrophages, while SOCS3 blocks PI3K signaling. These results indicate that the blockade of CSF1R-signaling using AK750 polarizes the naïve macrophages to a M1 status. Treatment with the lymphokine IL4 can polarize a macrophage to a M2 state independent of CSF1 signaling. This offered the opportunity to test whether the sustained inhibition of CSF1R afforded by AK750 could repolarize a M2 macrophage to M1-like state, which cannot be probed by current short-acting inhibitors. The macrophages are incubated with IL4 for 24 hours to skew the macrophages to an M2 state, and then added the inhibitors for 4 hours. The cells are then washed, and maintained in fresh media for 12-72 hours. At different time-points, the cells are harvested and analyzed the population for M1 (MHCII+, CD86+, CD80+) or M2 (CD206+) markers using fluorescence activated cell sorting (FIG. 5d). As shown in FIG. 5e-g, treatment with AK750 resulted in a significant reduction in M2 phenotype and increase in M1 macrophages as early as 12 hours, which was sustained even at 72 hours. A reduction in M2 markers with BLZ945 at early time-points is observed, but this effect was lost at later time points. The incubation with BLZ945 did not increase the M1 markers. The FACS results were validated by Western blotting, which revealed that treatment with AK750 resulted in the highest SOCS3 to SOCS1 and INOS to Arg-1 ratio, indicating a skew towards M1 macrophage status. Mechanistically, AK750 reduced the baseline CSF1R activation and downstream PI3K signaling.

Figure 6A:
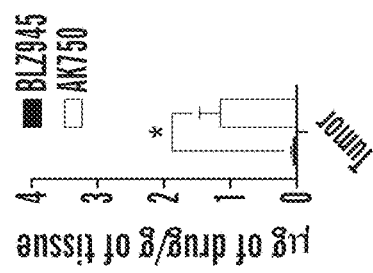
FIG. 6. Effect of BLN101 on tumor growth inhibition. (a) Representative image of tumor in an animal shows that a near-infrared dye-tagged supramolecule indeed distributed across the tumor with time. (b) Liquid chromatography-mass spectrometric (LC-MS) analysis revealed an almost 8× increase in AK750 concentration in the tumor as opposed to BLZ945 when both were administered at the same dose levels in animals. To validate the therapeutic efficacy of AK750, we randomly sorted mice bearing B16/F10 melanoma into three groups and treated each group with one of the following: blank vehicle (control); AK750; and BLZ945. The mice injected with vehicle formed large tumors by Day 10 (the day of first injection being Day 0), and consequently were killed. The animals in the other groups were also killed at the same time point to evaluate the effect of the treatments on tumor pathology. (c-d) Graph shows that while treatment with BLZ945 decreased tumor growth compared with vehicle-treated animals, treatment with AK750 resulted in complete inhibition of tumor growth. Changes in body weight were within the acceptable limits. (e) Western blot analysis of the tumors lysate revealed a complete inhibition of CSF1R phosphorylation in the tumors treated with AK750 (T1-3 are three representative tumors). (f) Quantitative analysis of the tumor-associated macrophages (TAMs) using FACS revealed that treatment with AK750 significantly reduced M2 macrophage markers (CCD206) and increased the M1 pool (MHCII+, CD80+, CD86+), which could mechanistically explain the in vivo efficacy.
Figure 6B:
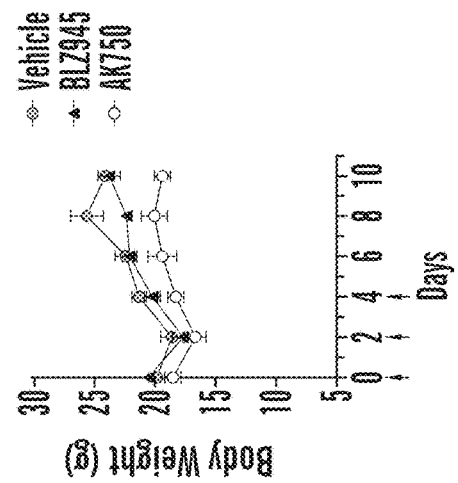
Figure 6C:
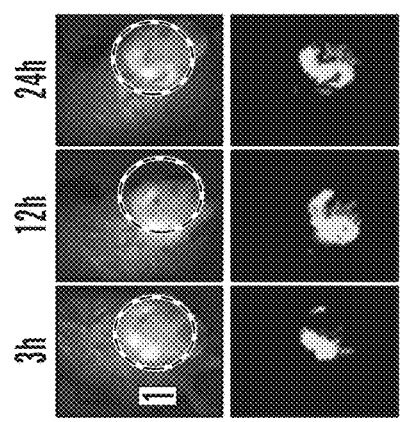
Figure 6D:
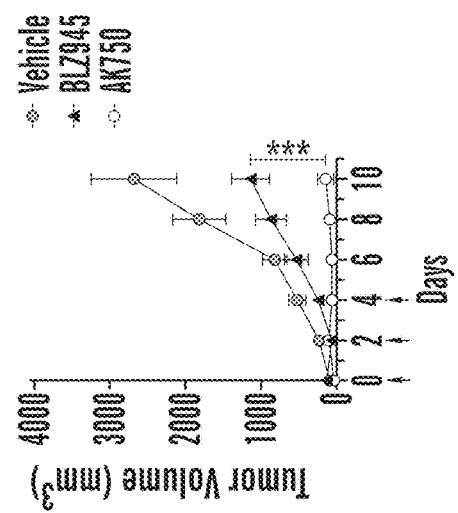

Studies to comprehend the translation of in vitro observations into in vivo efficacy: Initially, studies are carried out to test if these supramolecular structures preferentially home into tumors. It is observed that a near-infrared dye-tagged supramolecule indeed distributed across the tumor with time (FIG. 6a). Imaging the major organs revealed no signature from the kidney, heart or lungs. Liquid chromatography-mass spectrometric (LC-MS) analysis revealed an almost 8× increase in AK750 concentration in the tumor as opposed to BLZ945 when both were administered at the same dose levels in animals (FIG. 6b), suggesting that AK750 preferentially homes into tumors. Given the ability of BLN101 to switch macrophages and monocytes towards a M1 macrophage lineage, next study was carried to study the efficacy of BLN101 (administered as formulation AK750) on tumor growth. Study is carried with the drug in a B16/F10 melanoma model, which is highly immunogenic. Each tumor-bearing animal was injected with three doses of either Vehicle (for control group), 45 mg/kg of free BLZ-945, 45 mg/kg of BLN101 (in AK750 formulation) on day 0, day 4 and day 8. First day of treatment was considered as Day 0. As shown in FIG. 7c, treatment with BLN101 (as formulation AK750) was significantly more effective than BLZ-945. Additionally, nos adverse effects are observed as seen with no loss in body weight—this is consistent with the preferential accumulation into the tumor. Analysis of the excised tumors for CSF1R activation (i.e. phosphorylation of CSF1R) using Western blotting revealed that BLN101 (in AK750 formulation)-treated tumors result in a sustained and greater inhibition of CSF1R signaling compared to gold standard BLZ945 (FIG. 6e).

Later, macrophages are isolated from the tumors and analyzed the cells for expression of markers CD11b+CD206+, CD11b+MHC-II+, CD11b+CD86+ and CD11b+CD80+ on the cells using flow cytometry. Results indicate that the treatment with BLN101 (as AK750 formulation) significantly increases the markers associated with M1 macrophages while reducing the M2 macrophage markers as compared with vehicle, or BLZ945 treatment (FIG. 6f). These results indicate that BLN101 is a more effective anticancer drug than the current gold-standards, and exerts in action by facilitating the differentiation towards a M1 macrophage.

Validation of In vivo efficacy findings in a different tumor model Female Balb/c mice are used in a 4T1 breast cancer model. The tumor-bearing animals are injected with three doses of either Vehicle (for control group), 45 mg/kg of free BLZ-945, 45 mg/kg of BLN101 (in a AK750 formulation), or 25 mg/kg of CSF-1 neutralizing antibody, on day 0, day 4 and day 8. First day of treatment was considered as Day 0. Treatment with BLN101 (formulated as AK750) was found to be significantly more effective in inhibiting tumor progression than BLZ-945 and the CSF-1 neutralizing antibody (FIG. 7a). Furthermore, no changes in body weight of the animals are observed, indicating that the increased efficacy seen with BLN101 (in AK750 formulation) is not associated with any increased toxicity. This indicates that BLN101 has an improved therapeutic index. Number of metastatic nodules present in the lungs is also quantified. Lungs were harvested from the mice on day 12 following the above treatment, washed with cold PBS followed by which the number of metastatic nodules were counted. BLZ-945 showed a reduction as compared to CSF-1 neutralizing antibody and the vehicle control, However BLN101 displayed complete inhibition of formation of metastatic nodules (FIG. 7c). Furthermore, analysis of survival of the tumor-bearing animals revealed that the treatment with BLN101 (in AK750 formulation) resulted in a significant increase in survival as compared with BLZ945 treatment. Later, macrophages are isolated from the tumors and analyzed the cells for expression of markers CD11b+CD206+, CD11b+MHC-II+, CD11b+CD86+ on the cells using flow cytometry. Results indicate that the treatment with BLN101 (as AK750 formulation) significantly increases the markers associated with M1 macrophages (MHCII, CD86) while reducing the M2 macrophage markers (CD206) as compared with vehicle, or BLZ945 treatment (FIG. 7e). These results indicate that BLN101 is a more effective anticancer drug than the current gold-standards, and exerts in action by facilitating the differentiation towards a M1 macrophage.

Effect of combination of BLN101 and anti-SIRPα antibody formulated in a single formulation: study is carried to understand whether a composition, where an antibody that blocks SIRPα on macrophages and BLN101 combined in a single supramolecular structure could exert a greater efficacy as compared with BLN101 alone. SIRPα is a 'eat-me-not' signaling, which cancer cells engage with a CD47 ligand, and prevents phagocytosis of the cancer cells. The antibody that inhibits SIRPα was conjugated to the PEG chains on the surface of the AK750 supramolecular nanoparticles. A non-specific IgG was used as controls. As shown in FIG. 8a-b, the SIRPα-conjugated AK750 bound preferentially to macrophages. Furthermore, melanoma-bearing mice is treated with a single dose of SIRPα antibody, AK750 or the SIRPα-AK750. As shown in FIG. 8c, one single dose of SIRPα-AK750 exerted a significant synergistic inhibition of tumor growth.

[i] (a) Chapman P B, Hauschild A, Robert C, Haanen J B, Ascierto P, Larkin J, et al. Improved survival with vemurafenib in melanoma with BRAF V600E mutation. N Engl J Med. 2011; 364(26):2507-16.
(b) Flaherty K T, Puzanov I, Kim K B, Ribas A, McArthur G A, Sosman J A, et al. Inhibition of mutated, activated BRAF in metastatic melanoma. N Engl J. Med. 2010; 363(9):809-19. (c). Sosman J A, Kim K B, Schuchter L, Gonzalez R, Pavlick A C, Weber J S, et al. Survival in BRAF V600-mutant advanced melanoma treated with vemurafenib. N Engl J Med. 2012; 366(8):707-14. (d). Flaherty K T, Robert C, Hersey P, Nathan P, Garbe C, Milhem M, et al. Improved survival with MEK inhibition in BRAF-mutated melanoma. N Engl J Med. 2012; 367 (2):107-14.

[ii] (a) Gabrilovich D I, Nagaraj S. Myeloid-derived suppressor cells as regulators of the immune system. Nat Rev Immunol. 2009; 9(3): 162-74. (b). Schreiber R D, Old L J, Smyth M J. Cancer immunoediting: integrating immunity's roles in cancer suppression and promotion. Science. 2011; 331(6024):1565-70.
(c). Kerkar S P, Restifo N P. Cellular constituents of immune escape within the tumor microenvironment. Canc Res. 2012; 72(13):3125-30.

[iii] (a) Dai X M, Ryan G R, Hapel A J, Dominguez M G, Russell R G, Kapp S, et al. Targeted disruption of the mouse colony-stimulating factor 1 receptor gene results in osteopetrosis, mononuclear phagocyte deficiency, increased primitive progenitor cell frequencies, and reproductive defects. Blood. 2002; 99(1): 111-20. (b). Li J, Chen K, Zhu L, Pollard J W. Conditional deletion of the colony stimulating factor-1 receptor (c-fms proto-oncogene) in mice. Genesis. 2006; 44(7):328-35.

[iv] Qian B Z, Pollard J W. Macrophage diversity enhances tumor progression and metastasis. Cell 2010; 141:39-51;

[v] Tang R, Beuvon F, Ojeda M, Mosseri V, Pouillart P, Scholl S. M-CSF (monocyte colony stimulating factor) and M-CSF receptor expression by breast tumour cells: M-CSF mediated recruitment of tumour infiltrating monocytes? J Cell Biochem 1992; 50:350-6;

[vi] Lin E Y, Gouon-Evans V, Nguyen A V, Pollard J W. The macrophage growth factor CSF-1 in mammary gland development and tumor progression. J Mammary Gland Biol Neoplasia 2002; 7:147-62)

[vii] (a) Douglass T G, Driggers L, Zhang J G, Hoa N, Delgado C, et al. Macrophage colony stimulating factor: not just for macrophages anymore! A gateway into complex biologies. Int Immunopharmacol. 2008; 8:1354-1376. (b). Lin H, Lee E, Hestir K, Leo C, Huang M, et al. Discovery of a cytokine and its receptor by functional screening of the extracellular proteome. Science. 2008; 320: 807-811. (c). Stanley E R, Chitu V CSF-1 receptor signaling in myeloid cells. Cold Spring Harb Perspect Biol. 2014; 6. (d) Rovida E, Sbarba P D Colony-Stimulating Factor-1 Receptor in the Polarization of Macrophages: A Target for Turning Bad to Good Ones? J Clin Cell Immunol. 2015; 6: 379. doi:10.4172/2155-9899.1000379.

[viii] Sutton, James C.; Wiesmann, Marion; Wang, Weibo; Lindvall, Mika K.; Lan, Jiong; Ramurthy, Savithri; Sharma, Anu; Mieuli, Elizabeth J.; Klivansky, Liana M.; Lenahan, William P.; et al. Preparation of 6-O-substituted benzoxazole and benzothiazole compounds for inhibiting CSF-1R signalling. PCT Int. Appl. (2007), WO 2007121484 A2 20071025.

[ix] Sengupta, S.; Roy, M.; Sarkar, A.; Hossain, Sk S.; Sengupta, A.; Dutta, P. K.; Ansari, A.; Mandal, S. K. Preparation of lipid-based platinum compounds and nanoparticles useful in the treatment of cancer. PCT Int. Appl. (2014), WO 2014201376 A2 20141218.

We claim:
1. A compound of Formula I:

Formula I wherein, 'Xa' is:

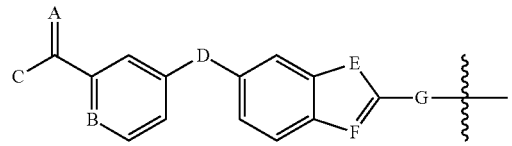

C=hydroxy, alkyl group, aryl group, cycloalkyl group
A=O, NH, S
B=CH, N
D=C, O, NH, S
E=O, NH, S
F=CH, N
G=C, O, NH, S
'Xb' is:

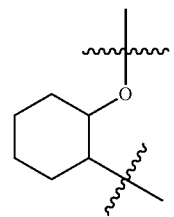 [SMILES: *OC1CCCCC1*]

'Z' is a linker joining 'Xb' with 'L'; and
'L' is a lipid, a lipid derivative or a lipid conjugate or any combination thereof; or
any salt, tautomeric form, polymorph, or solvate of compound of Formula I thereof.

2. The compound of claim 1, wherein the linker is selected from the group consisting of a direct bond, oxygen, sulfur, $NR^1$, C(O), C(O)O, C(O)$NR^1$, SO, $SO_2$, $SO_2NH$, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

3. The compound of claim 1, wherein the linker comprises at least one cleavable group.

4. The compound of claim 1, wherein the linker consists of succinic acid, fumaric acid, propargylic acid, ethylene glycol, diethylene glycol, or natural or unnatural amino acids, or any combination thereof; or wherein the linker comprises at least one of oxalic acid, malonic acid, glutaric acid, ethylene diamine, ethylene glycol, diethylene glycol, acetic acid, propionic acid, butyric acid, valeric acid, acrylic acid, but-2-enoic acid, pent-2-enoic acid, hex-2-enoic acid, 2-propynoic acid, but-2-ynoic acid, pent-2-ynoic acid, hex-2-ynoic acid, ethylene, propylene, 1-butene, 1-pentene, 1-hexene, acetylene, propyne, but-1-yne or pent-1-yne, or any combination thereof.

5. The compound of claim 1, wherein the linker is selected from the group consisting of —C(O)CH₂CH₂C(O)—; —C(O)(CH₂CH₂)ₘC(O)(OCH₂CH₂)ₙ—, wherein 'n' is 1 to 10 and 'm' is 1 to 4; —C(O)(CH₂)ₓCH₂C(O)NH(CH₂CH₂)ₙ—, wherein 'n' is 1 to 10 and 'x' is 0 to 3; —C(O)(CH₂)ₘCH₂C(O)NH(CH₂CH₂)ₙNHC(O)—, wherein 'n' is 1 to 10 and 'm' is 1 to 4; —C(O)CH₂(CH₂)ₘC(O)NH—, wherein 'm' is 1 to 4; —C(O)(CH₂)ₙCH₂(R)NHC(O)—, wherein 'n' is 1 to 10 and R is H, alkyl, acid, amine, aryl, or thiol; —C(O)(CH₂)ₙCH₂(R)NHC(O)—, wherein 'n' is 1 to 10 and R is H, alkyl, acid, amine, aryl or thiol; C(O)(CH₂(R)CH₂)ₙC(Y)X—, wherein 'n' is 1 to 10, R is H, alkyl, acid, amine, aryl or thiol, Y is C, O, NH, S, and X is C, O, NH, S; —C(O)CH₂CH₂NHC(O)—; —C(O)CH₂CH₂C(O)NHCH₂CH₂NHC(O)—; —C(O)CH₂CH₂C(O)NHCH₂NHC(O)—; —C(O)CH₂OCH₂CH₂—; —C(O)CH₂CH₂OCH₂CH₂—; —C(O)CH₂OCH₂CH₂OCH₂CH₂—; —C(O)CH(R)NHC(O)CH₂—, wherein R is H, CH₃, CH(CH₃)₂, CH₂CH(CH₃)₂, C(CH₃)CH₂CH₃, or CH₂-Phenyl; —C(O)CH(R)NHC(O)CH₂CH₂—, wherein R is H, CH₃, CH(CH₃)₂, CH₂CH(CH₃)₂, C(CH₃)CH₂CH₃, or CH₂-Phenyl; —C(O)CH(R)NHC(O)(CH₂)ₙC(O)—, wherein R is H, CH₃, CH(CH₃)₂, CH₂CH(CH₃)₂, C(CH₃)CH₂CH₃, or CH₂-Phenyl, and 'n' is 1, 2, or 3; —C(O)CH(R)NHC(O)CH₂OCH₂CH₂—, wherein R is H, CH₃, CH(CH₃)₂, CH₂CH(CH₃)₂, C(CH₃)CH₂CH₃, or CH₂-Phenyl; —C(O)C≡C(CH₂)ₙ—C(O)—, wherein 'n' is 1, 2 or 3; —C(O)C≡C(CH₂)ₙ—, wherein 'n' is 0, 1, or 2; —C(O)CH═CH(CH₂)ₙC(O)—, wherein 'n' is 0, 1, 2, or 3; —C(O)CH═CH(CH₂)ₙ—, wherein 'n' is 1, 2, or 3; and —C(O)CH₂CH₂C(O)NHCH₂C(O)—.

6. The compound of claim 1, wherein the lipid, lipid derivative or lipid conjugate is selected from the group consisting of cholesterol, cholesterol derivatives, oleic acid, oleic acid derivative, alpha tocopherol, alpha tocopherol derivatives, phospholipid, phospholipid derivatives, fatty acid, naturally occurring lipid molecule which is conjugated to drug molecules, 1,3-Propanediol Dicaprylate/Dicaprate, 10-undecenoic acid, 1-dotriacontanol, 1-heptacosanol, 1-nonacosanol, 2-ethyl hexanol, Androstanes, Arachidic acid, Arachidonic acid, arachidyl alcohol, Behenic acid, behenyl alcohol, glyceryl monocaprate, Capric acid, capric alcohol, capryl alcohol, Caprylic acid, Caprylic/Capric Acid Ester of Saturated Fatty Alcohol C12-C18, Caprylic/Capric Triglyceride, Caprylic/Capric Triglyceride, Ceramide phosphorylcholine (Sphingomyelin, SPH), Ceramide phosphorylethanolamine (Sphingomyelin, Cer-PE), Ceramide phosphorylglycerol, Ceroplastic acid, Cerotic acid, Cerotic acid, ceryl alcohol, Cetearyl alcohol, Ceteth-10, cetyl alcohol, Cholanes, Cholestanes, cholesterol, cis-11-eicosenoic acid, cis-11-octadecenoic acid, cis-13-docosenoic acid, cluytyl alcohol, Dihomo-γ-linolenic, Docosahexaenoic acid, egg lecithin, Eicosapentaenoic acid, Eicosenoic acid, Elaidic acid, elaidolinolenyl alcohol, elaidolinoleyl alcohol, elaidyl alcohol, Erucic acid, erucyl alcohol, Estranes, Ethylene glycol distearate (EGDS), Geddic acid, geddyl alcohol, glycerol distearate (type I) EP, Glycerol Tricaprylate/Caprate; Glycerol Tricaprylate/Caprate; glyceryl monocaprylate, Glyceryl Triacetate, Glyceryl Tricaprylate, Glyceryl Tricaprylate/Caprate/Laurate, Glyceryl Tricaprylate/Tricaprate, glyceryl tripalmitate (Tripalmitin), Henatriacontylic acid, Heneicosyl alcohol, Heneicosylic acid, Heptacosylic acid, Heptadecanoic acid, Heptadecyl alcohol, Hexatriacontylic acid, isostearic acid, isostearyl alcohol, Lacceroic acid, Lauric acid, Lauryl alcohol, Lignoceric acid, lignoceryl alcohol, Linoelaidic acid, Linoleic acid, linolenyl alcohol, linoleyl alcohol, Margaric acid, Mead, Melissic acid, melissyl alcohol, Montanic acid, montanyl alcohol, myricyl alcohol, Myristic acid, Myristoleic acid, Myristyl alcohol, neodecanoic acid, neoheptanoic acid, neononanoic acid, Nervonic, Nonacosylic acid, Nonadecyl alcohol, Nonadecylic acid, Nonadecylic acid, Oleic acid, oleyl alcohol, Palmitic acid, Palmitoleic acid, palmitoleyl alcohol, Pelargonic acid, pelargonic alcohol, Pentacosylic acid, Pentadecyl alcohol, Pentadecylic acid, Phosphatidic acid (phosphatidate, PA), Phosphatidylcholine (lecithin, PC), Phosphatidylethanolamine (cephalin, PE), Phosphatidylinositol (PI), Phosphatidylinositol bisphosphate (PIP2), Phosphatidylinositol phosphate (PIP), Phosphatidylinositol triphosphate (PIP3), Phosphatidylserine (PS), polyglyceryl-6-distearate, Pregnanes, Propylene Glycol Dicaprate, Propylene Glycol Dicaprylocaprate, Propylene Glycol Dicaprylocaprate, Psyllic acid, recinoleaic acid, recinoleyl alcohol, Sapienic acid, soy lecithin, Stearic acid, Stearidonic, stearyl alcohol, Tricosylic acid, Tridecyl alcohol, Tridecylic acid, Triolein, Undecyl alcohol, undecylenic acid, Undecylic acid, Vaccenic acid, α-Linolenic acid, and γ-Linolenic acid via a spacer, wherein the spacer is selected from the group consisting of aliphatic dicarboxylic acid, unsaturated dicarboxylic acid, aldaric acid, fumaric acid, propargylic acid, acetylene dicarboxylic acid, aromatic/hetero aromatic dicarboxylic acid, ethylene glycol, diethylene glycol, natural or unnatural amino acids, and any combinations thereof.

7. The compound of claim 1, wherein the lipid conjugate is the lipid or the lipid derivative conjugated with a compound selected from the group consisting of CSF-1R inhibitor, a kinase inhibitor, a chemotherapeutic drug, an immunomodulator and any combination thereof.

8. The compound of claim 7, wherein the immunomodulator is an antibody, a cytokine or a combination thereof.
9. The compound of claim 1, wherein said compound is compound of Formula 23:
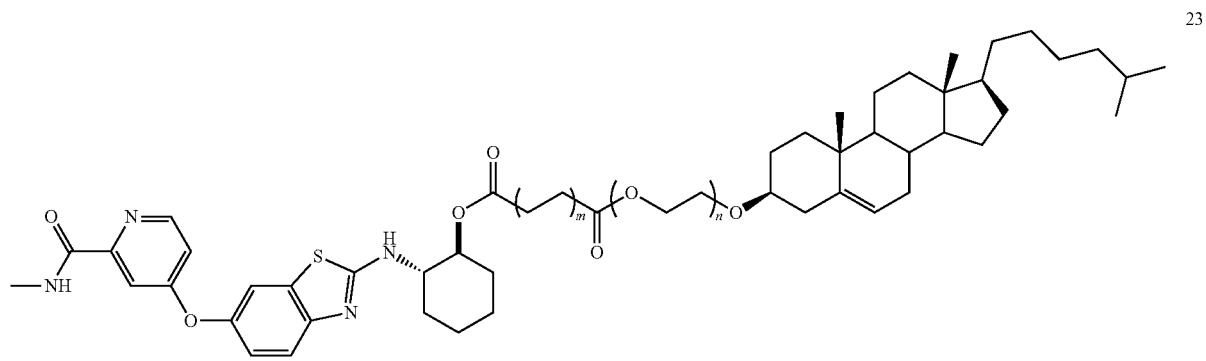
23
wherein 'n' is 1 to 10 and 'm' is 1 to 4;
said compound is compound of Formula 24:
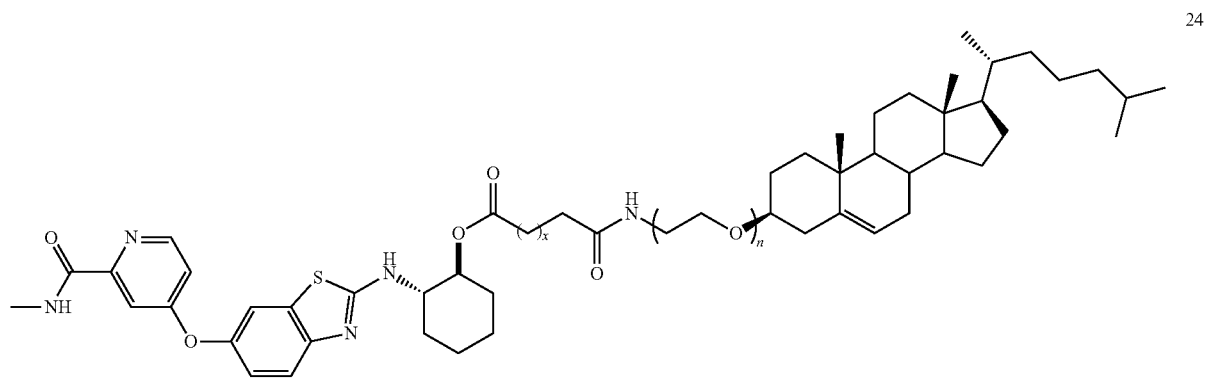
24
wherein 'n' is 1 to 10 and 'x' is 0 to 3;
said compound is compound of Formula 25:
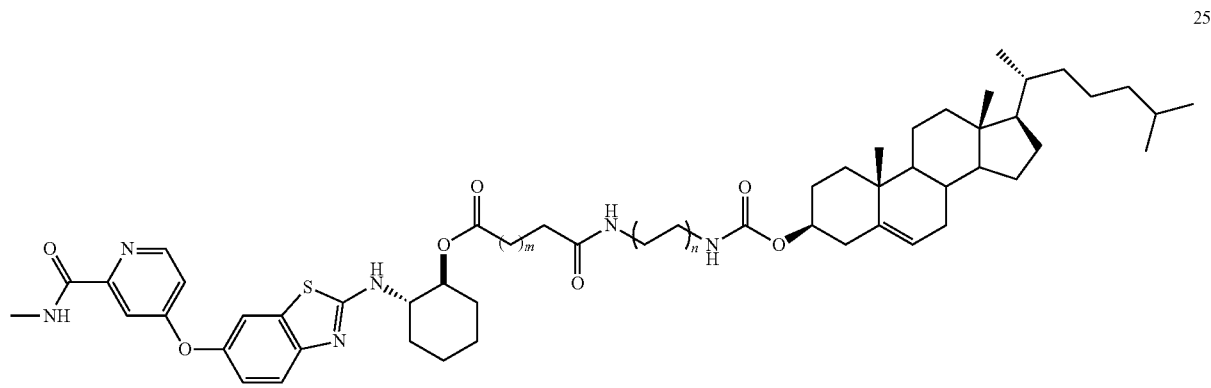
25 wherein 'n' is 1 to 10 and 'm' is 1 to 4;
said compound is compound of Formula 26:
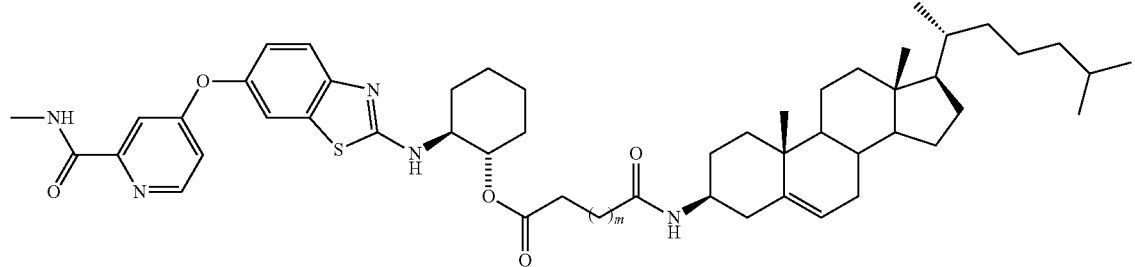
wherein 'm' is 1 to 4; or
said compound is compound of Formula 27:
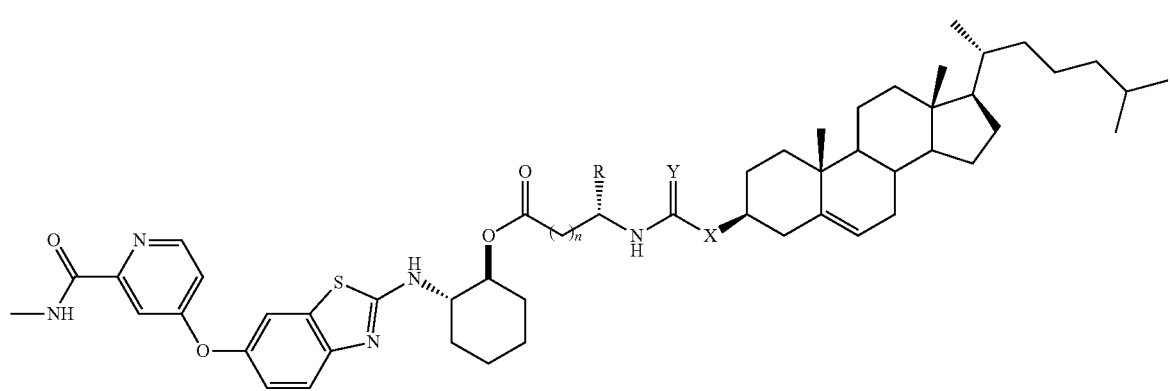
wherein 'n' is 1 to 10; R is H, alkyl, acid, amine, aryl or thiol; Y is C, O, NH, or S; and X is O, NH, or S.
10. The compound of claim 1 selected from:
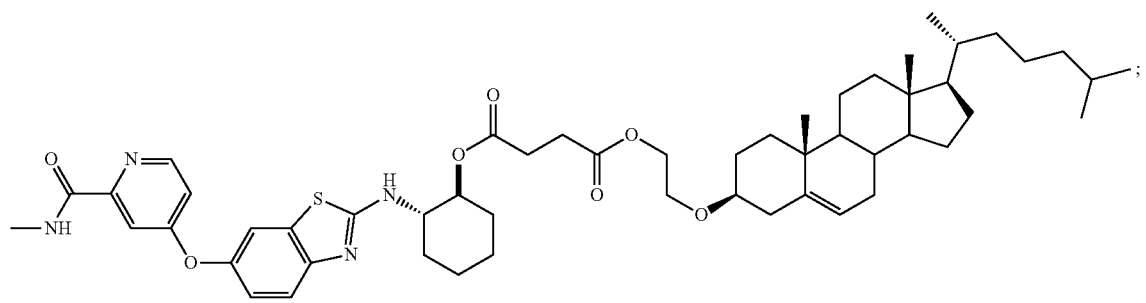
IO-801_01
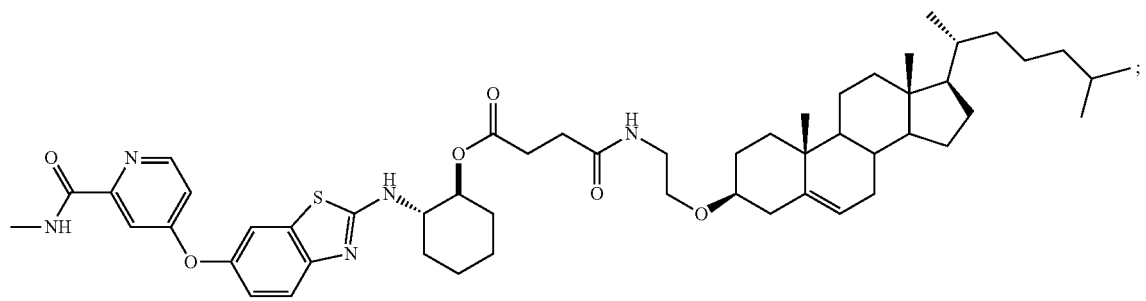
IO-801_02

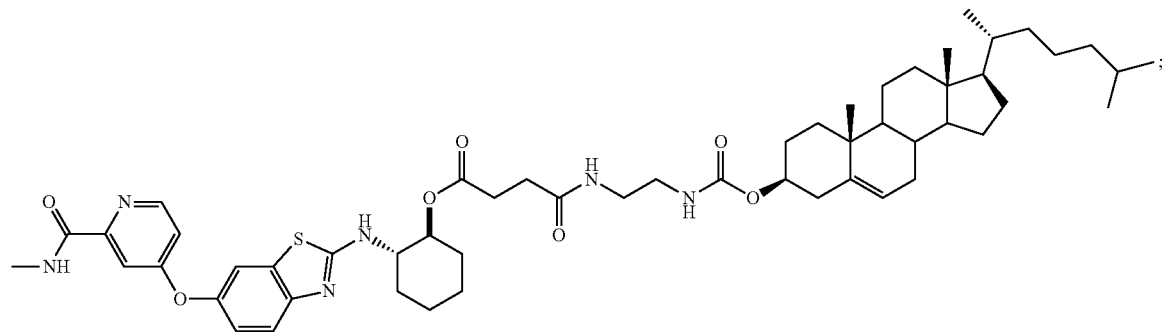
IO-801_03
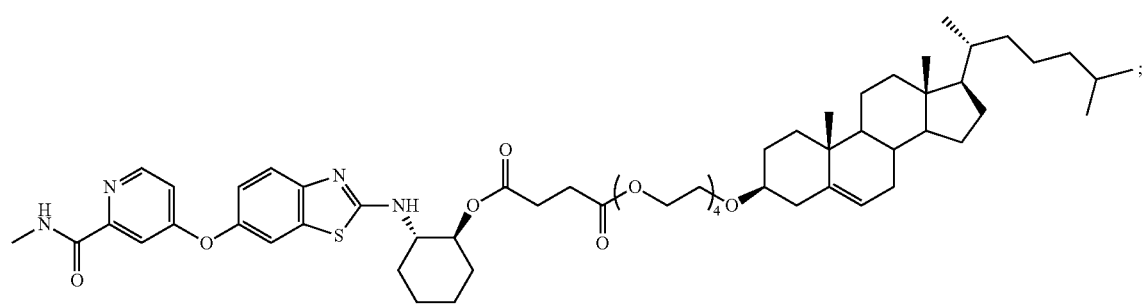
IO-806_01
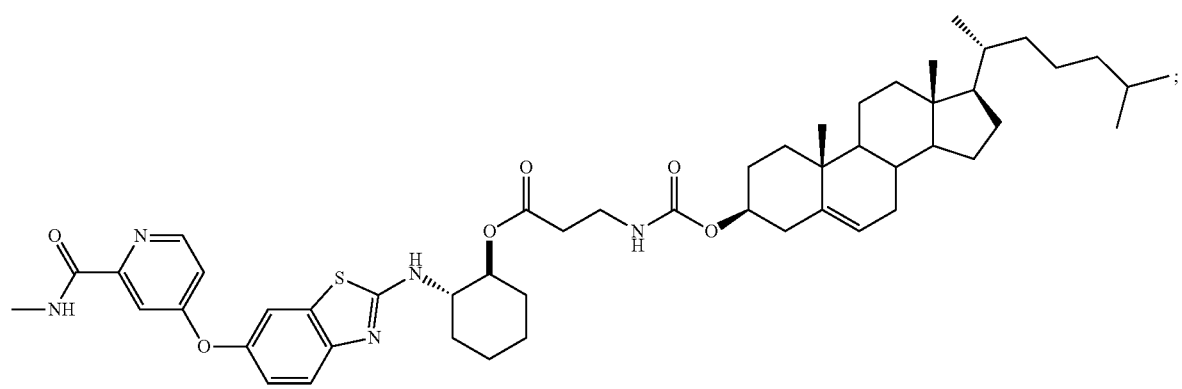
IO-806_02
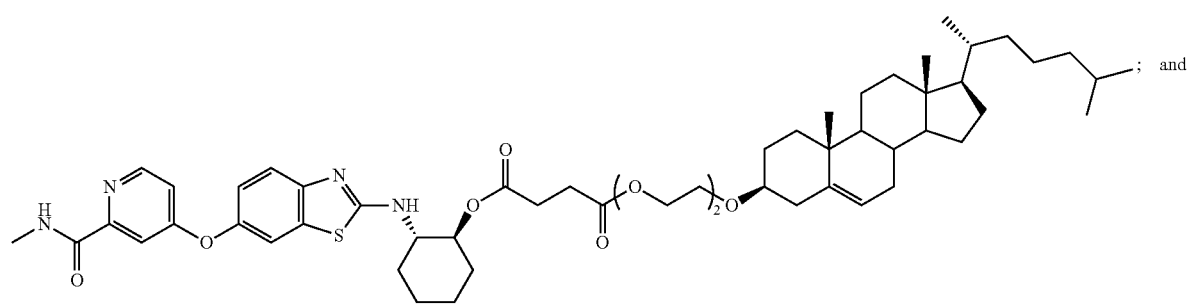
IO-806_03
; and -continued

BLN101

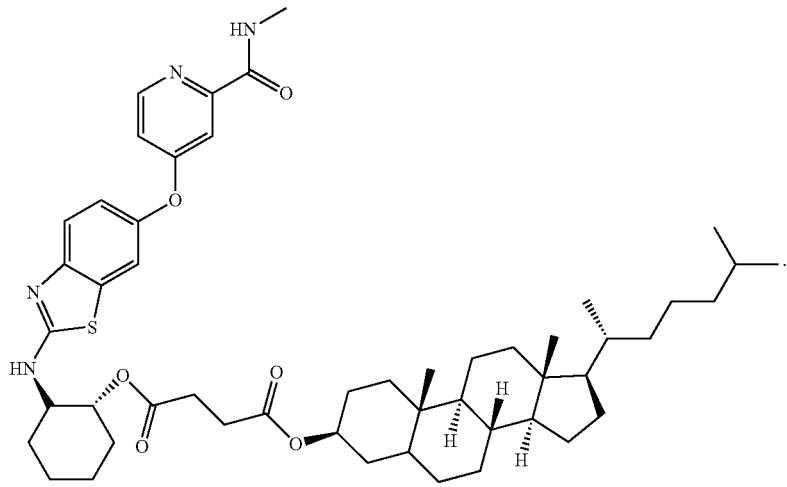

11. A composition comprising a compound of Formula I:

Formula I wherein, 'Xa' is:

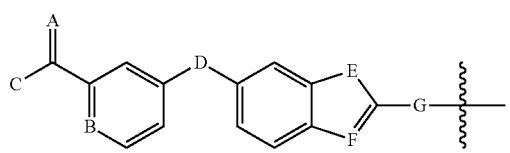

C=hydroxy, alkyl group, aryl group, cycloalkyl group
A=O, NH, S
B=CH, N
D=C, O, NH, S
E=O, NH, S
F=CH, N
G=C, O, NH, S
'Xb' is:

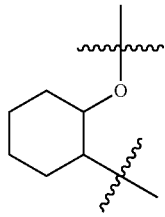

'Z' is a linker joining 'Xb' with 'L'; and
'L' is a lipid, a lipid derivative or a lipid conjugate or any combinations thereof;
or
any salt, tautomeric form, polymorph, or solvate of compound of Formula I thereof; along with pharmaceutically acceptable excipient.

12. The composition of claim 11, wherein the composition further comprises a kinase inhibitor, a chemotherapeutic agent or an immunomodulator or any combination thereof or wherein the composition further comprises a co-lipid.

13. The composition of claim 12, wherein the chemotherapeutic agent is selected from the group consisting of PI3K inhibitors; platinum compounds; inhibitors of topoisomerase I and II; alkylating agents; microtubule inhibitors; and angiogenesis inhibitors; or any combination thereof.

14. The composition of claim 12, wherein the chemotherapeutic agent is conjugated with a component of the composition.

15. The composition of claim 11, wherein the composition is a liposome, emulsion, or micelle or a nanoparticle.

16. A method of treating cancer comprising administering a compound of Formula I of claim 1 or salt, tautomeric form, polymorph, or solvate thereof, to a subject in need of treatment for cancer.

17. A method for inhibition of CSF or CSF-1R signalling pathway in a cell, wherein said method comprises contacting the cell with a compound of Formula I of claim 1 or salt, tautomeric form, polymorph, or solvate thereof.

18. A process for preparing a compound of Formula I of claim 1, said process comprising the steps of:
reacting a lipid, a lipid derivative or a lipid conjugate or any combination thereof, with a linker to obtain a molecule I;
reacting the molecule I with 'alicyclic derivative of N-Boc amino-alcohol' to obtain a molecule II; and
reacting the molecule II with 'compound 22' to obtain a compound of Formula I;
wherein
said 'alicyclic derivative of N-Boc amino-alcohol' is:

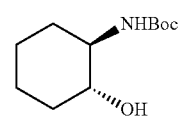

wherein said compound 22 is:

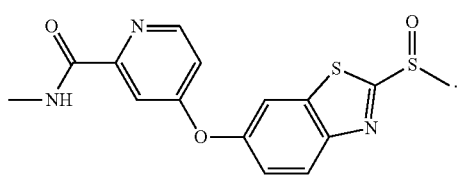

and
wherein said compound of Formula 16 is:

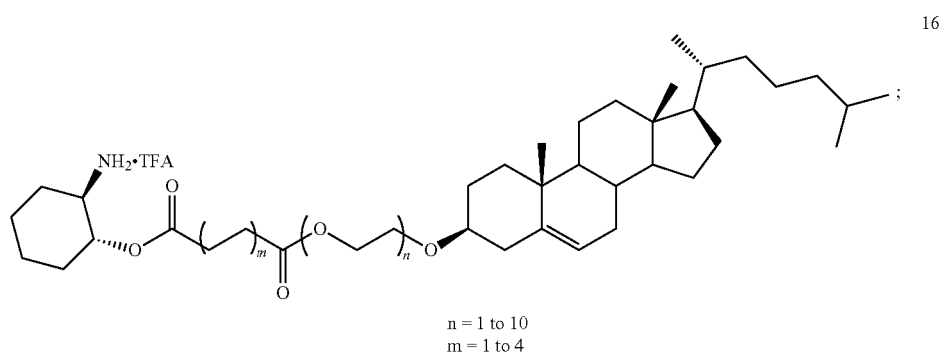

19. A process for preparing a compound of Formula 23-27 or the compound BLN-101, wherein:

i) the process for preparing a compound of Formula 23 comprises the steps of:

reacting a compound of Formula 4 with alicyclic derivative of N-Boc amino-alcohol followed by deprotection using Trifluoro acetic and dichloromethane to obtain a compound of Formula 16, wherein said compound of Formula 4 is:

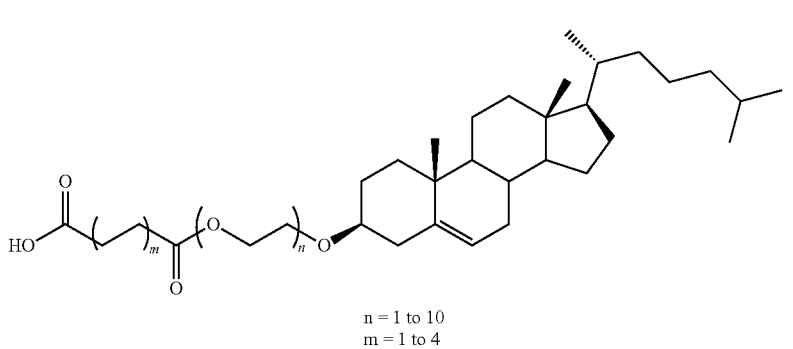

and
reacting the compound of Formula 16 with the compound of Formula 22 to obtain the compound of Formula 23;

ii) the process for preparing a compound of Formula 24 comprises the steps of:

reacting a compound of Formula 8 with alicyclic derivative of N-Boc amino-alcohol followed by deprotection using Trifluoro acetic and dichloromethane to obtain a compound of Formula 17, wherein said compound of Formula 8 is:

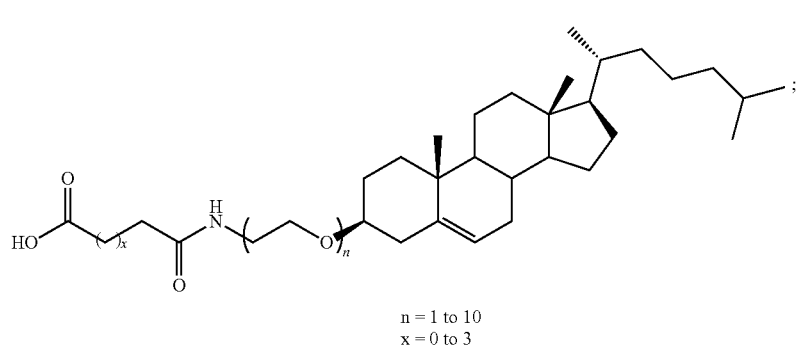

n = 1 to 10
x = 0 to 3 and
wherein said compound of Formula 17 is:

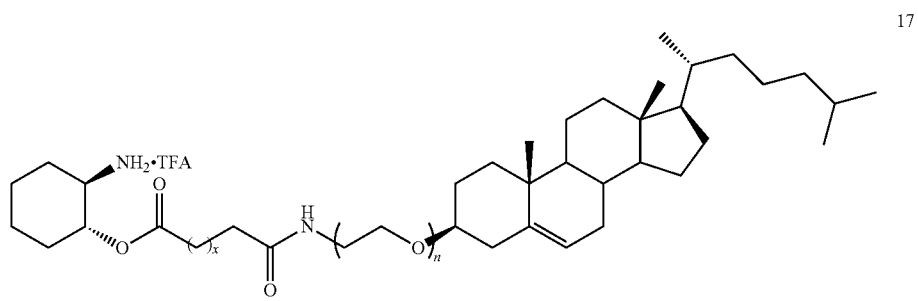

wherein n=1 to 10 and x=0 to 3; and
reacting the compound of Formula 17 with the compound of Formula 22 to obtain the compound of Formula 24;
iii) the process for preparing a compound of Formula 25 comprises the steps of:
reacting a compound of Formula 11 with alicyclic derivative of N-Boc amino-alcohol followed by deprotection using Trifluoro acetic and dichloromethane to obtain compound of Formula 18,
wherein said compound of Formula 11 is:

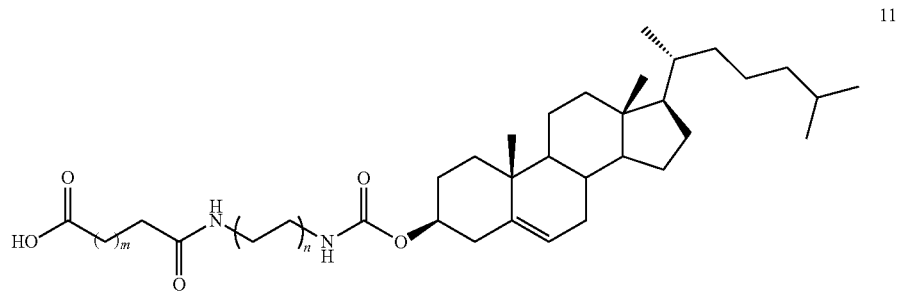

wherein 'n' is 1 to 10 and 'm' is 1 to 4,
wherein said compound of Formula 18 is:

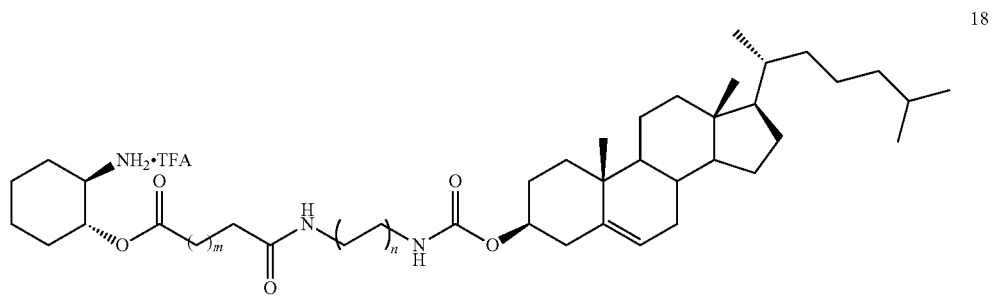

18 wherein 'n' is 1 to 10 and 'm' is 1 to 4; and reacting the compound of Formula 18 with the compound of Formula 22 to obtain the compound of Formula 25;

iv) the process for preparing a compound of Formula 26 comprises the steps of:

reacting a compound of Formula 14 with alicyclic derivative of N-Boc amino-alcohol followed by deprotection using Trifluoro acetic and dichloromethane to obtain a compound of Formula 19, wherein said compound of Formula 14 is:

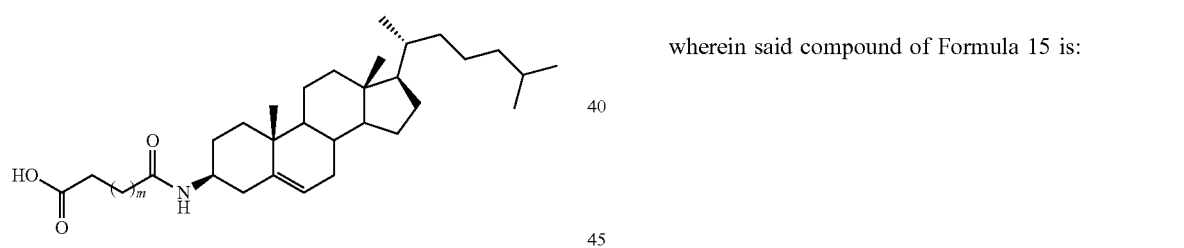

14 wherein 'm' is 1 to 4,
and
wherein said compound of Formula 19 is:

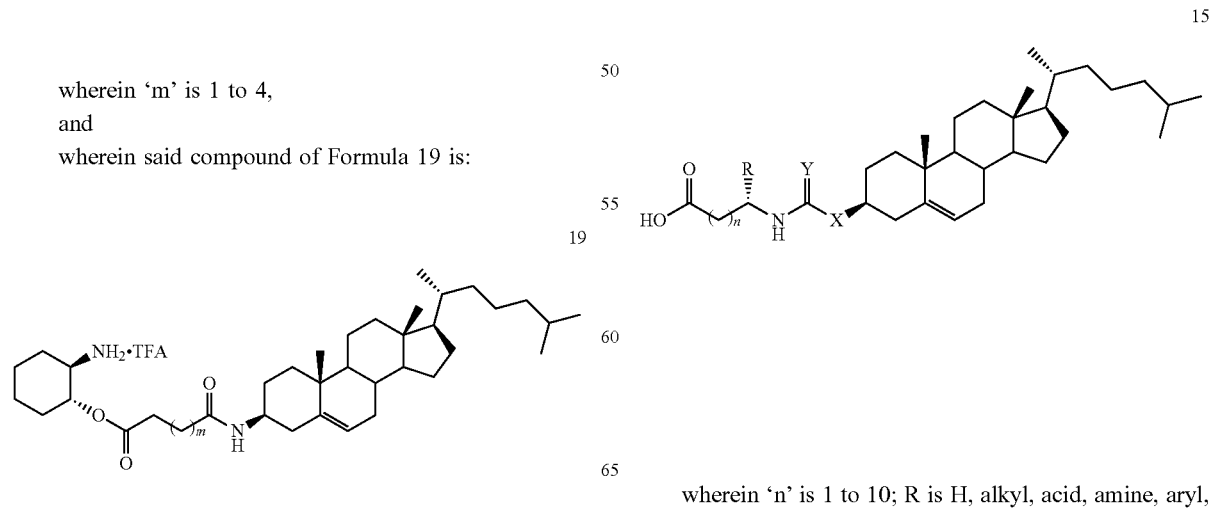

19 wherein 'm' is 1 to 4; and reacting the compound of Formula 19 with the compound of Formula 22 to obtain the compound of Formula 26;

v) the process for preparing a compound of Formula 27 comprises the steps of:

reacting a compound of Formula 15 with alicyclic derivative of N-Boc amino-alcohol followed by deprotection using Trifluoro acetic and dichloromethane to obtain a compound of Formula 20, wherein said compound of Formula 15 is:

15 wherein 'n' is 1 to 10; R is H, alkyl, acid, amine, aryl, thiols; Y is C, O, NH, S; X is CH$_2$, O, NH, S, wherein said compound of Formula 20 is:

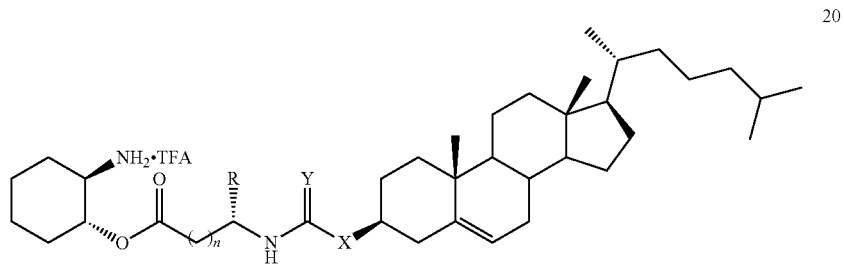

20 wherein 'n' is 1 to 10; R is H, alkyl, acid, amine, aryl, thiols; Y is C, O, NH, S; X is CH$_2$, O, NH, S; and
reacting the compound of Formula 20 with the compound of Formula 22 to obtain the compound of Formula 27; and vi) the process for preparing the compound BLN101 comprises the steps of:
reacting cholesterol with succinic anhydride to obtain BLN-INT,
wherein BLN-INT is

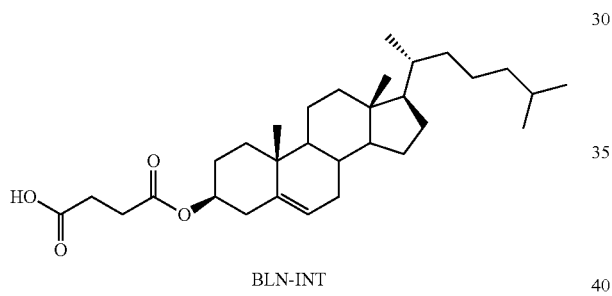

BLN-INT and coupling BLN-INT with BLZ-945 to obtain BLN101 and
wherein
compound of Formula 23 is:

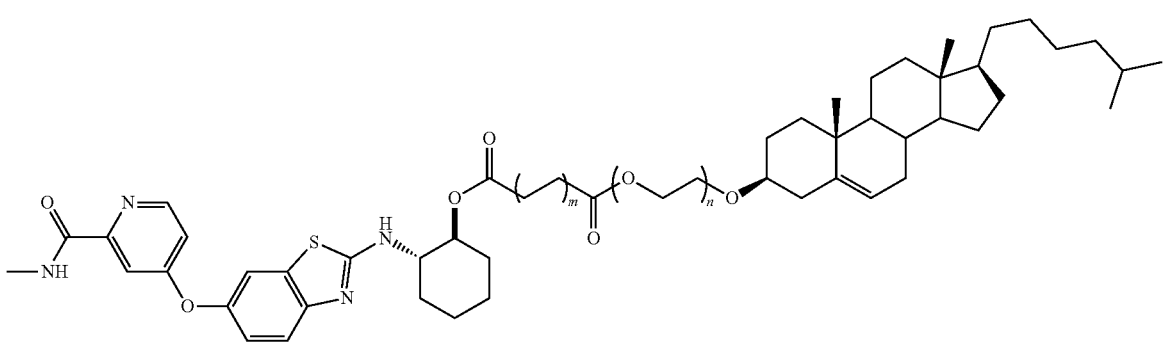

23 wherein 'n' is 1 to 10 and 'm' is 1 to 4;
compound of Formula 24 is:
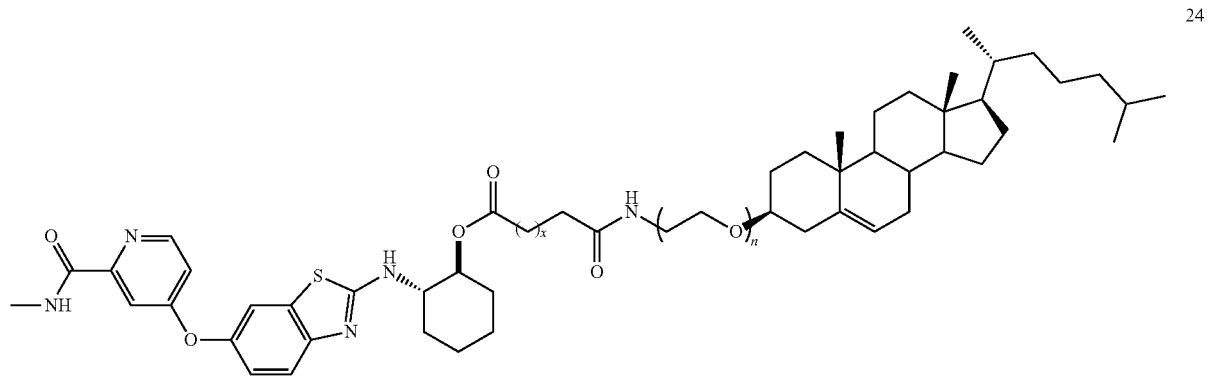
24
wherein 'n' is 1 to 10 and 'x' is 0 to 3;
compound of Formula 25 is:
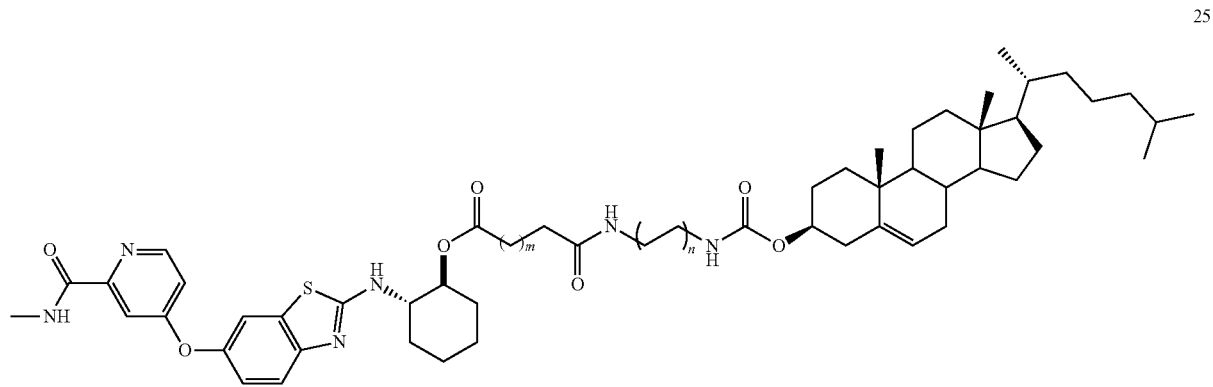
25
wherein 'n' is 1 to 10 and 'm' is 1 to 4;
compound of Formula 26 is:
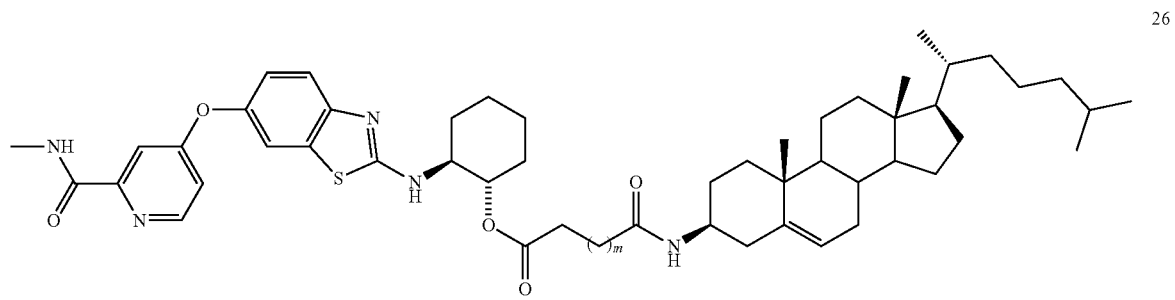
26 wherein 'm' is 1 to 4;
compound of Formula 27 is:

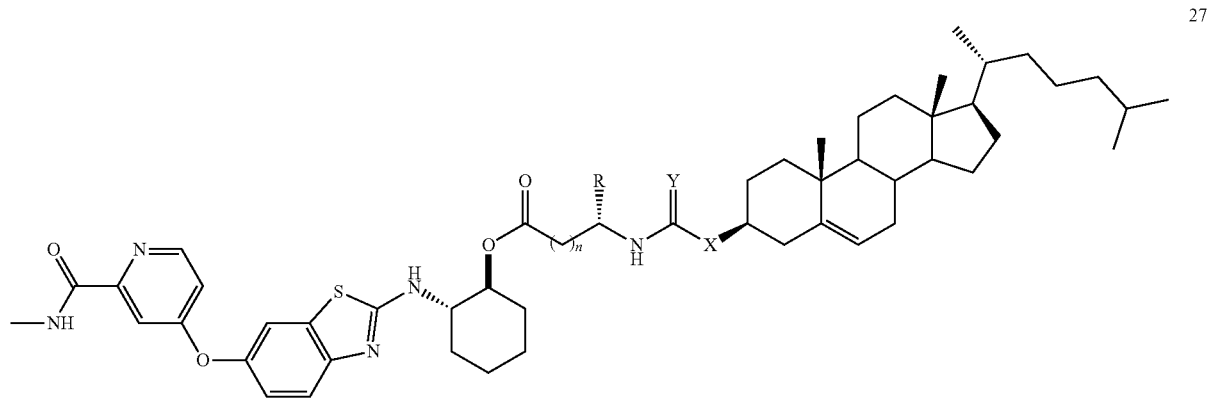

wherein 'n' is 1 to 10; R is H, alkyl, acid, amine, aryl or thiol; Y is C, O, NH, or S; and X is O, NH, or S;

compound BLZ-945 is:

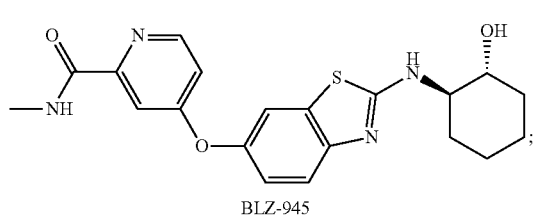 [SMILES: CNC(=O)c1cc(Oc2ccc3nc(N[C@@H]4CCCC[C@H]4O)sc3c2)ccn1]

BLZ-945 and compound BLN101 is:

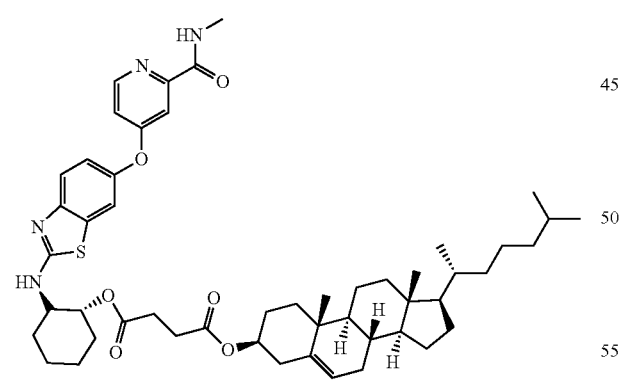

BLN101.

20. A formulation comprising a compound of Formula I:

Formula I wherein, 'Xa' is:

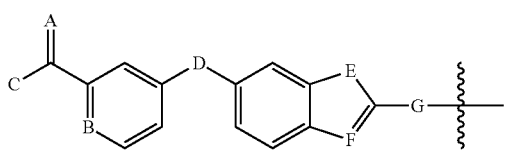

C=hydroxy, alkyl group, aryl group, cycloalkyl group
A=O, NH, S
B=CH, N
D=C, O, NH, S
E=O, NH, S
F=CH, N
G=C, O, NH, S
'Xb' is:

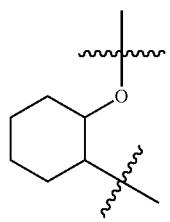 [SMILES: *OC1CCCCC1*]

'Z' is a linker joining 'Xb' with 'L'; and
'L' is a lipid, a lipid derivative or a lipid conjugate or any combinations thereof; or
any salt, tautomeric form, polymorph, or solvate of compound of Formula I thereof; along with phospholipid or PEGylated phospholipid or a combination thereof.

21. The formulation of claim 20, wherein the phospholipid or PEGylated phospholipid is selected from the group consisting of HSPC, DSPC, DPPC, DOPC, POPC, SOPC, Egg PC, DPPE-PEG, DMPE-PEG, DSPE-PEG and any combination thereof; wherein the composition comprises about 1% to about 99% (w/w) of these phospholipid and PEGylated phospholipid or any combination thereof.

22. The formulation of claim 20, wherein the formulation comprises the compound along with HSPC, POPC and DSPE-PEG in a ratio 5:55:35:5, 10:50:35:5 or 15:50:30:5.

* * * * *

UNITED STATES PATENT AND TRADEMARK OFFICE
CERTIFICATE OF CORRECTION

| | | |
|---|---|---|
| PATENT NO. | : 10,736,968 B2 | Page 1 of 1 |
| APPLICATION NO. | : 16/076955 | |
| DATED | : August 11, 2020 | |
| INVENTOR(S) | : Roy et al. | |

It is certified that error appears in the above-identified patent and that said Letters Patent is hereby corrected as shown below:

In the Specification

At Column 1, Line 14:
Insert the following heading and paragraph:
--GOVERNMENT SUPPORT
This invention was made with government support under CA186009 awarded by the National Institutes of Health. The government has certain rights in the invention.--

Signed and Sealed this
Second Day of May, 2023

*Katherine Kelly Vidal*

Katherine Kelly Vidal
*Director of the United States Patent and Trademark Office*